United States Patent
de Keizer

(10) Patent No.: US 11,723,947 B2
(45) Date of Patent: Aug. 15, 2023

(54) ANTI-SENESCENCE COMPOUNDS AND USES THEREOF

(71) Applicant: Erasmus University Medical Center Rotterdam, Rotterdam (NL)

(72) Inventor: Peterus Leonardus Josephus de Keizer, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 101 days.

(21) Appl. No.: 15/545,794

(22) PCT Filed: Jan. 25, 2016

(86) PCT No.: PCT/NL2016/050057
§ 371 (c)(1),
(2) Date: Jul. 24, 2017

(87) PCT Pub. No.: WO2016/118014
PCT Pub. Date: Jul. 28, 2016

(65) Prior Publication Data
US 2018/0015137 A1 Jan. 18, 2018

(30) Foreign Application Priority Data

Jan. 23, 2015 (NL) ..................................... 2014183
Nov. 4, 2015 (EP) ..................................... 15193041

(51) Int. Cl.
*A61K 38/08* (2019.01)
*A61K 38/10* (2006.01)
*A61K 38/17* (2006.01)
*C07K 14/47* (2006.01)

(52) U.S. Cl.
CPC .............. *A61K 38/10* (2013.01); *A61K 38/17* (2013.01); *C07K 14/4702* (2013.01); *C07K 14/4747* (2013.01); *C07K 2319/10* (2013.01)

(58) Field of Classification Search
CPC ... A61K 39/39558; A61K 38/00; A61P 35/00; G01N 33/5011; G01N 33/5005; G01N 33/5073; C12Q 1/6886; C07K 14/00
See application file for complete search history.

(56) References Cited

U.S. PATENT DOCUMENTS

| 2006/0276459 A1 | 12/2006 | Masuda et al. |
| 2013/0288980 A1† | 10/2013 | De Keizer |
| 2013/0288981 A1* | 10/2013 | de Keizer ............ A61K 31/416 514/19.3 |

FOREIGN PATENT DOCUMENTS

| WO | 2013152038 A1 | 10/2013 |
| WO | 2013152041 A1 | 10/2013 |
| WO | 2014206563 A2 | 12/2014 |
| WO | 2018129007 A1 | 7/2018 |

OTHER PUBLICATIONS

Retro Inverso Peptides. Biosynthesis (Apr. 6, 2014 https://www.biosyn.com/tew/retro-inverso-peptides.aspx[Dec. 21, 2019 10:45:33 AM] (Year: 2014).*
FOXO4-DRI. BuckyLabs.com (https://www.buckylabs.com/products/, Aug. 18, 2014.). (Year: 2014).*
Verdoliva et al. Topological Mimicry of Cross-reacting Enantiomeric Peptide Antigens. J Biol Chem. Dec. 22, 1995;270(51):30422-7. (Year: 1995).*
FOXO4-DRI. BuckyLabs. https://www.buckylabs.com/foxo4dri[Aug. 2, 2021 5:48:17 PM] (Year: 2021).*
International Search Report and Written Opinion dated Sep. 12, 2016 in PCT Application No. PCT/NL2016/050057 (18 pages).
Foy Kevin C., et al. "Combination Treatment with HER-2 and VEGF Peptide Mimics Induces Potent Anti-tumor and Anti-angiogenic Responses in Vitro and in Vivo" The Journal of Biological Chemistry, vol. 286, No. 15, pp. 13626-13638, Apr. 2011.
Lüpertz, Regine, et al. "The forkhead transcription factor FOXO4 sensitizes cancer cells to doxorubicin-mediated ctyotoxicity" Carcinogenesis, vol. 29, No. 11, pp. 2045-2052, Aug. 2008.
Zhang, Jinghui, et al. "A Novel Retinoblastoma Therapy from Genomic and Epigenetic Analyses" Nature, vol. 481, No. 7381, pp. 329-334, Jan. 2012.
Atzori et al., "Effect of sequence and stereochemistry reversal on p53 peptide mimicry," PLOS One 8(7):e68723, 2013.
Freidinger et al., "Peptides and their retro enantiomers are topologically nonidentical," J. Am. Chem. Soc. 101:6129-6131, 1979.
Li et al., "Limitations of peptide retro-inverso isomerization in molecular mimicry," J. Biol. Chem. 285(25): 19572-19581, 2010.
Wermuth et al., "Stereoisomerism and Biological Activity of the Selective and Superactive Alpha-v Beta-3 Integrin Inhibitor cyclo(-RGDfV-) and Its Retro-Inverso Peptide," J. Am. Chem. Soc. 119:1328-1335, 1997.
Baar et al., "Targeted Apoptosis of Senescent Cells Restores Tissue Homeostasis in Response to Chemotoxicity and Aging," Cell, 169:132-147 (2017).
Zhang et al., "FOXO4-DRI alleviates age-related testosterone secretion insufficiency by targeting senescent Leydig cells in aged mice," Aging, 12(2):1272-1284 (2020).
Chen, X, et al., "Retro-inverso carbohydrate mimetic peptides with annoxin 1-binding selectivity, are stable in vivo, and target tumor fasculaturo," PLOS ONE vol. 8(12), e60390 (Dec. 2013).†
Li, Ying, et al., Potent retro-inverse D-peptide for simultaneous targeting of angiogenic blood vasculature and tumor cells. Bioconjugate Chemistry vol. 24, pp. 133-43 (2013).†
Matharu, B., et al., Development of retro-inverso peptides as anti-aggregation drugs for B-amyloid in Alzheimer's disease. Peptides. vol. 31, pp. 1866-72 (2010).†

(Continued)

*Primary Examiner* — Aradhana Sasan
*Assistant Examiner* — Jia-Hai Lee
(74) *Attorney, Agent, or Firm* — Dentons US LLP

(57) ABSTRACT

The invention relates to a peptide comprising the amino acid sequence LTLRKEPASEIAQSILEAYSQNG-WANRRSGGKRP, wherein the amino acids in said amino acid sequence are D-amino acid residues, and to methods for the use of this peptide in the treatment of age-related disorders.

8 Claims, 32 Drawing Sheets

Specification includes a Sequence Listing.

(56) References Cited

OTHER PUBLICATIONS

Biswas, N., et al., "Novel peptide isomer strategy for stable inhibition of catecholoamine release: Application to hypertnesion," Hypertension vol. 60, pp. 1552-59 (2012).†

Brugidou, J. et al., The Retro-inverso form of a homeobox-derived short peptide is rapidly internatoized by cultured neurons: A new basis for an efficient intracellular delivery system, Biochemical and BioPhysical Research Communications vol. 214 (2).†

Chorev, M., and M. Goodman, "A Dozen Years of Retro-Inverso Peptidomimetics," Acc. Chem. Res. vol. 26 at pp. 266-73 (1993).†

Braselmann, S., et al., "R406, an orally available spleen tyrosine kinase inhibitor blocks Fc receptor signaling and reduces immune complex-mediated inflammation," The Journal of Pharmacology and Experimental Therapeutics, vol. 319(3), pp. 998-1008 (2006).†

Eter, Eman El, "NQDI 1, An inhibitor of ASK1 attenuates acute ischemic renal injury by modulating oxidative stress and cell death," Cardiovascular & Hematological Agents in Medicinal Chemistry, vol. 11, pp. 179-186 (2013).†

\* cited by examiner
† cited by third party

A)

Sequence : GSHMLEDPGAVTG*RRNWGNQSYAELISQAIESAPEKRLTLAQIYEWMVRTVPY* (SEQ ID NO:10)
Prediction: ----------------HHHHHHHHHH-----HHHHHHHHHHH------

B)

- FOXO4 DRi peptide sequence (excluding TAT)
- Residues shifting upon p53 binding (WGxxxYxxL)

C)

G)

F)

```
MDPGNENSATEAAAIIDLDPDFEPQSRPRSCTWPLPRPEIANQPSEPPEVEPDLGEKVHTEGRSEPILLP
SRLPEPAGGPQPGILGAVTGPRKGGSRRNAWGNQSYAELISQAIESAPEKRLTLAQIYEWMVRTVPYFKD
KGDSNSSAGWKNSIRHNLSLHSKFIKVHNEATGKSSWWMLNPEGGKSGKAPRRRAASMDSSSKLLRGRSK
APKKKPSVLPAPPEGATPTSPVGHFAKWSGSPCSRNREEADMWTTFRPRSSSNASSVSTRLSPLRPESEV
LAEEIPASVSSYAGGVPPTLNEGLELLDGLNLTSSHSLLSRSGLSGFSLQHPGVTGPLHTYSSSLFSPAE
GPLSAGEGCFSSSQALEALLTSDTPPPPADVLMTQVDPILSQAPTLLLLGGLPSSSKLATGVGLCPKPLE
APGPSSLVPTLSMIAPPPVMASAPIPKALGTPVLTPPTEAASQDRMPQDLDLDMYMENLECDMDNIISDL
MDEGEGLDFNFEPDP
``` (SEQ ID NO:3)

Figure 14

MDPGNENSATEAAAIIDLDPDFEPQSRPRSCTWPLPRPEIANQPSEPPEVEPDLGEKAIESAPEKRLTLA
QIYEWMVRTVPYFKDKGDSNSSAGWKNSIRHNLSLHSKFIKVHNEATGKSSWWMLNPEGGKSGKAPRRRA
ASMDSSSKLLRGRSKAPKKKPSVLPAPPEGATPTSPVGHFAKWSGSPCSRNREEADMWTTFRPRSSSNAS
SVSTRLSPLRPESEVLAEEIPASVSSYAGGVPPTLNEGLELLDGLNLTSSHSLLSRSGLSGFSLQHPGVT
GPLHTYSSSLFSPAEGPLSAGEGCFSSSQALEALLTSDTPPPPADVLMTQVDPILSQAPTLLLLGGLPSS
SKLATGVGLCPKPLEAPGPSSLVPTLSMIAPPPVMASAPIPKALGTPVLTPPTEAASQDRMPQDLDLDMY
MENLECDMDNIISDLMDEGEGLDFNFEPDP(SEQ ID NO:4)

Figure 15

```
AAAAGGGGGAGGGAACTGCGGCTAAGGAGACGTTCGGTGATGGGAGCGCAATATATGAGGGGATACAGTG
CCTCAGGTTTAAAAGAGCAGGAAGCTGAGTGAGAGGTTGCAGAAAAAGTGTCTTCGCTCGGCAGAGGTTA
CAGGTGGCATCTCAGAAAGAGCTTTGAGGCTACAGGCTGTAGTCGGGAAGGGGATCGGAGAACTGTGTGA
AGGGACAGCTTAGGGACTAGCGTCCTGGGACTAGGGGGAAGTTCGCGACTTTCTGAAGACTGGCAGGAAT
GTGCCTCCTGGCCCTCGATGCTTCCCCCCTGAGGGGAGGCATCGTGAGGGACTGTGGCAGGCTTCACTGA
ACGCTGAGCCGGGGAGGTCCAACTCCACGTATGGATCCGGGGAATGAGAATTCAGCCACAGAGGCTGCCG
CGATCATAGACCTAGATCCCGACTTCGAACCCCAGAGCCGTCCCCGCTCCTGCACCTGGCCCCTTCCCCG
ACCAGAGATCGCTAACCAGCCGTCCGAGCCGCCCGAGGTGGAGCCAGATCTGGGGGAAAAGGTACACACG
GAGGGGCGCTCAGAGCCGATCCTGTTGCCCTCTCGGCTCCCAGAGCCGGCCGGGGGCCCCCAGCCCGGAA
TCCTGGGGGCTGTAACAGGTCCTCGGAAGGGAGGCTCCCGCCGGAATGCCTGGGGAAATCAGTCATATGC
AGAACTCATCAGCCAGGCCATTGAAAGCGCCCCGGAGAAGCGACTGACACTTGCCCAGATCTACGAGTGG
ATGGTCCGTACTGTACCCTACTTCAAGGACAAGGGTGACAGCAACAGCTCAGCAGGATGGAAGAACTCGA
TCCGCCACAACCTGTCCCTGCACAGCAAGTTCATCAAGGTTCACAACGAGGCCACCGGCAAAAGCTCTTG
GTGGATGCTGAACCCTGAGGGAGGCAAGAGCGGCAAAGCCCCCGCCGCCGGGCCGCCTCCATGGATAGC
AGCAGCAAGCTGCTCCGGGGCCGCAGTAAAGCCCCCAAGAAGAAACCATCTGTGCTGCCAGCTCCACCCG
AAGGTGCCACTCCAACGAGCCCTGTCGGCCACTTTGCCAAGTGGTCAGGCAGCCCTTGCTCTCGAAACCG
TGAACAAGCCCATATGTGGACCACCTTCCGTCCACCAAGCAGTTCAAATGCCAGCAGTGTCAGCACCCGG
CTGTCCCCCTTGAGGCCAGAGTCTGAGGTGCTGGCGGAGGAAATACCAGCTTCAGTCAGCAGTTATGCAG
GGGGTGTCCCTCCCACCCTCAATGAAGGTCTAGAGCTGTTAGATGGGCTCAATCTCACCTCTTCCCATTC
CCTGCTATCTCGGAGTGGTCTCTCTGGCTTCTCTTTGCAGCATCCTGGGGTTACCGGCCCCTTACACACC
TACAGCAGCTCCCTTTTCAGCCCAGCAGAGGGCCCCTGTCAGCAGGAGAAGGGTGCTTCTCCAGCTCCC
AGGCTCTGGAGGCCCTGCTCACCTCTGATACGCCACCACCCCCTGCTGACGTCCTCATGACCCAGGTAGA
TCCCATTCTGTCCCAGGCTCCGACTCTTCTGTTGCTGGGGGGCTTCCTTCCTCCAGTAAGCTGGCCACG
GGCGTCGGCCTGTGTCCCAAGCCCTAGAGGCTCCAGGCCCAGCAGTCTGGTTCCCACCCTTTCTATGA
TAGCACCACCTCCAGTCATGGCAAGTGCCCCATCCCCAAGGCTCTGGGGACTCCTGTGCTCACACCCC
TACTGAAGCTGCAAGCCAAGACAGAATGCCTCAGGATCTAGATCTTGATATGTATATGGAGAACCTGGAG
TGTGACATGGATAACATCATCAGTGACCTCATGGATGAGGGCGAGGGACTGGACTTCAACTTTGAGCCAG
ATCCCTGAGTCATGCCTGGAAGCTTTGTCCCTGCTTCAGATGTGGAGCCAGGCGTGTTCATATCTACTC
TTTACCCTTGAGCCCTCCCCAGGAATTTGGGACCCTGCTTAGAGCTAGGGTGGGGTCTGGTCACACACA
GGTGTTGAAGAAATTATAAAGATAAAGCTGCCCCATCTGGGGACGATATGGGGAGGGAGATGGGAGGGGA
AAGGGGAGAGGGTTTTTCTCACTGTGCCAATTAGGGGGTAAGGCCCCCTCTCAGGAGCCATCATCGGCTT
TCCCCATTCCTACCCACTTAGGCTTTGTAGCAAGATGAGCAATGCTGTTGGAAATGTGAAGTCACCAGTG
GCCTTACCCCTGCCTTTGGGAGCAGGATTTTTTTGTAGAGAGTCTTATCTGAGCTGAGCCAGGCTAGCTG
GAGCCTGGGATTTCTATGCAGTGGCCCCTTAGGCCAGTGATGTGCGGTGGGTGGGCTGTTTAGGGGATCT
GGAAGGGCCAAGGTCTGAGCACTGGAGTGGCTCGCCAGGCCAAATCACCCTTAGAAGGCTGCAGATAACA
GAAAGGCTTTTTATAAACTTTTAAAGAAATATAAACACAAATATAGAGATTTTTTAACCATGGCAGGGTG
CTAGTGGTGGGCAGAATGCTTTTTTTTCTTTCTGAAGGCTTTGTGATAGTGACATGATACAAACACTACA
GACAATAAATATTAGGAGACACAGGGAAGTGGGGAGAGGTGGGGAGTAATAGTAAACACAGGGAAGAGCT
CCCCTACGGACCAGGTATAGAGAAAGGTCTATGCAGAAATAGGTTAGAGTTTCCCTAACAAAAAGCTAA
CCCAGGTCCCCTCATTCCTTCAACTTGTGCCTGGGAGTGTGTGGTGTTAGGGTGCAGCCACACTCTTCTA
TGACCCAGCATGGGTTAGTGCTATGGTGGGAGAGTACATTGAAGGCCTGGAATTAGCTTGGGGCCAGGGA
AGGGACTGGGAGGGCAGAGAACAGAAGGACGGAAGGATTTAGGATGGTAAAGTTAGGTACACAGACCTCC
CTGTTCAAGGCCCCTGACAGCTGTCCCTGCCCTTCTTCCCCTTCCCTGACTGCAGGGTTATGTGGAAGT
GTGTGTGGCAGCAGGCAGCGGGGAGGGGAGGAACAGGGAAGGGGGAGCTGGGGAGCTTGGCTGAGGGTCT
GGGAAATGAGCAGGGATGGGGGGGATGTGGATCAGGTTTACTAGCACCTGCCAGGGAGGCCATCTGGGG
CTCCTTCTCCACCCCAGCCCCCAAAGCAGCCCTTCCCCAGTGCCCTTTGCATCGTCCCTCCCCCACCC
CTGCTGTGGGTTCCCATCATTTCCTGTGTCAGCGCCTGGCCTACCCAGATTGTATCATGTGCTAGATTGG
AGTGGGGAAGTGTGTCAAATCAATAAATGAATAAATTCAATAAATGCCTATAACCAGCAAAAAAAAAAA
AAAAA (SEQ ID NO:5)
```

Figure 16

ANTI-SENESCENCE COMPOUNDS AND USES THEREOF

RELATED APPLICATIONS

The present application is a U.S. National Phase Application under 35 U.S.C. § 371 of International Application No. PCT/NL2016/050057, filed on Jan. 25, 2016, which claims priority to and the benefit of European Patent Application No. 15193041.9 filed Nov. 4, 2015 and Netherlands Patent Application No. 2014183, filed Jan. 23, 2015. All of the foregoing applications are hereby incorporated by reference in their entirety.

This application contains a Sequence Listing which has been submitted electronically in ASCII format and which is incorporated by reference in its entirety. Said ASCII file is named VONL008US-revised.txt, is 15,777 bytes in size and was created on May 21, 2021.

FIELD OF THE INVENTION

The invention is in the field of medicine. More specifically, it is in the field of the treatment of diseases or conditions wherein the removal of senescent cells is beneficial. In particular, the invention relates to compounds for use in the treatment of diseases or conditions wherein the removal of senescent cells is beneficial, for example cancer. The invention also relates to methods of treating an individual suffering, or suspected of suffering, from a disease or condition wherein the removal of senescent cells is beneficial.

BACKGROUND OF THE INVENTION

Apoptosis (programmed cell death) and cellular senescence (permanent arrest of cell proliferation) are mechanisms within the human body that allow for the removal (in the case of apoptosis) or cessation of further cell proliferation (in the case of senescence) of cells upon a variety of negative internal or external stimuli. For example, DNA damage, heat, radiation, nutrient deprivation, viral infection, hypoxia and oxidative stress, can all trigger the release of intracellular apoptotic signals by a cell. Analogously, it is established that cellular senescence may be induced by telomere shortening, oxidative stress, DNA damage, chromatin remodeling, tumor suppressor loss and oncogene induction. Apoptosis and cellular senescence play major roles in human aging, age-related diseases and in keeping the development of cancer within bounds.

Apoptosis provides for the killing of damaged cells. Dying cells that undergo the final stages of apoptosis display phagocytic molecules, marking these cells for phagocytosis by cells possessing the appropriate receptors, such as macrophages. Non-dividing senescent cells can also be cleared by immune cells, but this process is to large extent inefficient. Consequently, whereas apoptosis kills cells, senescent cells are not cleared from tissues and remain metabolically active.

It is shown that senescent cells accumulate with age, and at sites of age-related pathology. Further, senescent cells can acquire mutations that allow them to re-enter a proliferative state. Benign senescent lesions thus retain the capacity to become malignant.

It is important to note that senescent cells—whether in response to inter alia telomere malfunction, DNA damage, oxidative damage, chromatin remodeling, or oncogenic alterations—exhibit great changes in their transcriptomes. As a result, senescent cells affect and alter the tissue microenvironment and potentially the systemic milieu by secreting pro-inflammatory cytokines or chemokines, growth factors and/or matrix degrading proteases. This phenotype is termed the senescence-associated secretory phenotype (SASP). Ultimately, this leads to a decline in tissue homeostasis and accelerates the onset and development of age-related diseases. Indeed, cellular senescence has been associated with a range of age-related pathologies.

Evidence is mounting that normal and pathological degenerative aging phenotypes (loss-of-function) and cancer (gain-of-function) are causally linked to cellular senescence and the SASP. For example, (i) senescent fibroblast have been implicated in decreased milk-production in breast, (ii) senescent pulmonary artery smooth muscle cells are implicated in pulmonary hypertension, (iii) senescent skin cells are related to epidermal thinning and reduced collagen content, (iv) senescent astrocytes and the SASP are implicated in Alzheimers and Parkinson's disease and (v) senescent chondrocytes and SASP have been brought in connection with osteoarthritis. The pathologies that have been brought into connection with cellular senescence and the SASP are even longer and further comprise: Atherosclerosis, lung emphysema, diabetic ulcers, renal disease, kyphosis, osteoporosis, macular degeneration, COPD and insulin resistance, diabetes, obesity, laminopaties such as Hutchinson Gliford's progeria, hernia, sarcopenia and cachexia, arthritis, scoliosis and cancer.

It was recently shown that clearance of senescent cells in a genetic fashion could markedly improve the fitness and decrease parameters of aging in a mouse model for accelerated aging. These mice showed reduced signs of aging measured by kyphosis (excessive bone curvature), muscle strength, fat deposition and cataracts. This provided further evidence that cellular senescence and the SASP is causally linked to age-associated phenotypes and cancer (Baker et al., 2011. Nature 479(7372):232-6). This proof-of-concept evidence was obtained in a genetic fashion that has poor therapeutic applicability.

It is clear in the context of the above that there is a need in the art for compounds that selectively induce apoptosis in senescent cells, as cellular senescence is linked to degenerative (loss-of-function) diseases and cancer (gain of function). There are currently no suitable therapeutically applicable compounds that can selectively induce apoptosis in senescent cells in vivo. It is a goal of the present invention to provide new and existing compounds that therapeutically target senescent cells and that can be used in the treatment of diseases associated with cellular senescence.

SUMMARY OF THE INVENTION

The inventors solved this problem by their unexpected finding that a peptide according to the invention, and the inhibitors NQDI and R406 for use according to the invention, selectively induce apoptosis in senescent cells and, as a consequence, are applicable in the treatment of diseases associated with the presence of senescent cells. The inventors showed inter alfa that compounds according to the invention are effective in the (i) removal of senescent cells in vitro, ex vivo and in vivo (ii) countering symptoms of aging and age-related diseases in a fast aging mouse model, (iii) protection of organ function in an in vivo model for chemotherapy-induced toxicity and (iv) sensitization of a resistant cancer to a chemotherapeutic agent it was previously resistant to or acquired resistance to.

More specifically, the inventors solved this problem by providing a peptide comprising the amino acid sequence of SEQ ID NO:6, wherein the amino acids in said amino acid sequence are D-amino acid residues.

Alternatively, provided is a peptide having at least 70%, preferably at least 90%, amino acid sequence identity to the peptide of claim 1, or a fragment of the peptide of claim 1, wherein said peptide or fragment exhibits apoptosis-inducing activity in senescent cells, preferably wherein said fragment has the amino acid sequence of SEQ ID NO:7, and wherein at least 90% of the amino acids in said amino acid sequence or in said fragment are D-amino acid residues.

In a preferred embodiment of a peptide of the invention, the peptide further comprises a cell-penetrating peptide sequence, preferably said cell-penetrating peptide sequence has the amino acid sequence of SEQ ID NO:1, preferably wherein the amino acids in said cell-penetrating peptide sequence are D-amino acid residues.

In yet another preferred embodiment of a peptide of the invention, further comprising a cell-penetrating peptide sequence, said cell-penetrating peptide is fused to the C-terminal part of said peptide.

In another aspect, the invention provides a pharmaceutical composition comprising a peptide according to the invention.

In a preferred embodiment of a pharmaceutical composition of the invention, the pharmaceutical composition further comprises a chemotherapeutic agent.

In another aspect, the invention provides a retro-inverso peptide of the Forkhead box protein O4, preferably wherein the amino acid sequence of said Forkhead box protein O4 is indicated in FIG. 14 or 15, or a homologue or a fragment thereof, wherein said homologue has an amino acid sequence identity of at least 70% to the retro-inverso amino acid sequence of the Forkhead box protein O4, wherein said homologue exhibits apoptosis-inducing activity in senescent cells, and wherein said fragment has apoptosis-inducing activity in senescent cells.

In another aspect, the invention provides a nucleic acid encoding a peptide according to the invention, optionally comprised in a vector.

In a further aspect, the invention provides a host cell comprising a nucleic acid or vector according to the invention.

In another aspect, the invention provides a peptide, pharmaceutical composition, or nucleic acid according to the invention for use as a medicament, or for use in the treatment of a disorder wherein it is beneficial to remove cells having an increased FOXO4 expression as compared to a control, and expression of pSer15-p53 (active p53 signaling), preferably wherein said disorder is selected from the group of age-related disorders consisting of atherosclerosis; chronic inflammatory diseases such as arthritis or arthrosis; cancer; osteoarthritis; glomerulosclerosis, diabetes including diabetes type I and II; diabetic ulcers; kyphosis; scoliosis; hepatic insufficiency; cirrhosis; Hutchinson-Gilford progeria syndrome (HGPS); laminopaties; osteoporosis; dementia; (cardio)vascular diseases; obesity; metabolic syndrome; acute myocardial infarction; emphysema; insulin sensitivity; boutonneuse fever; sarcopenia; neurodegenerative diseases such as Alzheimer's, Huntington's or Parkinson's disease; cataracts; anemia; hypertension; fibrosis; age-related macular degeneration; COPD; asthma; renal insufficiency; reducing or preventing graft failure after organ or tissue transplantation; incontinence; hearing loss such as deafness; vision loss such as blindness; sleeping disturbances; pain such as joint pain or leg pain; imbalance; fear; depression; breathlessness; weight loss; hair loss; muscle loss; loss of bone density; frailty and/or reduced fitness.

In another aspect, the invention provides a peptide, pharmaceutical composition, or nucleic acid according to the invention for use as a medicament, or for use in the treatment of a disorder wherein the removal of senescent cells is beneficial, preferably wherein said disorder is selected from the group of age-related disorders consisting of atherosclerosis; chronic inflammatory diseases such as arthritis or arthrosis; cancer; osteoarthritis; glomerulosclerosis, diabetes including diabetes type II; diabetic ulcers; kyphosis; scoliosis; hepatic insufficiency; cirrhosis; Hutchinson-Gilford progeria syndrome (HGPS); laminopaties; osteoporosis; dementia; (cardio)vascular diseases; obesity; metabolic syndrome; acute myocardial infarction; emphysema; insulin sensitivity; boutonneuse fever; sarcopenia; neurodegenerative diseases such as Alzheimer's, Huntington's or Parkinson's disease; cataracts; anemia; hypertension; fibrosis; age-related macular degeneration; COPD; asthma; renal insufficiency; reducing or preventing graft failure after organ or tissue transplantation; incontinence; hearing loss such as deafness; vision loss such as blindness; sleeping disturbances; pain such as joint pain or leg pain; imbalance; fear; depression; breathlessness; weight loss; hair loss; muscle loss; loss of bone density; frailty and/or reduced fitness.

In another preferred embodiment of a peptide, pharmaceutical composition, or nucleic acid for use according to the invention, the disorder is cancer, and wherein the use is for administration to a mammalian subject, preferably a human, before, during and/or after subjecting said subject to radiation therapy, and/or before, during or after administering to said subject at least one chemotherapeutic agent.

In still another preferred embodiment of a peptide, pharmaceutical composition, or nucleic acid for use according to the invention, wherein said disorder is cancer, the cancer is a cancer resistant to therapy.

In yet another preferred embodiment of a peptide, pharmaceutical composition, or nucleic acid for use according to the invention, wherein the disorder is cancer and wherein the cancer is a cancer resistant to therapy, said therapy-resistant cancer is metastatic melanoma, breast cancer or glioblastoma, preferably metastatic melanoma, and wherein said therapy to which said cancer is resistant is radiation therapy and/or chemotherapy involving a RAF, MEK or ERK inhibitor or a composition comprising 5' FluoroUracil, Doxorubicin and Cyclofosfamide (FAC) as chemotherapeutic agent, preferably wherein said RAF, MEK or ERK inhibitor is RAF265, trametinib, dabrafenib, selumetinib, vemurafenib, cobemitinib and/or trametinib, more preferably vemurafenib and/or trametinib, and combinations thereof.

In another aspect, the invention provides for a peptide, pharmaceutical composition, or nucleic acid according to the invention for use in removing senescent cells in a human subject suffering from, or expected to suffer from, atherosclerosis; chronic inflammatory diseases such as arthritis or arthrosis; cancer; osteoarthritis; glomerulosclerosis, diabetes including type II diabetes; diabetic ulcers; kyphosis; scoliosis; hepatic insufficiency; cirrhosis; Hutchinson-Gilford progeria syndrome (HGPS); laminopaties; osteoporosis; dementia; (cardio)vascular diseases; obesity; metabolic syndrome; acute myocardial infarction; emphysema; insulin sensitivity; boutonneuse fever; sarcopenia; neurodegenerative diseases such as Alzheimer's, Huntington's or Parkinson's disease; cataracts; anemia; hypertension; fibrosis; age-related macular degeneration; COPD; asthma; renal insufficiency; reducing or preventing graft failure after organ or tissue transplantation, ischemia-reperfusion injury, incontinence; hearing loss such as deafness; vision loss such as blindness; sleeping disturbances; pain such as joint pain or leg pain; imbalance; fear; depression; breathlessness; weight loss; hair loss; muscle loss; loss of bone density; frailty and/or reduced fitness.

In another aspect, the invention provides for a peptide, pharmaceutical composition or nucleic acid according to the invention for use in countering $p21^{cip1}$ expression and/or removing cells that express $p21^{cip1}$, in a human subject suffering from, or expected to suffer from, atherosclerosis, chronic inflammatory diseases such as arthritis or athrosis, cancer, osteoarthritis, glomerulosclerosis, diabetes including type II diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease cataracts, anemia, hypertension, fibrosis, age-related macular degeneration, COPD, asthma, renal insufficiency, reducing or preventing graft failure after organ or tissue transplantation, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness.

In another aspect, the invention provides for a peptide, pharmaceutical composition or nucleic acid according to the invention for use in countering p16INK4a expression and/or removing cells that express p16INK4a in a subject suffering from, or expected to suffer from, atherosclerosis, chronic inflammatory diseases such as arthritis or athrosis, cancer, osteoarthritis, glomerulosclerosis, diabetes including type II diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease cataracts, anemia, hypertension, fibrosis, age-related macular degeneration, COPD, asthma, renal insufficiency, reducing or preventing graft failure after organ or tissue transplantation, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness.

In another aspect, the invention provides for a peptide, pharmaceutical composition or nucleic acid according to the invention for use in countering, or reducing the number of, nuclear serine-15-phosphorylated p53 foci in a subject suffering, or expected to suffer, from atherosclerosis, chronic inflammatory diseases such as arthritis or athrosis, cancer, osteoarthritis, glomerulosclerosis, diabetes including type II diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease cataracts, anemia, hypertension, fibrosis, age-related macular degeneration, COPD, asthma, renal insufficiency, reducing or preventing graft failure after organ or tissue transplantation, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness.

In yet another aspect, the invention provides a kit comprising a first container containing a peptide or nucleic acid according to the invention and a second container containing a chemotherapeutic agent.

In another aspect, the invention provides an inhibitor of ASK1 for use in the treatment of a disorder wherein the removal of senescent cells is beneficial.

In a preferred embodiment of an inhibitor of ASK1 for use according to the invention, the inhibitor of ASK1 is NQDI.

In another preferred embodiment of an inhibitor of ASK1 for use according to the invention, the disorder is selected from the group of age-related disorders consisting of atherosclerosis; chronic inflammatory diseases such as arthritis or arthrosis; cancer; osteoarthritis; glomerulosclerosis, diabetes including diabetes type II; diabetic ulcers; kyphosis; scoliosis; hepatic insufficiency; cirrhosis; Hutchinson-Gilford progeria syndrome (HGPS); laminopaties; osteoporosis; dementia; (cardio)vascular diseases; obesity; metabolic syndrome; acute myocardial infarction; emphysema; insulin sensitivity; boutonneuse fever; sarcopenia; neurodegenerative diseases such as Alzheimer's, Huntington's or Parkinson's disease; cataracts; anemia; hypertension; fibrosis; age-related macular degeneration; COPD; asthma; renal insufficiency; reducing or preventing graft failure after organ or tissue transplantation; incontinence; hearing loss such as deafness; vision loss such as blindness; sleeping disturbances; pain such as joint pain or leg pain; imbalance; fear; depression; breathlessness; weight loss; hair loss; muscle loss; loss of bone density; frailty and/or reduced fitness.

In yet another preferred embodiment of an inhibitor of ASK1 for use according to the invention, the disorder is cancer;

and wherein the use is for administration to a mammalian subject, preferably a human, before, during and/or after subjecting said subject to radiation therapy, and/or before, during or after administering to said subject at least one chemotherapeutic agent.

In still another preferred embodiment of an inhibitor of ASK1 for use according to the invention, wherein the disorder is cancer, said cancer is a cancer resistant to therapy.

In still another preferred embodiment of an inhibitor of ASK1 for use according to the invention, wherein the disorder is cancer and wherein the cancer is a cancer resistant to therapy, said cancer resistant to therapy is metastatic melanoma, breast cancer or glioblastoma, preferably metastatic melanoma, and wherein said therapy to which said cancer is resistant is chemotherapy involving a RAF, MEK or ERK inhibitor as chemotherapeutic agent, preferably wherein said RAF, MEK or ERK inhibitor is RAF265, trametinib, dabrafenib, selumetinib, vemurafenib and/or trametinib, more preferably vemurafenib and/or trametinib.

In another aspect, the invention provides a pharmaceutical combination comprising an inhibitor of ASK1, preferably NQDI, and a chemotherapeutic agent.

In yet another aspect, the invention provides a kit for use in medicine, preferably for use in the treatment of cancer, the kit comprising a first container containing an inhibitor of ASK1, preferably NQDI, and a second container containing a chemotherapeutic agent.

In another aspect, the invention provides an inhibitor of SYK for use in the treatment of a disorder wherein the removal of senescent cells is beneficial, wherein said disorder is not asthma, immune thrombocytopenia, hemolytic anemia, myeloid leukemia and/or lymphoma, preferably wherein said disorders are those listed in claim 15.

In a preferred embodiment of an inhibitor of SYK for use according to the invention, the inhibitor of SYK is R406.

In another preferred embodiment of an inhibitor of SYK for use according to the invention, said disorder is cancer, and wherein the use is for administration to a mammalian subject, preferably a human, before, during and/or after subjecting said subject to radiation therapy and/or before, during or after administering at least one chemotherapeutic agent to said subject, with the proviso that said cancer is not a lymphoma or leukemia, preferably not lymphoma or myeloid leukemia.

In yet another preferred embodiment of an inhibitor of SYK for use according to the invention, wherein the disorder is cancer, the cancer is a cancer that is resistant to therapy.

In yet another preferred embodiment of an inhibitor of SYK for use according to the previous embodiment, said cancer resistant to therapy is metastatic melanoma, breast cancer or glioblastoma, preferably metastatic melanoma, and wherein said therapy to which said cancer is resistant is chemotherapy involving a RAF, MEK or ERK inhibitor as chemotherapeutic agent, preferably wherein said RAF, MEK or ERK inhibitor is RAF265, trametinib, dabrafenib, selumetinib, vemurafenib and/or trametinib, more preferably vemurafenib and/or trametinib.

In another aspect, the invention provides a pharmaceutical combination comprising an inhibitor of SYK, preferably R406, and a chemotherapeutic agent.

In another aspect, the invention provides a kit for use in medicine, the kit comprising a first container containing an inhibitor of SYK, preferably R406, and a second container containing a chemotherapeutic agent.

In another aspect, the invention provides a kit for use in the treatment of cancer, wherein the cancer is not a lymphoma or leukemia, preferably not lymphoma or myeloid leukemia, and wherein the kit comprises a first container containing an inhibitor of SYK, preferably R406, and a second container containing a chemotherapeutic agent.

DESCRIPTION OF THE DRAWINGS

FIG. 14 shows the sequence of the Forkhead box protein 04 (FOXO4), isoform 1 (SEQ ID NO:3).

FIG. 15 shows the sequence of the Forkhead box protein 04 (FOXO4), isoform 2 (SEQ ID NO:4)

FIG. 16 shows the sequence of transcript variant 1 of the FOX04 gene (SEQ ID NO:5).

DETAILED DESCRIPTION OF THE INVENTION

Definitions

Figure 1:
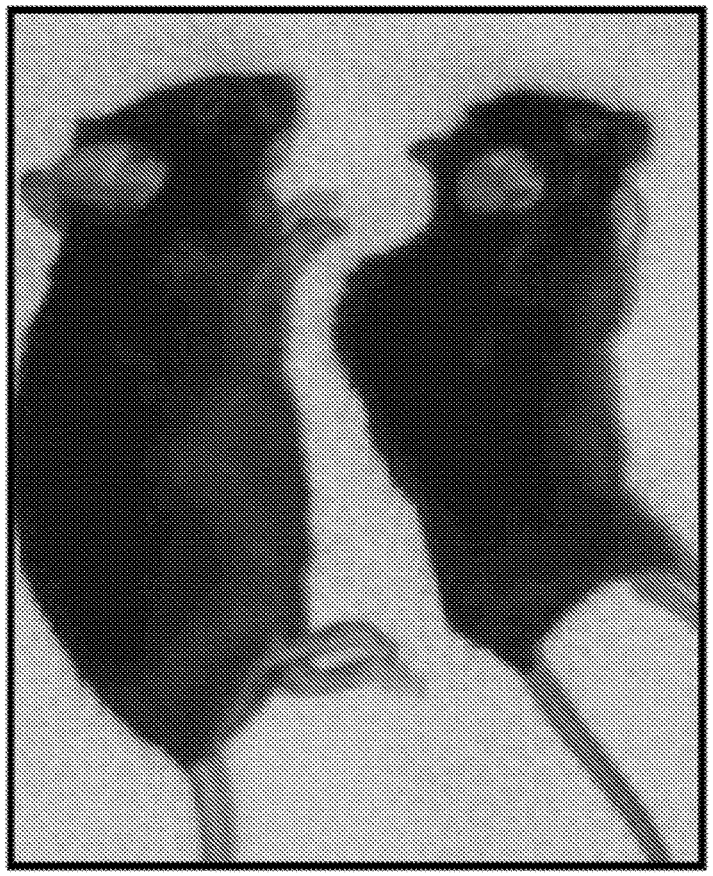
FIG. 1 shows that the overall fitness of the bubr1$^{H/H}$ ink$^{attac-3}$ fast aging mouse model is significantly improved when senescent cells were genetically removed (mice above: senescent cells removed, mice below: senescent cells present). In parallel, these mice showed reduced signs of aging measured by kyphosis (excessive bone curvature), muscle strength, fat deposition and cataracts (Baker et al., 2011. Nature 479(7372):232-6). Senescence is thus causally linked to aging.

The term "peptide", as used herein, refers to synthetically synthesized peptides, preferably peptidomimetics, more preferably D-peptides. The term "peptide" encompasses peptide analogs, which may have, for example, modifications rendering the peptides more stable while in a body or more capable of penetrating into cells. Such modifications include, but are not limited to, N-terminus modification, C-terminus modification, peptide bond modification, including, but not limited to, CH2-NH, CH2-S, CH2-S=O, O=C—NH, CH2-O, CH2-CH2, S=C—NH, CH=CH or CF=CH and backbone modifications. Methods for preparing peptidomimetic compounds are well known in the art and are specified, for example, in Quantitative Drug Design, C.A. Ramsden Gd., Chapter 17.2, F. Choplin Pergamon Press (1992). The term "peptide", as used herein, preferably relates to peptides having less than 200 amino acid residues, more preferably less than 100 amino acid residues and most preferably less than 50 or 40 amino acid residues. A peptide according to the invention may consist of less than 30, 29, 28, 27, 26, 25, 24, 23, 22, 21 or 20 amino acid residues. Preferably, a peptide of the invention contains at least 4, 5, 6, 7, 8, 9,10, 11, 12, 13, 14, 15, 16, 17, 18, 19, 20, 25, 30, 35, 40 or more amino acid residues. The term peptide does not refer to retro-inverso peptides, unless when it is explicitly indicated that the peptide is a retro-inverso peptide. A peptide according to the invention may further comprise an amino acid sequence that facilitates entry of the peptide into a cell, such as the amino acid sequence of SEQ ID NO:1.

The abbreviation "DRI", as used herein, refers to the D-Retro-Inverso Isoform, in which the amino acid sequence is reversed and placed in the D-instead of the L-isoform, in particular with reference to the FOXO4 protein, or a peptide fragment thereof.

The term "D-isoform", as used herein, refers to an amino acid sequence in which at least part of the amino acid residues have the molecular spatial configuration referred to as "D" (Latin dexter; right). A peptide of the invention preferably contains at least one, more preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more D-amino acid residues. A peptide of the invention preferably contains at least 50%, more preferably at least 75%, even more preferably at least 90, 95, 98 or 99%, most preferably 100% D-amino acid residues. The skilled person will appreciate that a DRI peptide according to the invention may contain a combination of L-amino acid residues and D-amino acid residues, or may consist entirely of D-amino acid residues.

The term "% sequence identity" is defined herein as the percentage of nucleotides in a nucleic acid sequence, or amino acids in an amino acid sequence, that is identical with the nucleotides, resp. amino acids, in a nucleic acid or amino acid sequence of interest, after aligning the sequences and optionally introducing gaps, if necessary, to achieve the maximum percent sequence identity. Methods and computer programs for alignments are well known in the art. Sequence identity is calculated over substantially the whole length, preferably the whole (full) length, of an amino acid sequence of interest. The skilled person understands that consecutive amino acid residues in one amino acid sequence are compared to consecutive amino acid residues in another amino acid sequence. Preferably, the configuration of an amino acid residue, for example D or L, is not relevant for determining amino acid sequence identity. For example, a D-Val exhibits sequence identity to a L-Val in the context of the invention.

The term "apoptosis", as used herein, refers to a mechanism of cell death affecting single cells, marked by shrinkage of the cell, condensation of chromatin, and fragmentation of the cell into membrane-bound bodies that are eliminated by phagocytosis. The term "apoptosis" is often used synonymously with the term "programmed cell death".

The term "apoptosis-inducing activity", in the present context, refers to the intrinsic property of a compound to selectively invoke apoptosis in a (i) particular cell type and/or (ii) cell in a particular stage of development or differentiation, due to internal or external stimuli. The skilled person is aware of the existence of in vitro standard assays for determining the extent of apoptosis in a cell culture, for example tests that assess levels of cytoplasmic Cytochrome C (marker for apoptosis) and levels of TUNEL (marker for apoptosis). Using these standard assays, the skilled person can easily assess and compare the apoptosis-inducing activity of different compounds with regard to different cell type or cells in a different developmental stage, e.g. senescent vs. non-senescent cells. Other standard apoptosis assays are an Annexin V assay and a cleaved caspase-3 staining. To detect cell viability, which is essentially the opposite of apoptosis, an MTT assay (colorimetric assay for assessing cell viability), an ATP-detection assay, a real-time cell density (for instance xCELLigence) assay or a colony formation assay can be used.

The term "senescent cells", as used herein, should be interpreted in the context of cellular senescence. The term "senescent cells" includes cells that are characterized by having an essentially permanent growth arrest. Senescent cells are essentially irresponsive to proliferation-cues. For recognition or detection of senescent cells, molecular markers may be used. Several markers for senescent cells have been developed. The term "senescent cell", as used herein, includes cells that are characterized by at least one of the following markers, i.e. (i) essentially permanent growth arrest, preferably indicated by a loss of proliferation markers (e.g. cyclin A, MCM-3 and/or PCNA) and insensitivity to growth cues, (ii) senescence-associated β-galactosidase (SA-B-Gal), (iii) p16$^{INK4a}$ activation and/or expression, (iv) p21$^{cip1}$, preferably p53/p21$^{cip1}$, activation and/or expression (v) senescence-associated heterochromatin foci (SAHF), (vi) DNA-SCARS (DNA segments with chromatin alterations reinforcing senescence) which often partially co-localize with promyelocytic leukemia protein (PML) nuclear bodies, (vii) FOXO4 activation and/or expression, (viii) the senescence-associated secretory phenotype (SASP), preferably characterized by an elevated (>2-fold) presence of SASP markers, such as IL1, IL6 and/or IL8, as compared to a non-senescent cell or a cell in the direct vicinity of said senescent cell and/or (ix) nuclear export of the non-SASP alarmin HMGB1. The skilled person knows when a cell is considered to be in essentially permanent growth arrest, for example by assessing EdU incorporation and/or Ki67 positivity. The phenomenon of senescence can occur at the end of the proliferative lifespan of normal cells or in normal or tumor cells in response to, for example, chemotherapeutic agents, radiation, DNA damage or other cellular insults. The skilled person can thus distinguish senescent cells from inter alia terminally differentiated cells, which in general do not have the characteristics of senescent cells as described hereinabove. Preferably, a senescent cell is characterized by having an essentially permanent or permanent growth arrest, preferably indicated by a lack of proliferation markers in the presence of growth factors. More preferably, a senescent cell is characterized by (i) having an essentially permanent or permanent growth arrest, preferably indicated by a lack of proliferation markers in the presence of growth factors, (ii) p16$^{INK4a}$ activation and/or expression, and/or p21$^{cip1}$, preferably p53/p21$^{cip1}$, activation and/or expression, and/or (iii) FOXO4 activation and/or expression. Most preferably, a senescent cell is characterized by (i) having an essentially permanent or permanent growth arrest, (ii) p16$^{INK4a}$ activation and/or expression and/or p21$^{cip1}$, preferably p53/p21$^{cip1}$, activation and/or expression, (iii) expression of SA-B-Gal and/or (iv) FOXO4 activation and/or expression.

In the context of this paragraph, the term "expression" refers to an increase in gene expression products (RNA) or an increase in protein products as compared to non-senescent cells. The increase in expression as compared to non-senescent cells is preferably with a factor of at least 1.05, 1.1, 1.2, 1.3, 1.4, 1.5, 1.6, 1.7, 1.8, 1.9, 2.0, 3.0, 4.0, 5.0, 6.0 or higher. The skilled person knows how to measure expression levels of genes and proteins. For example, SA-B-Gal can be measured by applying an enzymatic assay using an endogenous enzyme in the lysosomes of senescent cells. Such an assay is normally performed under acidic conditions on fresh material (Dimri et al, PNAS, vol. 92, p. 9363-9367 ((1995). Further exemplifying, p16$^{INK4a}$ and p21$^{cip1}$ expression can be measured by immunohistochemistry using antibodies (e.g. Anti-DKN2A/p16INK4a antibody DCS50.1, ab16123, Abcam, UK; and Anti-p21 antibody, ab7960, Abcam, UK). It is described in the art that senescent cells are withdrawn from the cell cycle through independent activity of p53-p21$^{cip1}$ or p 16$^{ink4a}$, each of which is described as individually sufficient for inducing and maintaining the non-proliferative state (Rodier et al., J Cell Biol 192:547-556 (2011)).

The term "non-senescent cell", as used herein, refers to a "normal" cell, i.e. a cell which in response to growth factors is able to divide, but does not do so in absence of growth factors. The latter would include a cancer cell. Senescent cells are essentially irresponsive to proliferation-cues. A non-senescent cell can be a young human IMR90 lung fibroblast cell ((ATCC® CCL-186™, preferably less than 50 population doublings)) or a normal or healthy cell from a subject that is to be treated. The control can be from a different subject or a pool of such subjects, for instance a subject or group of subjects having an age between 18 and 30 years. The control is preferably from the same tissue and/or organ.

Alternatively, in the context of the medical uses as described herein and providing basis in that context, it was found that a peptide, pharmaceutical composition or nucleic acid according to the invention is especially effective in clearing, removing or killing a cell that is characterized by having an increased FOXO4 expression, and expression of p53. In the context of this paragraph, the term "increased" refers to an increase in gene expression products (RNA) or an increase in protein products as compared to a control. The increase in expression as compared to a control is preferably with a factor of at least 1.05, 1.1, 1.2, 1.3, 1.4, 1.5, 1.6, 1.7, 1.8, 1.9, 2.0, 3.0, 4.0, 5.0, 6.0 or higher. The skilled person knows how to measure expression levels of genes and proteins. Preferably, the expression of p53 is the expression of active pSer15-p53, which can inter alfa be detected and quantified by immunofluorescence and/or immunohistochemistry. As is apparent from the figures, active pSer15-p53 accumulates in nuclear foci in senescent cells, which is countered by a peptide according to the invention. Antibodies against pSer15-p53 are commercially available (Phospho-Ser15 p53 (9286), Cell Signaling Technology Inc., Danvers, Mass., USA). The control is preferably a normal or healthy cell responding to growth factors and able to divide, but does not do so in absence of growth factors. Such a control cell can be a human IMR90 lung fibroblast cell ((ATCC® CCL-186™) or a cell from a subject that is to be treated. The control can be from a different subject than the one to be treated or a pool of such subjects, for instance a subject or pool of subjects having an age between 18 and 30. The control is preferably from the same tissue and/or organ. Preferably, a target cell as described in this context is further characterized by having oxidative stress, detectable by markers activated upon oxidative stress, such as superoxide dismutases SOD1 (Anti-Superoxide Dismutase 1 antibody, ab20926, Abcam, UK) and SOD2 (Anti-SOD2 antibody, Stressgen Biotech, Victoria, BC), catalase (Anti-Catalase antibody, ab16731, Abcam, UK) and/or phosphorylated JNK (phosphoThr183/Tyr185-JNK, Cell Signaling Technology Inc.). In the context of assessing whether oxidative stress is present, a control as described hereinabove can be used. Further, a target cell as described in this paragraph may additionally have one or more of the senescence markers as described herein.

The term "pharmaceutical composition", as used herein, refers to a composition that is made under conditions such that it is suitable for administration to mammals, preferably humans, e.g., it is made under GMP conditions. A pharmaceutical composition according to the invention may comprise pharmaceutically acceptable excipients, e.g., without limitation, stabilizers, bulking agents, buffers, carriers, diluents, vehicles, solubilizers, and binders. The skilled person understands that the selection of appropriate excipients depends on the route of administration and the dosage form, as well as the active ingredient and other factors. A pharmaceutical composition according to the invention is preferably adapted for parenteral administration.

The term "chemotherapeutic agent", as used herein, refers to a compound that inhibits or prevents the viability and/or function of cells, and/or causes destruction of cells (cell death), and/or exerts anti-tumor/anti-proliferative effects, for example, prevents directly or indirectly the development, maturation or spread of tumor cells. The term also includes agents that cause a cytostatic effect only and not a mere cytotoxic effect. The term "chemotherapeutic agent" includes alkylating agents such as platinum drugs (e.g. cisplatin, carboplatin, and oxalaplatin), antimetabolites such as 5-fluorouracil (5-FU), 6-mercaptopurine (6-MP), capecitabine (Xeloda), cladribine, clofarabine, cytarabine (Ara-C), floxuridine, fludarabine, gemcitabine (Gemzar), hydroxyurea and methotrexate, anti-tumor antibiotics, preferably Doxorubicin, topoisomerase inhibitors, mitotic inhibitors, corticosteroids, anti-angiogenic agents, tyrosine kinase inhibitors, protein kinase A inhibitors, members of the cytokine family, radioactive isotopes, inhibitors of the RAF, MEK or ERK families of kinases including, but not limited to vemurafenib, dabrafenib, Raf265, selumetinib and trametinib, and agents commonly used in treatment of melanoma, preferably metastatic melanoma, such as vemurafenib, dabrafenib, Raf265, selumetinib and trametinib. Vemurafenib, Dabrafenib and RAF265 are RAF inhibitors; Trametinib and Selumetinib are MEK inhibitors. Also included as chemotherapeutic agents in the context of this invention are Taxanes such as Paclitaxel or Doxetaxel.

The terms "diseases or conditions wherein the removal of senescent cells is beneficial", "diseases or conditions associated with the presence of senescent cells" and "disorders wherein the removal of senescent cells is beneficial" are used interchangeable.

Figure 5:
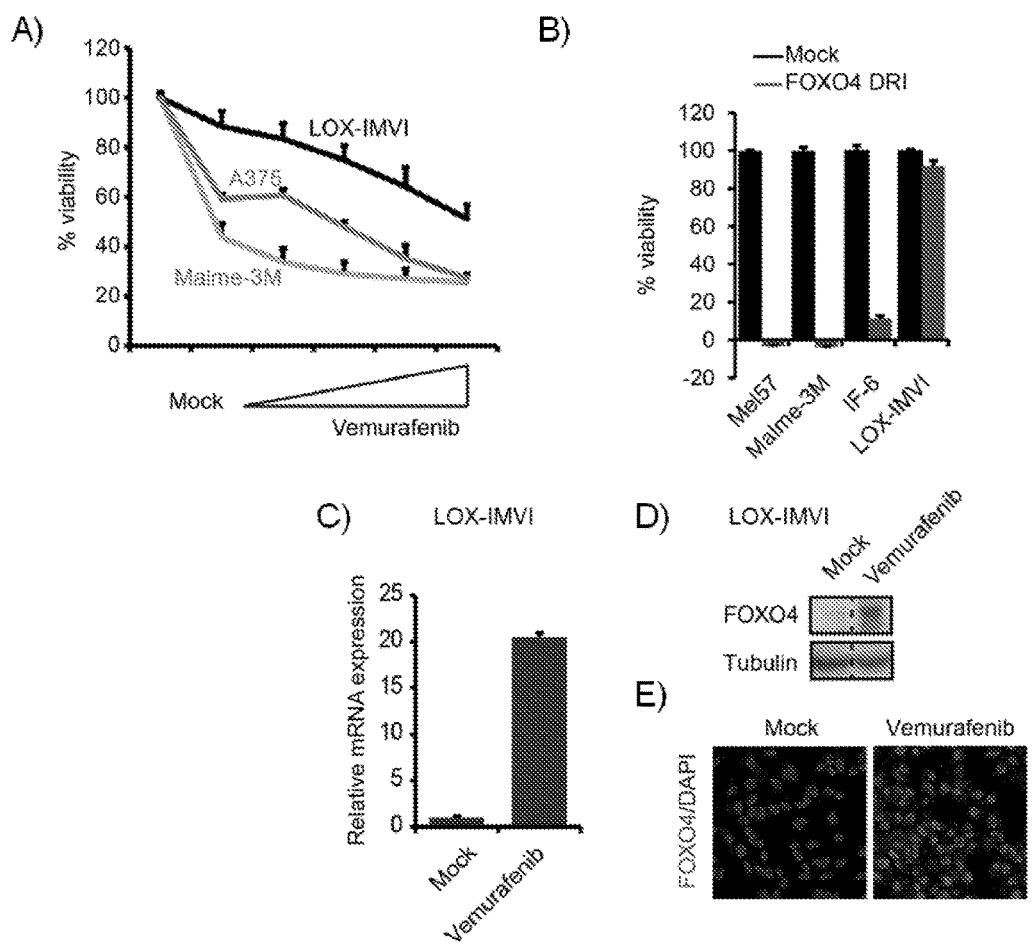
FIG. 5 shows in panel A) a viability assay showing different sensitivity in three distinct metastatic melanoma cell lines to the BRAF$^{V600E}$-inhibitor Vemurafenib. Whereas Malme-3M is sensitive, A375 is intermediate sensitive, LOX-IMVI is resistant to Vemurafenib. Assay as in FIG. 2C with increasing doses of Vemurafenib. Panel B) shows that FOXO4 DRI potently kills ME157, Malme-3M and IF-6, but not LOX-IMVI metastatic melanoma cells. This result shows that FOXO4 DIR has potent anti-melanoma activity. LOX-IMVI however is resistant. Panels C-E) shows that Vemurafenib-treatment of resistant LOX-IMVI cells causes an upregulation in FOXO4 on mRNA (B), and protein levels (C+D). This identifies LOX-IMVI as a potential target for studying the effects of FOXO4 DRI as Vemurafenib itself only shows marginal effects in this line, but it does upregulate FOXO4. Panel F) shows that FOXO4 DRI shows synthetic lethality with RAF/MEK inhibitors in therapy resistant LOX-IMVI. Experiment as in FIG. 2C, but with LOX-IMVI treated with FOXO4 DRI alone, the BRAF$^{V600E}$-inhitors Vemurafenib or Dabrafenib, or the MEK inhibitor Trametinib alone, or a combination hereof. This result shows that while FOXO4 DRI or the RAF/MEK inhibitors on their own do not markedly affect LOX-IMVI viability, the combination shows strong lethality. Panel G) shows the reduction in viability by the combination of Vemurafenib and FOXO4 DRI is caused by apoptosis. LOX-IMVI cells were incubated with FOXO4 DRI or Vemurafenib alone or in combination. The cells were co-treated with the pan-caspase inhibitor QVD-OPH to block caspase-dependent cell death. After 3 days the media was refreshed with new QVD-OPH containing media, but in the absence of FOXO4 DRI or Vemurafenib. At day 5 after initial treatment the cells were fixed and stained for Cytochrome C. Cytochrome C is present in the mitochondria in viable cells and is released into the cytosol when apoptosis is activated. Plotted are the number of cells showing release of Cytochrome C. This shows that while Vemurafenib fails to induce apoptosis in resistant cells FOXO4 overcomes this resistance and strongly synergizes with Vemurafenib to induce apoptosis. Panel G), right, shows that the reduction in viability by the combination of Vemurafenib and FOXO4 DRI leads to a loss in cell density. Experiment as in FIG. 2D with LOX-IMVI treated with Vemurafenib or FOXO4 DRI alone or their combination. Panel H) shows that Vemurafenib treatment promotes its own resistance. Experiment as in FIG. 2D using intermediately sensitive A375, pretreated with one doze of Vemurafenib. The surviving cells and the parental, non-exposed cells were compared for viability after a new round of Vemurafenib. Cells which survived the first round were more resistant to the second round than the parental line. Thus, similar to what is seen in the clinic (see papers from Bernard's lab Nature, 2014), therapy resistance can be mimicked in this set-up. Panel I) shows a similar experiment, but with the MEK inhibitor Trametinib as the second drug. In the clinic RAF inhibitors are frequently followed up on with MEK inhibitors. Also when using Trametinib, the cells which first survived BRAF-inhibition by Vemurafenib proved to be more resistant than the parental line. Panel J) shows that Vemurafenib causes activation of the SASP, marked by surface-bound IL1α. Under basal conditions A375 express nuclear IL1α, which is downregulated early after Vemurafenib. After 6 days however surface-bound IL1α appeared indicative of an active SASP. Together with the data from FIG. 2+3, this indicates that therapy-surviving A375 are a candidate for testing whether FOXO4 DRI could selectively reduce their viability. Panel K) shows that A375 which acquired resistance to Vemurafenib and LOX-IMVI which are intrinsically resistant to Vemurafenib can be resensitized to that drug by FOXO4 DRI. Parental A375, Vemurafenib resistant A375 (survivors of 3 wks chronic Vemurafenib exposure) and intrinsically resistant LOX-IMVI were treated with Vemurafenib or FOXO4 DRI alone or in combination. While regular A375 were sensitive to both drugs individually, the Vemurafenib-resistant A375 and LOX-IMVI showed resistance to Vemurafenib. Excitingly, FOXO4 DRI strongly resensitized these resistant lines to Vemurafenib. Altogether these results show that FOXO4 is a potent anti-melanoma drug in many cases, but in case it fails to directly kills them it at least shows a synthetic lethal function with the most common chemotherapeutic anti-melanoma agent Vemurafenib and other RAF/MEK inhibitors. Panel L) shows that the potency of FOXO4 DRI is enhanced by reactive chemical species such as ROS. LOX-IMVI were assessed for viability in the presence of FOXO4 DRI, the oxidative stress inhibitor N-Acetyl Cysteine (NAC) or the oxidative stressor $H_2O_2$. While FOXO4 DRI and $H_2O_2$ individually only marginally influenced LOX-IMVI viability, together they showed synthetic lethality. This result indicates that FOXO4 DRI is effective against situations and diseases with excessive ROS. This result shows that FOXO4 DRI is of use against any situation where there is excessive ROS, such as cancer or Parkinson's disease. Panels M+N) show that FOXO4 DRI potently synergizes with Vemurafenib in targeting fresh patient-derived melanomas. 3D melanoma organoid cultures (melanoids) were generated as described (Kruiswijk et al, Oncogene, 2015) and treated as in FIG. 5F for viability (M) or stained for Apoptosis using TUNEL (N) according to the manufacturer's protocol (Roche). These results show that not only on cell lines, but also on fresh human melanoma tissue FOXO4 DRI has a potent effect to enhance therapy sensitivity by Vemurafenib.
Figure 5:
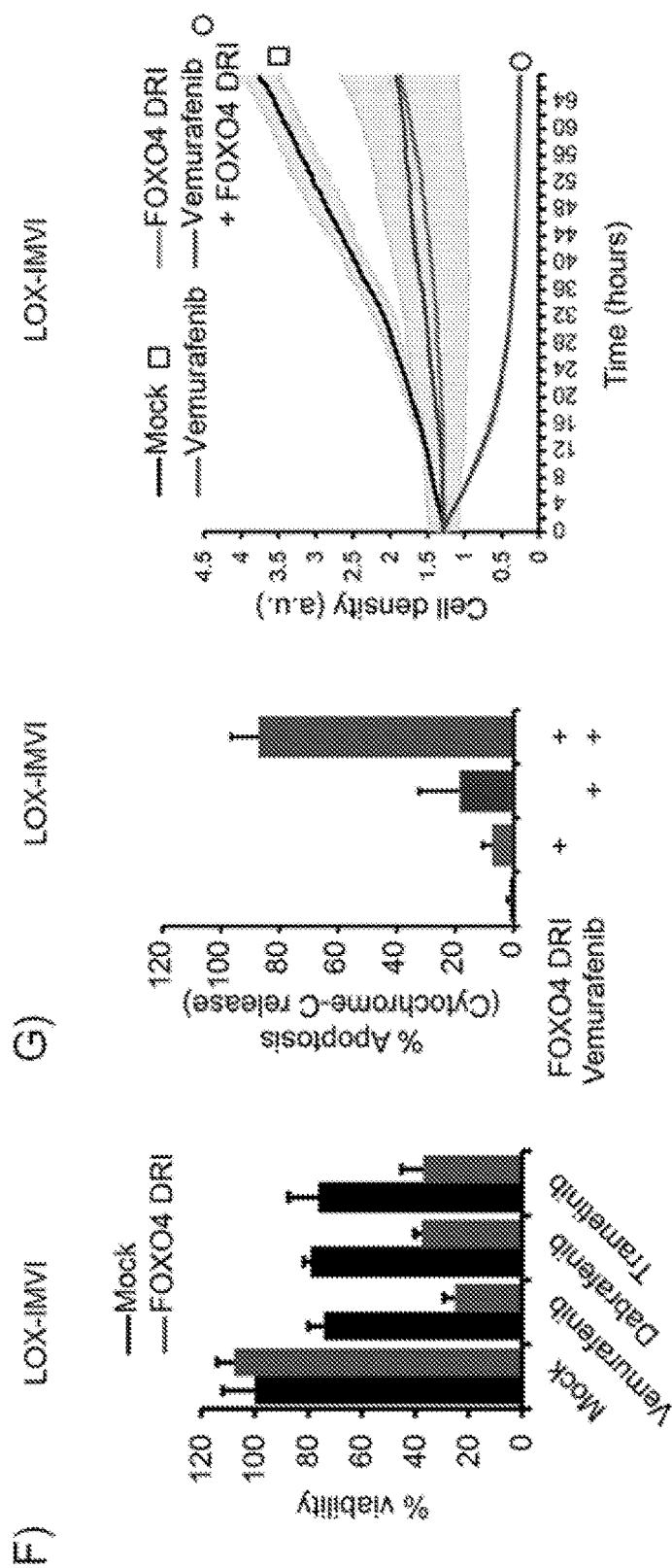
Figure 5:
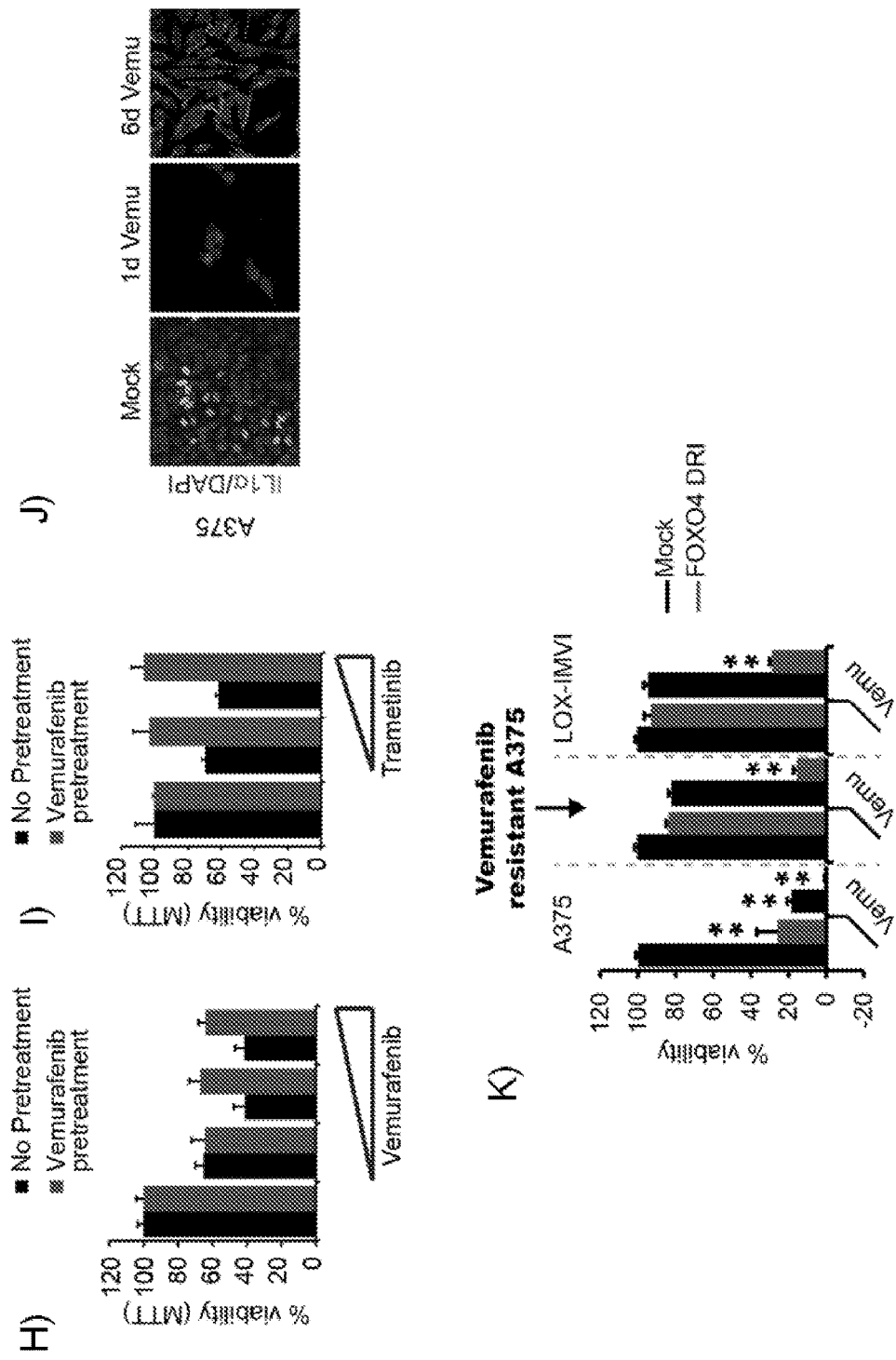
Figure 5:
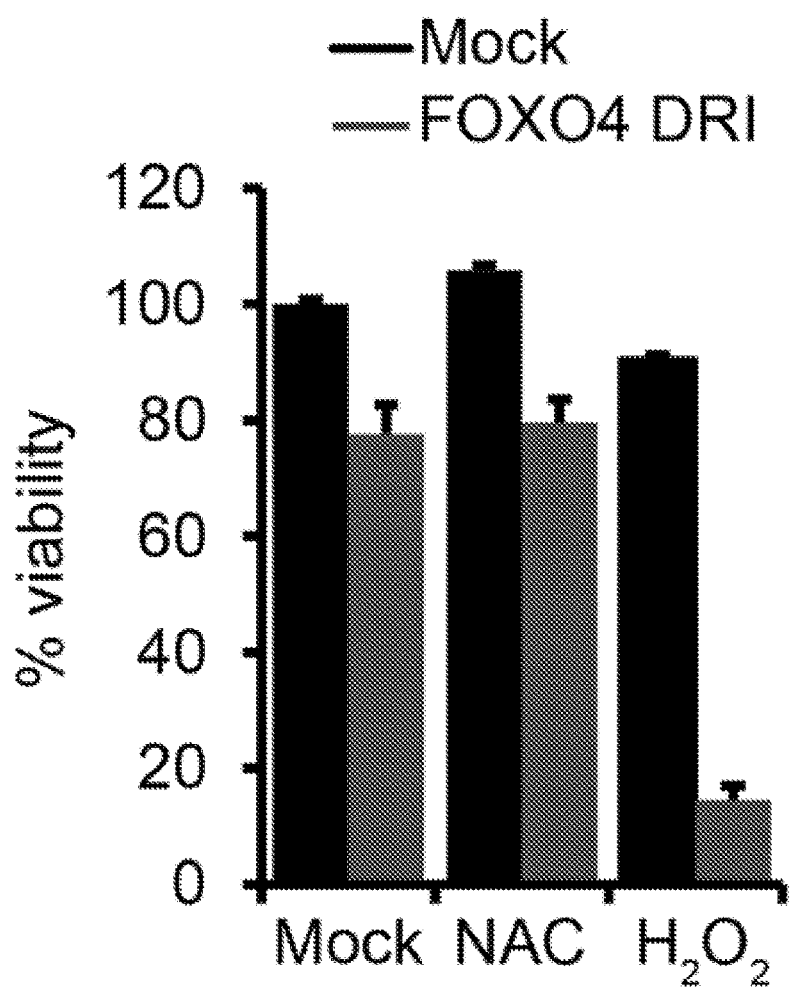
Figure 5:
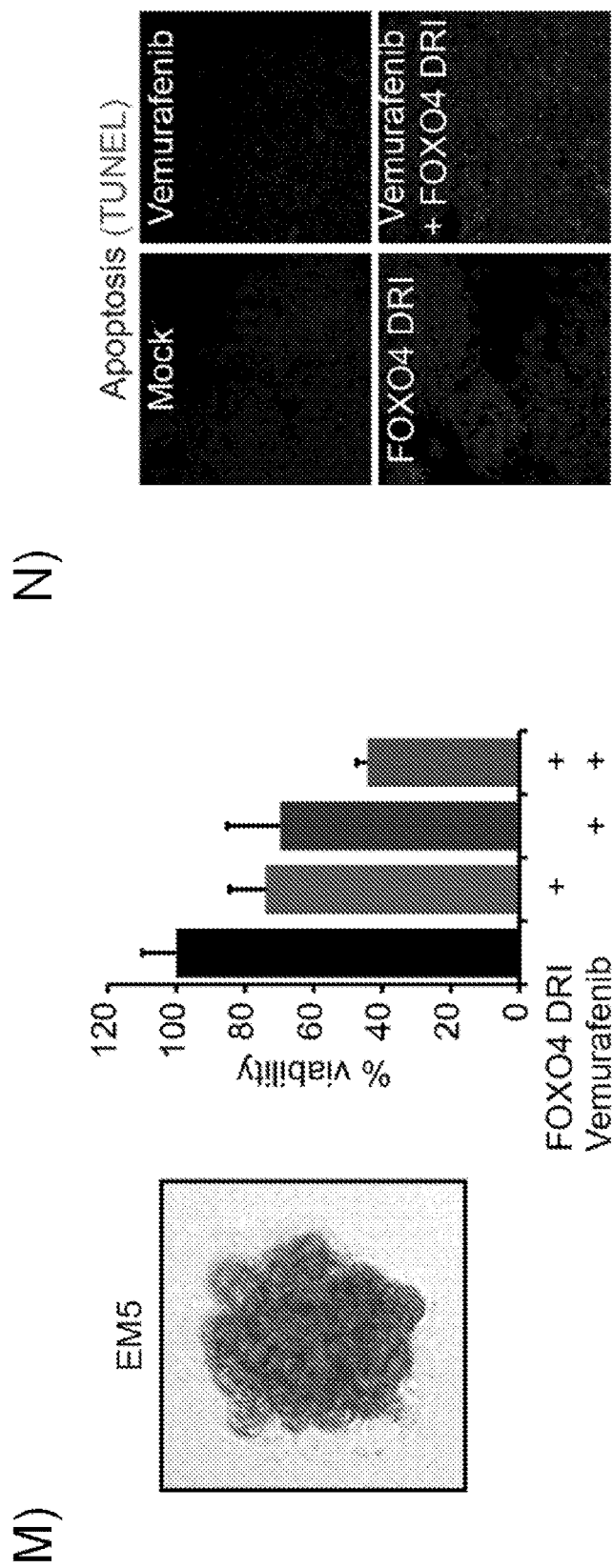

The term "diseases or conditions wherein the removal of senescent cells is beneficial", as used herein, refers to any disease or condition in a mammalian, preferably human, subject wherein removal or clearance or reduced viability of senescent cells is beneficial to the subject suffering from said disease or condition. The term encompasses the situation wherein senescent cells are one, or the only, cause of a disease. The term further relates to the situation wherein senescent cells might become, in the future, the cause of a disease or condition in said subject. Preferably, the treatment of a disease or condition wherein the removal of senescent cells is beneficial, is a disease or condition prevented or preventable by removing senescent cells. For example, it is known that chemotherapeutic agents and radiation therapy induce cellular senescence. It is advantageous to remove these senescent cells in order to prevent the onset of diseases or conditions associated with cellular senescence. The term further encompasses diseases or conditions wherein removal of senescent cells alleviates or reduces symptoms of a disease or condition. It is clear to the skilled person that said removal of senescent cells is beneficial if inter alia the disease or condition can be healed, prevented or if the symptoms of the disease or condition or reduced or alleviated. The skilled person understands that a peptide and inhibitor according to the invention have apoptosis-inducing activity in senescent cells. Removal of senescent cells is coupled to the apoptosis-inducing activity of a peptide and inhibitor according to the invention. More preferably, a peptide or inhibitor according to the invention removes, kills, clears or reduces the viability of at least 1, 2, 3, 4, 5, 10, 15, 20, 25, 30, 40, 50, 60, 70 or 80% of the senescent cells in a mammalian, preferably human, subject, preferably of the senescent cells in an organ or tissue of a mammal, preferably human, subject. The skilled person understands that numerous diseases are linked to senescent cells and treatment for such diseases benefits from the removal of senescent cells. It is preferred that the disease or condition wherein the removal of senescent cells is beneficial, is a disease or condition that is associated with increased levels of reactive oxygen species or reactive nitrogen species, preferably reactive oxygen species such as $H_2O_2$, in a subject, as compared to a subject not having such a disease or disorder. Such a disease or disorder is preferably selected from the list formed by cancer, preferably melanoma, more preferably metastatic melanoma, chronic inflammatory diseases or neurological diseases such as Alzheimer's disease or Parkinson's disease. It was found that the apoptosis-inducing activity of a peptide, pharmaceutical composition or nucleic acid according to the invention was enhanced by the aforementioned reactive species (vide FIG. 5L). The increase in the level of reactive oxygen species and/or reactive nitrogen species is preferably with a factor of at least 1.05, 1.1, 1.2, 1.3, 1.4, 1.5, 1.6, 1.7, 1.8, 1.9, 2.0, 3.0, 4.0, 5.0, 6.0 or higher in a sample representing a disease phenotype, such as a cancer sample, of a subject. The skilled person is aware of method and means for assessing levels of reactive species. Preferably, the disease or condition wherein the removal of senescent cells is beneficial, is selected from the group formed by atherosclerosis, chronic inflammatory diseases such as arthritis or athrosis, cancer, osteoarthritis, diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease, cataracts, anemia, hypertension, fibrosis, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness. A particularly preferred disease or condition wherein the removal of senescent cells is beneficial is a disease or condition associated with or linked to inflammation, preferably chronic inflammation, in a mammalian, preferably human, subject, wherein said inflammation is provided or mediated by senescent cells. Preferably, said senescent cells providing or mediating said inflammation at least partially co-localize in the same organ, more preferably in the same tissue, as the organ, preferably tissue, affected by said disease or condition.

The term "diseases or conditions associated with the presence of senescent cells", as used herein, refers to any disease or condition in a mammalian, preferably human, subject wherein the presence of senescent cells, or presence of cellular senescence, in a mammalian, preferably human, subject is linked to said disease or condition in said subject. The terms "associated with", or "linked to", as used herein, refer to a connection between the presence of senescent cells, or presence of cellular senescence, and said disease or condition. In the aforementioned context, "associated with" or "linked to" can inter alia refer to the senescent cells or cellular senescence (i) as the at least partial cause of a disease or condition, (ii) or as a symptom of a disease or disorder. Preferably, the disease or condition associated with the presence of senescent cells, is selected from the group formed by atherosclerosis, chronic inflammatory diseases such as arthritis or athrosis, cancer, osteoarthritis, diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease cataracts, anemia, hypertension, fibrosis, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness. A particularly preferred disease or condition wherein the removal of senescent cells is beneficial is a disease or condition associated with or linked to inflammation, preferably chronic inflammation, in a mammalian, preferably human, subject, wherein said inflammation is provided or mediated by senescent cells. Preferably, said senescent cells providing or mediating said inflammation at least partially co-localize in the same organ, more preferably in the same tissue, as the organ, preferably tissue, affected by said disease or condition.

The term "condition", as used herein in the context of diseases or disorders wherein the removal of senescent cells is beneficial, refers inter alfa to sleeping disturbances, pain such as joint pain or leg pain, imbalance, fear, depression, breathlessness, weight loss, hair loss, muscle loss, loss of bone density, frailty and reduced fitness. The term "degenerative disease", as used herein, relates to diseases or conditions in which the function and/or structure of a tissue or organ will increasingly deteriorate over time—normally with increasing age—, resulting in a so-called "loss-of-function". The skilled person understands that a degenerative disease may occur in younger people, for-example teens and young adults, as a result of a genetic disorder or unhealthy life-style. The term "degenerative disease" also includes conditions associated with aging such as sleeping disturbances, pain such as joint pain or leg pain, imbalance, fear, depression, breathlessness, weight loss, hair loss, muscle loss, loss of bone density, frailty and reduced fitness.

The terms "administration" or "administering", as used herein, refer to introducing a peptide, inhibitor, preferably NQDI or R406, or pharmaceutical composition, all according to the invention, in a mammalian subject, preferably a human, in a pharmaceutically acceptable form and in a pharmaceutically effective amount by a route of administration such as (i) oral administration, preferably in the form of tablets, capsules, syrups, suspensions, and the like; (ii) administration by injection, preferably in the form of a liquid such as water and administered parenterally, such as intravenous, intramuscular, intraperitoneal, subcutaneous, intraarterial, intracerebral and the like, (iii) transdermal, preferably via topical administration for example in the form of a cream, jelly, powder, or patch; (iv) inhalation, for example in the form of inhalation powders, sprays, suspensions, and the like, and (v) rectal. A peptide, inhibitor, pharmaceutical composition or kit, all according to the invention, are preferably administered parentally, e.g. in a liquid or fluid such as water.

The term "adjuvant", as used herein, refers to a pharmacologically active compound, preferably a peptide or inhibitor, both according to the invention, that is co-administered together with another pharmacologically active compound, preferably a chemotherapeutic agent. An adjuvant may be administered to counter, alleviate or reduce side-effects resulting from a pharmacologically active compound providing the main treatment.

The term "co-administered", as used herein, refers to the administration of a peptide or inhibitor according to the invention together with a chemotherapeutic agent as part of a single dosage form (such as a pharmaceutical composition according to the invention) or as multiple dosage forms, e.g. multiple unit dose wherein the distinct products are packaged together, but formulated separately, e.g. in separate containers. Alternatively, the peptide or inhibitor according to the invention may be administered prior to or before, consecutively with or during, or following or after the administration of a chemotherapeutic agent. In such combination therapy, both a peptide or inhibitor according to the invention and a chemotherapeutic agent are administered via any of the routes as described above and are preferably administered in such a way that the whole provides a synergistic and/or desired effect.

The term "single dosage form", as used herein, refers to a dosage form wherein all compounds are present in a single formulation, preparation or composition, e.g. in one container.

The term "multiple dosage form", as used herein, refers to at least two different—and separate—dosage forms. A particularly preferred multiple dosage form, e.g. in the context of a kit according to the invention, is a multiple unit dose wherein the distinct compounds are packaged together, but formulated separately, e.g. in separate containers.

The term "subject", as used herein, refers to an animal, preferably a mammal such as a human or dog, most preferably a human, who is in need of treatment of a disease or condition wherein the removal of senescent cells is beneficial or who is suffering or suspected to suffer from a disease or condition wherein the removal of senescent cells is beneficial. Preferably, a subject is at least 30 or at least 40 years old. More preferably, the subject is at least 50 years old.

The term "pharmaceutically or therapeutically effective amount", as used herein, refers to an amount, which has a therapeutic effect or is the amount required to produce a therapeutic effect in a subject. For example, a therapeutically or pharmaceutically effective amount of a peptide or inhibitor according to the invention or a pharmaceutical composition of the invention is the amount required to produce a desired therapeutic effect as may be judged by clinical trial results, model animal studies, and/or in vitro studies. The pharmaceutically effective amount depends on several factors, including but not limited to, characteristics of the subject (for example height, weight, sex, age and medical history), the specific disease and the particular type of compound that is used.

The term "radiation therapy", as used herein, refers to an exposure to ionizing radiation, preferably therapeutic, and may include, for example, external beam radiotherapy, photon radiotherapy including X-rays, electron radiotherapy, proton radiotherapy, carbon ion radiotherapy, lithium ion radiotherapy, silicon ion radiotherapy, helium ion radiotherapy, radioisotope therapy, injectable isotopes, e.g., isotopes adhered to or within or admixed with a matrix of any sort. The radiation therapy is preferably photon radiotherapy such as X-rays.

The term "cancer", as used herein, includes cancers such as adrenocortical carcinoma, anal cancer, appendix cancer, astrocytomas, basal cell carcinoma, bile duct cancer, bladder cancer, bone cancer, brain stem glioma, brain tumor, breast cancer, bronchial tumors, carcinoid tumor, cardiac (heart) tumors, central nervous system tumor, cervical cancer, chordoma, colon cancer, colorectal cancer, craniopharyngioma, ductal carcinoma, embryonal tumors, endometrial cancer, ependymoma, esophageal cancer, esthesioneuroblastoma, ewing sarcoma, extracranial germ cell tumor, extragonadal germ cell tumor, extrahepatic bile duct cancer, eye cancer, fallopian tube cancer, gallbladder cancer, gastric (stomach) cancer, gastrointestinal carcinoid tumor, germ cell tumor, head and neck cancer, hepatocellular (liver) cancer, hypopharyngeal cancer, kidney cancer, lung cancer, lip and oral cavity cancer, male breast cancer, metastatic squamous neck cancer, mouth cancer, nasal cavity and paranasal sinus cancer, ovarian cancer, pancreatic cancer, parathyroid cancer, penile cancer, prostate cancer, rectal cancer, salivary gland cancer, skin cancer, small intestine cancer, stomach (gastric) cancer, thyroid cancer, lymphomas, urethral cancer, vaginal cancer, and/or vulvar cancer. A particularly preferred cancer is a cancer having a high FOXO4 expression level. Preferably, the FOXO4 expression is at least a factor 1.05, preferably a factor 1.1, more preferably a factor 1.2, 1.3, 1.4, 1.5, 1.6, 1.7, 1.8, 1.9, 2.0, 3.0, 4.0, 5.0, or a factor 6.0 higher than FOXO4 expression in non-cancerous cells, preferably non-cancerous or healthy or normal cells, more preferably non-cancerous, or healthy or normal cells in the direct vicinity of said cancer.

The term "resistant cancer" is used interchangeable with the term "cancer resistant to therapy" and refers to both (i) a cancer that is resistant to at least one chemotherapeutic agent, wherein the resistance is acquired after treatment with said at least one chemotherapeutic agent, i.e. a resistance-acquired cancer and (ii) a cancer that is resistant to at least one chemotherapeutic agent wherein the resistance is de novo, i.e. a de novo resistant cancer wherein the resistance is present prior to treatment with said at least one chemotherapeutic agent. The term "resistant cancer" refers to cancer cells that are able to survive in the presence of at least one chemotherapeutic agent whereas a normal, non-resistant cancer cell would either show signs of cell toxicity, cell death or cellular senescence. The skilled person can easily assess whether a cancer is a resistant cancer, namely by assessing cell viability or apoptosis-inducing activity after bringing a suitable chemotherapeutic agent in contact with a cancer originating from a subject. The skilled person is aware of the existence of standard assays to screen for resistant cancers, such as MTT assays, ATP-measurements and/or apoptosis-assays such as TUNEL, Cytochrome C release or Cleaved Caspase-3 assays. In the context of a peptide or inhibitor of ASK1 according to the invention, the resistant cancer may be a lymphoma. In the context of an inhibitor of SYK, the resistant cancer is preferably not a lymphoma or myeloid leukemia. More preferably, the resistant cancer is a resistant adrenocortical carcinoma, anal cancer, appendix cancer, astrocytomas, basal cell carcinoma, bile duct cancer, bladder cancer, bone cancer, brain stem glioma, brain tumor, breast cancer, bronchial tumors, carcinoid tumor, cardiac (heart) tumors, central nervous system tumor, cervical cancer, chordoma, colon cancer, colorectal cancer, craniopharyngioma, ductal carcinoma, embryonal tumors, endometrial cancer, ependymoma, esophageal cancer, esthesioneuroblastoma, ewing sarcoma, extracranial germ cell tumor, extragonadal germ cell tumor, extrahepatic bile duct cancer, glioblastoma, eye cancer, fallopian tube cancer, gallbladder cancer, gastric (stomach) cancer, gastrointestinal carcinoid tumor, germ cell tumor, head and neck cancer, hepatocellular (liver) cancer, hypopharyngeal cancer, kidney cancer, lung cancer, lip and oral cavity cancer, male breast cancer, metastatic squamous neck cancer, mouth cancer, nasal cavity and paranasal sinus cancer, ovarian cancer, pancreatic cancer, parathyroid cancer, penile cancer, prostate cancer, rectal cancer, salivary gland cancer, skin cancer, small intestine cancer, stomach (gastric) cancer, thyroid cancer, urethral cancer, vaginal cancer, and/or vulvar cancer. Most preferably, the resistant cancer is metastatic melanoma, breast cancer or glioblastoma. In the context of the present invention, said resistant cancer, as mentioned hereinbefore, is preferably metastatic melanoma, breast cancer or glioblastoma, more preferably metastatic melanoma, and is resistant to treatment with at least one chemotherapeutic agent, preferably a RAF, MEK or ERK inhibitor including RAF265, trametinib, dabrafenib, selumetinib, vemurafenib and/or trametinib, more preferably vemurafenib and/or trametinib. When the resistant cancer is a resistant breast cancer, the chemotherapeutic agent to which said cancer is resistant, is preferably a chemotherapeutic composition comprising 5'FluoroUracil, Doxorubicin (Adriamycin) and Cyclofosfamide (FAC). Every possible combination of a resistant cancer and at least one chemotherapeutic agent, preferably a RAF, MEK or ERK inhibitor, is envisaged herein. A particularly preferred resistant cancer is a cancer with an increased FOXO4 expression level. A resistant cancer has an increased FOXO4 expression level if its FOXO4 expression level is at least a factor 1.05, 1.1, 1.2, 1.3, 1.4, 1.5, 1.6, 1.7, 1.8, 1.9, 2.0, 3.0, 4.0, 5.0, 6.0 or higher than the FOXO4 expression level of a non-resistant cancer. In the context of this paragraph, the term "expression" preferably refers to gene expression products (RNA) or protein products. The skilled person is well aware of methods for measuring expression product levels.

The term "countering", as used herein, refers to the effect of opposing, counteracting, inhibiting, blocking, delaying, or reducing the symptom or phenomenon in a subject. Preferably, "countering" refers to counteracting.

The term "sensitizing", as used herein, refers to the process of making resistant cancer cells susceptible to the effect of a chemotherapeutic agent. Said term refers to the process wherein a cancer cell moves from a state in which it is able to survive in the presence of at least one chemotherapeutic agent to a state wherein it shows signs of cell toxicity, cell death and/or cellular senescence as a result of the effect of said at least one chemotherapeutic agent. The term "sensitizing" encompasses and preferably relates to "re-sensitizing", the latter of which is applicable in the context of sensitizing a resistance-acquired cancer. Preferably, the term "sensitizing" refers to increasing the susceptibility of a resistant cancer in a subject towards at least one chemotherapeutic agent said cancer is resistant to, such that, upon administration of said at least one chemotherapeutic agent, cell viability of said resistant cancer is reduced by at least 5, 6, 7, 8, 9, 10, 15, 20, 25, 30, 35, 40, 45, 50, 60, 70, 75, 80 or 90% as compared to the cell viability of a non-sensitized resistant cancer equivalent to said resistant cancer treated with said at least one chemotherapeutic agent. Cell viability is measurable by a MTT assay, an ATP-detection assay, a cell density assay or a colony formation assay. Alternatively, the term "sensitizing" may refer to increasing the susceptibility of a resistant cancer in a subject towards at least one chemotherapeutic agent said cancer is resistant to, such that, upon administration of said at least one chemotherapeutic agent, the level of apoptosis is increased by at least 25, 30, 35, 40, 45, 50, 55, 60, 70, 80, 90, 100, 200 or 300% as compared to the level of apoptosis in a non-sensitized resistant cancer equivalent to said resistant cancer treated with said at least one chemotherapeutic agent.

The term "compound", as used herein, refers to any kind of molecule, preferably a pharmacologically active molecule such as a peptide or inhibitor according to the invention or a chemotherapeutic agent.

The term "container", as used herein, refers to a receptacle adapted for holding or storing a compound, preferably a compound (peptide or inhibitor according to the invention or a chemotherapeutic agent) formulated in a pharmaceutically acceptable form. The preferred formulation is a formulation adapted for parenteral administration. The receptacle may suitable be a vial, bottle, jar, or flexible packaging.

The term "containing", as used in the context of kits according to the invention, should not be explained in such a way that the container only contains, or consists of, a peptide or inhibitor according to the invention or a chemotherapeutic agent. The container may suitably contain other compounds or substances than a peptide or inhibitor according to the invention or a chemotherapeutic agent.

The term "inhibitor", as used herein, refers to any compound, natural or synthetic, which can reduce the activity of a gene product. Accordingly, an inhibitor may inhibit the activity of a protein that is encoded by a gene either directly or indirectly. Direct inhibition can be obtained, for instance, by binding to a protein and thereby preventing the protein from binding a target (such as a binding partner) or preventing protein activity (such as enzymatic activity). Indirect inhibition can be obtained, for instance, by binding to a protein's intended target, such as a binding partner, thereby blocking or reducing activity of the protein. Preferably the inhibitor is an ASK1 inhibitor or SYK inhibitor. More preferably, said ASK1 inhibitor and SYK inhibitor are kinase inhibitors, i.e. inhibit kinase activity of ASK1 and SYK. It is particularly preferred that said ASK1 inhibitor and SYK inhibitor are kinase inhibitors that also exhibit apoptosis-inducing active in senescent cells. Most preferred are ASK1 inhibitor NQDI and SYK inhibitor R406. The skilled person is well-aware of standard inhibition assays wherein screening for target compounds, such as ASK1 and SYK inhibitors occurs. As already stated earlier, standard assays for determining apoptosis-inducing activity are within the common general knowledge of the skilled person. In suitable embodiments, the ASK1 inhibitor or SYK inhibitor is an interfering RNA molecule, preferably siRNA, inhibiting protein expression of ASK1 or SYK. In other embodiments the inhibitor of ASK1 or SYK is a morpholino oligomer.

The term "interfering RNA molecule", as used herein, refers to all RNA or RNA-like molecules that can interact with RISC and participate in RISC-mediated changes in gene expression. Examples of interfering RNA molecules that can interact with RISC include short hairpin RNAs (shRNAs), single-stranded siRNAs, microRNAs (miRNAs), and dicer-substrate 27-mer duplexes.

The term "morpholino oligomer", as used herein, refers to a polymer of the genetic nitrogeneous bases, adenine, guanine, cytosine, and thymine, in which the nitrogenous bases are linked to a 6-membered morpholine ring; as opposed to ribose or deoxyribose as in RNA or DNA.

The term "forkhead box O4 (FOXO4) gene" refers to the protein-coding gene having Gene ID 4303 (Genbank 7 Dec. 2014), and NCBI Reference Sequence: NC_000023.11 and consisting of 7386 nucleotides, also known as AFX; AFX1; or MLLT7.

The terms "FOX04 peptide" and "FOX04 protein", which terms are interchangeably herein, refer to a protein translated from a transcript of the forkhead box protein 04 gene, referred to as the Forkhead box protein 04. Isoform 1 (SEQ ID NO:3) (FIG. 14) of this protein is encoded by transcript variant 1 of the FOX04 gene (SEQ ID NO:5) (FIG. 16). Isoform 2 (SEQ ID NO:4) (FIG. 15) is encoded by transcript variant 2. The term "FOXO4 DRI Peptide" refers to the reverse-inverso peptide or protein of the "FOXO4 peptide", preferably, but not necessarily, in an all-D amino acid configuration, and preferably in the form of the isoform 1 protein.

The term "ASK1", as used herein, refers to mammalian, preferably human apoptosis signal-regulating kinase 1 (ASK1), also known as mitogen-activated protein kinase kinase kinase 5 (MAP3K5). ASK1 is a MAP kinase and it is suggested that it activates c-Jun N-terminal kinase (JNK). The amino-acid sequences of human and mouse ASK1 are known in the art. For example, human ASK1 is accessible in Genbank under Acc. No. NP_005914 (3 May 2014).

The term "SYK", as used herein, refers to mammalian, preferably human Spleen Tyrosine Kinase. SYK is a member of the Syk family of tyrosine kinases. The amino-acid sequences of human and mouse ASK1 are known in the art. For example, the amino-acid sequence of human SYK is accessible in Genbank under Acc. No. P43405 (26 Nov. 2014).

The term "NQDI", as used herein, refers to a molecule also commonly referred to as "NQDI 1" having the chemical name 2,7-Dihydro-2,7-dioxo-3H-naphtho[1,2,3-de]quinoline-1-carboxylic acid ethyl ester and having the structural formula:

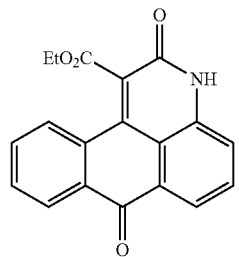 [SMILES: CCOC(=O)c1c2c3c(cccc3[nH]c1=O)C(=O)c1ccccc1-2]

NQDI is freely available on the market (e.g. Tocris, NQDI 1, Cat. No. 4429). NQDI is preferably formulated in a pharmaceutically acceptable form, more preferably a pharmaceutically accepted form adapted for parental administration.

The term "R406", as used herein, refers to a SYK inhibitor. R406 is also referred to as 6-(5-fluoro-2-(3,4,5-trimethoxyphenylamino)pyrimidin-4-ylamino)-2,2-dimethyl-2H-pyrido[3,2-b][1,4] oxazin-3 (4H)-one benzenesulfonate and has the structural formula:

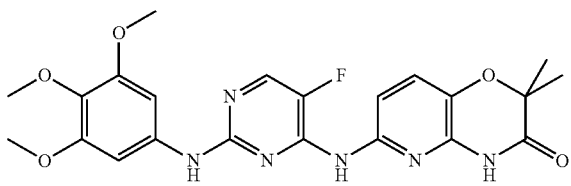

R406 is available on the market (e.g. via Selleckchem, US). R406 is preferably formulated in a pharmaceutically acceptable form, more preferably a pharmaceutically accepted form adapted for parental administration. It is specifically noted that R788 (also referred to as Fostamatinib) is a prodrug of R406. R406 is a liver degradation product of R788. The skilled person understands that, instead of R406, also R788 can be administered to a mammalian, preferably human, subject in order to provide R406 to said subject. From a function point of view, the skilled person understands that the term "R406" can be interchanged with "R788" or any other prodrug that releases R406 upon interaction with a mammalian, preferable human, subject after administration of said prodrug to said subject. Instead of the term "R406", as used in this application, the term R788 can be used. R788 is available on the market (e.g. Santa Cruz Biotechnology, CAS 901119-35-5) and is known under the chemical name 6-(5-fluoro-2-(3,4,5-trimethoxyphenylamino)pyrimidin-4-ylamino)-2,2-dimethyl-3-oxo-2,3-dihydropyrido[3,2-b][1,4]oxazin-4-yl)methyl dihydrogen phosphate. The structural formula of R788 is:

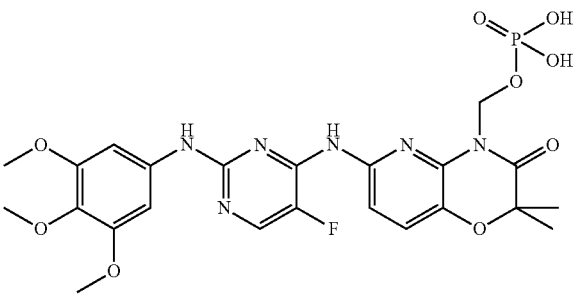

DESCRIPTION OF THE PREFERRED EMBODIMENTS

The Link Between Cellular Senescence and Disease

Cellular senescence has been associated with a range of age-related pathologies. There is substantial proof for the link between cellular senescence and age-associated phenotypes. Excitingly, it was recently shown that clearance of senescent cells in a genetic fashion could markedly improve the fitness and decrease parameters of aging in a mouse model for accelerated aging (Baker et al., 2011, vide above; FIG. 1). These mice showed reduced signs of aging measured by kyphosis (excessive bone curvature), muscle strength, fat deposition and cataracts. This provided further evidence that cellular senescence and the SASP is causally linked to age-associated phenotypes and cancer. It is commonly accepted that the SASP may affect and alter the tissue microenvironment and potentially the systemic milieu by secreting pro-inflammatory cytokines or chemokines, growth factors and/or matrix degrading proteases. The SASP is generally formed by factors such as IL-6 and IL-8; a variety of monocyte chemo attractant proteins and macrophage inflammatory proteins; and inflammation regulating proteins, such as granulocyte/macrophage colony—stimulating factor. The most highly conserved feature between the SASP of different senescent cells are the pro-inflammatory cytokines. It is the secretion of such factors that cause chronic inflammation, at least locally and possibly systemically. It is commonly accepted that chronic inflammation is a cause of, or an important contributor to, virtually every major age-related disease, both degenerative (loss-of-function) and cancer.

Peptides of the Invention

The present invention relates inter alia to a peptide comprising or consisting of an amino acid sequence having at least 50% sequence identity to a peptide having the amino acid sequence of SEQ ID NO:7 or SEQ ID NO:6; or a fragment of said peptide comprising or consisting of the amino acid sequence of SEQ ID NO:7; wherein said peptide, preferably said amino acid sequence, and said fragment contain at least one D-amino acid residue, preferably all-D; and wherein said peptide, preferably said amino acid sequence, and said fragment exhibit apoptosis-inducing activity in senescent cells. The invention further envisages peptidomimetics of the peptides of the invention.

Alternatively, the present invention relates to a peptide comprising or consisting of an amino acid sequence having at least 50% sequence identity to a peptide having the amino acid sequence of SEQ ID NO:8; or a fragment of said peptide comprising or consisting of the amino acid sequence of SEQ ID NO:7; wherein said peptide, preferably said amino acid sequence, and said fragment contain at least one D-amino acid residue, preferably all-D; and wherein said peptide, preferably said amino acid sequence, and said fragment exhibit apoptosis-inducing activity in senescent cells.

Without wishing to be bound by theory, it is believed that the residues L, Y and GW, as underlined in the amino acid sequence SEIAQSILEAYSQNGW (SEQ ID NO:7), and the residues on the amino-terminal side of said 1 residue, interact with p53. It is suggested that as a result of that interaction the senescence-favoring interaction between FOXO4 and p53 tumor suppressor protein is inhibited and apoptosis is favored over cellular senescence.

A peptide according to the invention, such as the FOXO4 DRI Peptide as used in the Examples, may further comprise an amino acid sequence that is not derived from the FOXO4 peptide (or from the FOXO4 DRI peptide, meaning that the sequence does not occur therein), such as the sequence of SEQ ID NO:1, which facilitates entry of the peptide sequence having the apoptosis-inducing activity into a cell. The skilled person understands that this amino acid sequence can be replaced by any other amino acid sequence that facilitates entry of the peptide into a cell. In other words, said amino acid sequence is not suggested to have any apoptosis-inducing activity. Said amino acid sequence preferably contains at least one D-amino acid residue, more preferably all amino acid residues in said amino acid sequence are D-amino acid residues.

Preferably, a peptide according to the invention selectively exhibits apoptosis-inducing activity in senescent cells, i.e. not in non-senescent cells. A peptide according to the invention favors apoptosis in senescent cells over apoptosis in non-senescent cells by at least a factor 1.1, 1.2, 1.3, 1.4, 1.5, 1.6, 1.7, 1.8, 1.9, 2.0, 2.5, 3, 4, 5 or higher. A peptide according to the invention is preferably isolated.

Using common general knowledge, one skilled in the art can assess via a standard in vitro test whether a peptide according to the invention exhibits apoptosis-inducing activity in senescent cells. For example, one provides a cell culture of senescent cells, e.g. obtained by subjecting said cell culture to ionizing radiation or a chemotherapeutic agent and non-senescent cells. Other ways of providing senescent cells are (i) continuous passaging until replicative senescence occurs (=telomere shortening), (ii) via the use oxidative stressors as $H_2O_2$ and Rotenone, (iii) chromatin remodelers as Sodiumdibutirate, or (iv) expression of hyperactivated oncogenes such as RASG12V or BRAFV600E. The presence of senescence cells can be established by testing for SA-B-GAL. The second step is to administer to both cell cultures a peptide according to the invention and measure one or more markers of apoptosis, such as (i) staining for cytoplasmic cytochrome C or (ii) staining for TUNEL. With regard to cytochrome C, data can be quantified by counting the number of cells (DAPI can be used to indicate a cell) in which Cytochrome C has been released from the mitochondria to the cytosol or (at later stages) the number of cells that have disappeared completely. This assay can be done in presence of a caspase-inhibitor so the cells that are about to undergo apoptosis (indicated by release of Cytochrome C into the cytosol) are not allowed to actually die as caspases are required for that. The benefit of this assay is that it is possible to get a cumulative count on the amount of senescence over several days (for example 5 days). With regard to the TUNEL staining, the percentage of nuclei (DAPI-positive) which stain positive for TUNEL are counted. This can easily be performed by eye, but it is also possible to use a software tool called Cellprofiler (freeware) to do it objectively.

A peptide according to the invention is considered to exhibit apoptosis-inducing activity in senescent cells if it kills, clears or removes senescent cells. Preferably, a peptide according to the invention is considered to exhibit apoptosis-inducing activity in senescent cells if it kills, clears, removes or reduces the viability of at least 5, 10, 15, 20, 25, 30, 40, 50, 60, 70 or 80% of the cells in a senescent cell culture.

A peptide according to the invention preferably comprises or consists of an amino acid sequence that shows at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to the peptide having the amino acid sequence of SEQ ID NO:7, SEQ ID NO:6 or SEQ ID NO:8; and wherein said peptide contains at least one D-amino acid residue; and wherein said peptide exhibits apoptosis-inducing activity in senescent cells. More preferably said amino acid sequence has at least 90%, most preferably 100%, sequence identity with said peptides.

Preferably, a peptide or fragment of said peptide according to the invention contains at least 2, 3, 4, 5, 6, 7, 8, 9, 10, 11, 12, 13, 14, 15, 16, 17, 18, 19, 20, 21, 22, 23, 24, 25, 27, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59,60 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 D-amino acid residues. More preferably, all amino acid residues in said peptide according to the invention are D-amino acid residues. Most preferably, a peptide according to the invention is a DRI-peptide, i.e. a retro-inverso or D-retro-enantiomer of the FOXO4 peptide, consisting of D-amino acid derivatives and having the reversed sequence of the FOXO4 peptide, preferably with reference to the natural, human FOXO4 protein, or a peptide fragment thereof.

The term "D-amino acid-derivative" refers to a FOXO4 derivative as defined herein (including the above defined C- and N-terminally truncated peptide fragments having the reverse amino acid sequence of the FOXO4 peptide) that include at least one amino acid in the D configuration, preferably more than 25% D, more preferably more than 50% D, even more preferably more than 75% D, even more preferably more than 85% D, and still more preferably more than 95% D amino acid residues. A special category of these D-amino acid derivatives are the peptides that are composed of only D amino acids (i.e. in which no L amino acid is present). This special category is herein defined as D-only derivatives.

Figure 3:
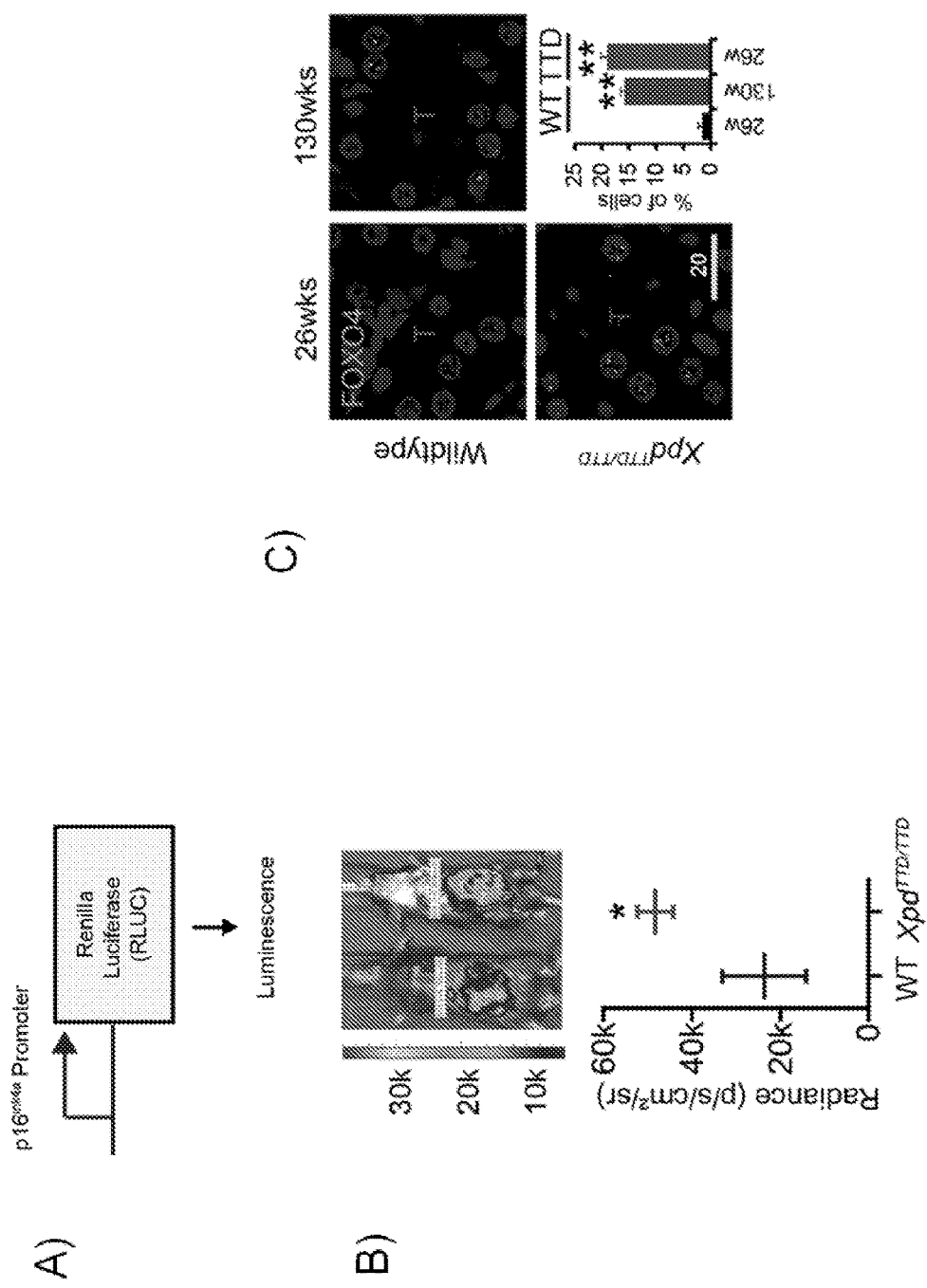
FIG. 3 shows in panel A) a schematic representation of the construct used to detect p16INK4A-positive senescent cells in vivo. In this construct the promoter of the prominent senescence gene p16INK4A drives expression of the bioluminescent enzyme Renilla Luciferase (RLUC). Thus, injection of the mice with the RLUC substrate Coelenterazine allows specific visualization of $p16^{INK4A}$-positive senescent cells in vivo. This can be performed for the same mice in time providing a tool for visualizing the effects of anti-senescence treatments. Panel B) shows that fast aging $Xpd^{TTD/TTD}$ mice (de Boer et al, 1998 and 2002) crossed with the P16-3MR model mouse, which contains RLUC (hereinafter also referred to as P16::3MR) senescence-detection model show elevated levels of p16ink4a-positive senescence in vivo, allowing longitudinal analysis of senescence. Six wildtype and $Xpd^{TTD/TTD}$ mice were crossed with animals and at 26 wks of age injected with Coelenterazine for detection of senescence. Panel C) shows that fast aging $Xpd^{TTD/TTD}$ mice show elevated expression of FOXO4, similar to normally aged (130 w) old wildtype mice. Wildtype and $Xpd^{TTD/TTD}$ mice were sacrificed at the indicated ages and the kidneys were stained for FOXO4. The number of FOXO4 positive tubular cells (T) were quantified. Thus, FOXO4 is elevated in $Xpd^{TTD/TTD}$ mice, which also show elevated levels of senescence. This allow for testing of FOXO4 DRI to see if senescence is influenced. Panel D) shows that FOXO4 DRI strongly reduces $p16^{INK4A}$-positive senescence in 26 w old $Xpd^{TTD/TTD}$ mice. Top: treatment plan for addressing levels of P16::3MR-positive senescence in $Xpd^{TTD/TTD}$. For six $Xpd^{TTD/TTD}$-P16::3MR mice the baseline levels of RLUC radiance were determined as in FIG. 3B. After recovery of the imaging procedure (between 5-20 days for individual animals) the animals were divided over two groups of three animals. One group was injected for 4 consecutive days with 10 mg/kg FOXO4 DRI per intravenous injection, whereas the other was Mock injected with the solvent (PBS). The change in $p16^{INK4A}$-positive senescence (RLUC) was determined at 14 d after first injection and compared to baseline signal. Shown on the bottom left is a representative $Xpd^{TTD/TTD}$-p16::3MR animal before and after FOXO4 DRI treatment. On the bottom right the change in RLUC radiance for both groups is plotted. P<0.05: Student's t-test. Note that due to the increase in age, Mock treatment and the imaging procedure the RLUC signal of the Mock treated group has increased, while it was strongly decreased in the FOXO4 DRI injected group. Panel E) shows an anecdotal example showing that FOXO4 DRI can improve kyphosis (bone curvature) and muscle mass of $Xpd^{TTD/TTD}$ mice. CT images of the spine and tibia of a mouse treated as in FIG. 3D were taken before and after treatment with FOXO4 DRI. FOXO4 DRI lowered the curvature of the spine (Top) and increased the muscle mass (Bottom: quantified red area). Panel F) shows old wildtype mice and 26 w young $Xpd^{TTD/TTD}$ show reduced renal filtering capacity evident from elevated presence of plasma [Urea]. Blood samples of 4-5 wildtype or $Xpd^{TTD/TTD}$ mice were collected at the indicated time-points and analyzed for the presence of Urea in the plasma fraction, as a marker for reduced renal filtering capacity. [Urea] was determined using a kit according to the manufacturer's protocol (Gentaur). * p<0.05, ** p<0.01. One-way ANOVA with Bonferroni post-test correction (GraphPad Prism). Note that in time the plasma [Urea] in wildtype animals increased. 26 w young $Xpd^{TTD/TTD}$ mice show a similar loss of renal filtering capacity, validating $Xpd^{TTD/TTD}$ mice of this age as a model for loss of renal function. Panel G) shows $Xpd^{TTD/TTD}$ mice having reduced fitness, indicated by impaired running wheel behavior and loss of hair. Left: Six wildtype and $Xpd^{TTD/TTD}$ mice were placed in running wheel cages and the turns/day were continuously measured for four days. Displayed is the absolute distance run for each group in km per day. * P<0.01. Student's t-test. Right: Representative images a wildtype and $Xpd^{TTD/TTD}$ mouse at 26 w to show the striking general difference in fur coat (See also FIG. 3K for quantification). Panel H) shows a treatment plan for addressing organ function, running wheel behavior and fur score of 26 w old wildtype and $Xpd^{TTD/TTD}$ mice following Mock or FOXO4 DRI treatment. 4-5 wildtype or $Xpd^{TTD/TTD}$ mice were placed in runningwheel cages and after allowing sufficient time for adjustment a baseline peripheral (cheek) blood sample was taken. After 5 days of recovery the mice were treated on day 0, 2 and 4 with 5 mg/kg FOXO4 DRI through intravenous injection. At 28 d after the first injection another blood sample was taken and the mice were sacrificed right after. Panel I) shows FOXO4 DRI reduces spontaneously occurring renal glomerulosclerosis and improved renal filtering capacity in fast aging $Xpd^{TTD/TTD}$ mice. 26 w old wildtype and $Xpd^{TTD/TTD}$ mice were treated as in H). Kidney tissues were fixed in formalin right after sacrifice and embedded in paraffin. Sum thick sections were stained in Periodic acid-Schiff (PAS) solution and scored for glomerulosclerosis as described in Adamcszak et al, 2003, JASN. Glomeruli were graded 0-4 for sclerosis. Representative images of wildtype and $Xpd^{TTD/TTD}$ glomeruli of Mock or FOXO4 DRI-treated mice are shown (top) and quantified (left). * P<0.05 One-way Anova with Bonferroni post-test correction. From the same animals the levels of plasma [Urea] was determined before and after treatment. The ratio was calculated and the change in concentration plotted. * P<0.05. Student's t-test. Note that FOXO4 DRI-treated $Xpd^{TTD/TTD}$ mice showed a decrease in plasma [Urea] indicating an improvement in renal function (right). Panel J) shows a representative example of FOXO4 DRI inducing an improvement in running wheel behavior of an $Xpd^{TTD/TTD}$, but not wildtype mouse. Note that since $Xpd^{TTD/TTD}$ mice show strongly reduced running wheel capacity (FIG. 3G) the data are normalized to 100% for the respective running wheel behavior at the start of the experiment for each animal. Panel K) shows a quantification of the average changes in running wheel behavior in wildtype and $Xpd^{TTD/TTD}$ mice after Mock or FOXO4 DRI treatment. Plotted is the ratio of the distances run marked by the orange boxed in panel J). Panel L) shows that FOXO4 DRI counters hair loss of $Xpd^{TTD/TTD}$ mice. Left panels: Representative images of the same $Xpd^{TTD/TTD}$ animal before and after treatment with FOXO4 DRI. Right panel: quantification of the average change in fur score Wildtype fur is scored as 0, while 4 denotes the most deteriorated fur. A negative score means improvement in appearance after treatment. Not that all wildtype animals either before or after the experiment scored 0. *p<0.05 Student's t-test. Altogether these results show that in vivo FOXO4 DRI potently counters agingassociated senescence and provides a strong healthspan benefit as determined by fitness, renal function and reduced hair loss. Panels M) and N) show that FOXO4 DRI counteracts the weight loss seen in fast aging $Xpd^{TTD/TTD}$ mice. More specifically, panel M) shows that fast aging $Xpd^{TTD/TTD}$ mice show reduced body weight compared to wildtype littermates (26 w of age). Panel N) shows that FOXO4 DRI improves the body weight specifically in the fast aging $Xpd^{TTD/TTD}$ mice. The mice treated as in A)-L) were analyzed for changes in body weight over the time course of the experiment and the % change plotted. Panels O)-R) show that FOXO4 DRI does not induce toxicity to the hematopoietic system. Wildtype and fast aging $Xpd^{TTD/TTD}$ mice were treated as in FIG. 3H)-L) and the indicated blood parameters were determined at the end of the experiment.
Figure 3:
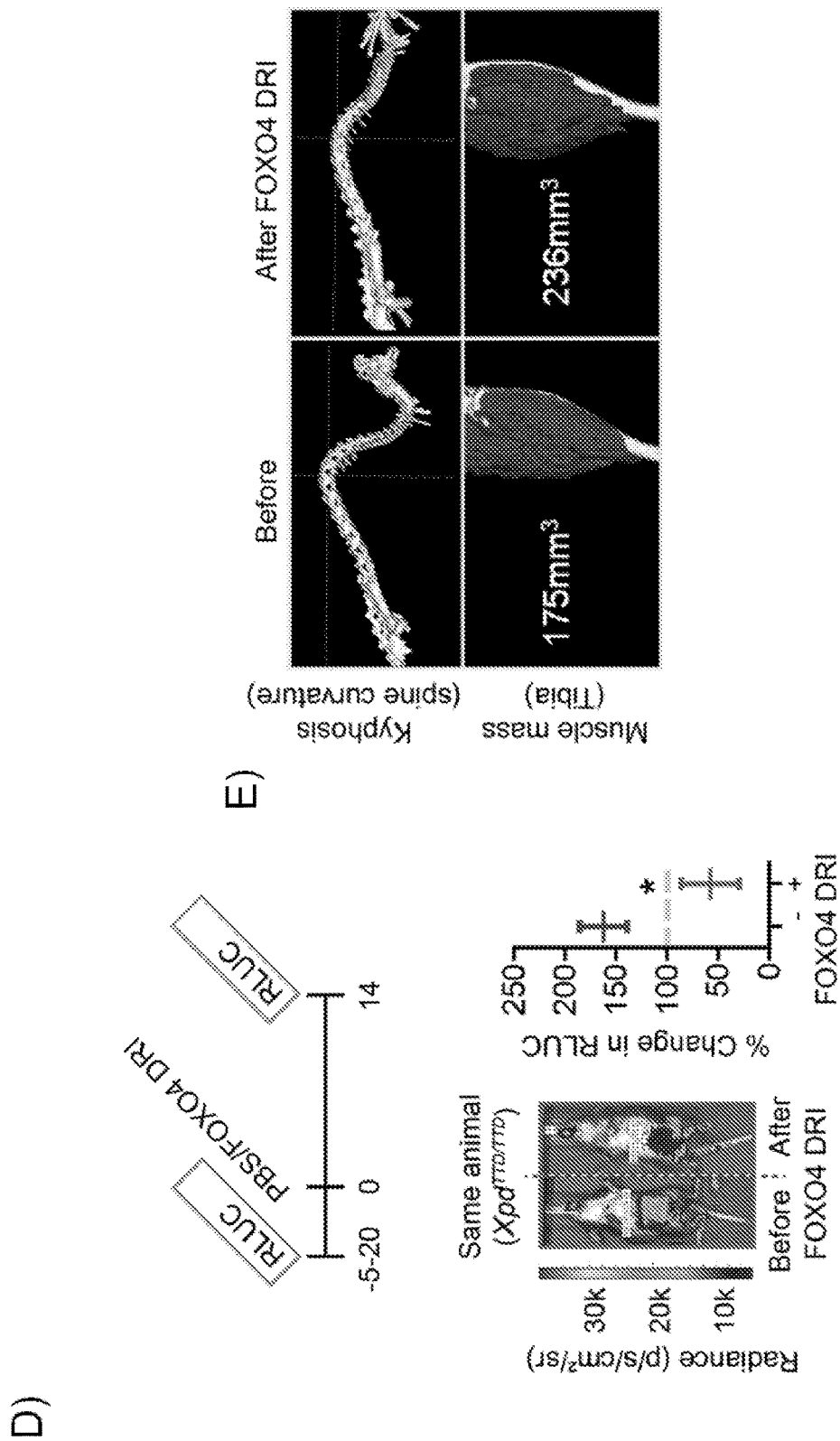
Figure 3:
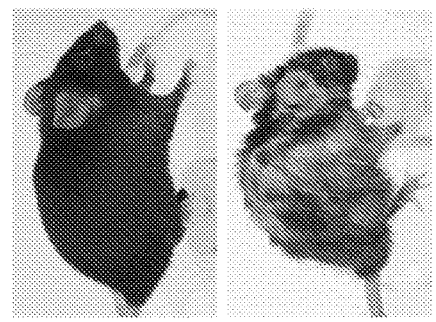
Figure 3:
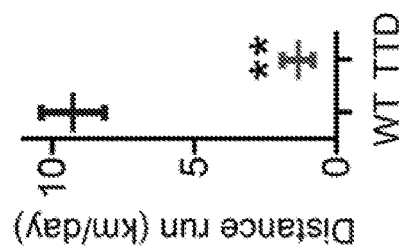
Figure 3:
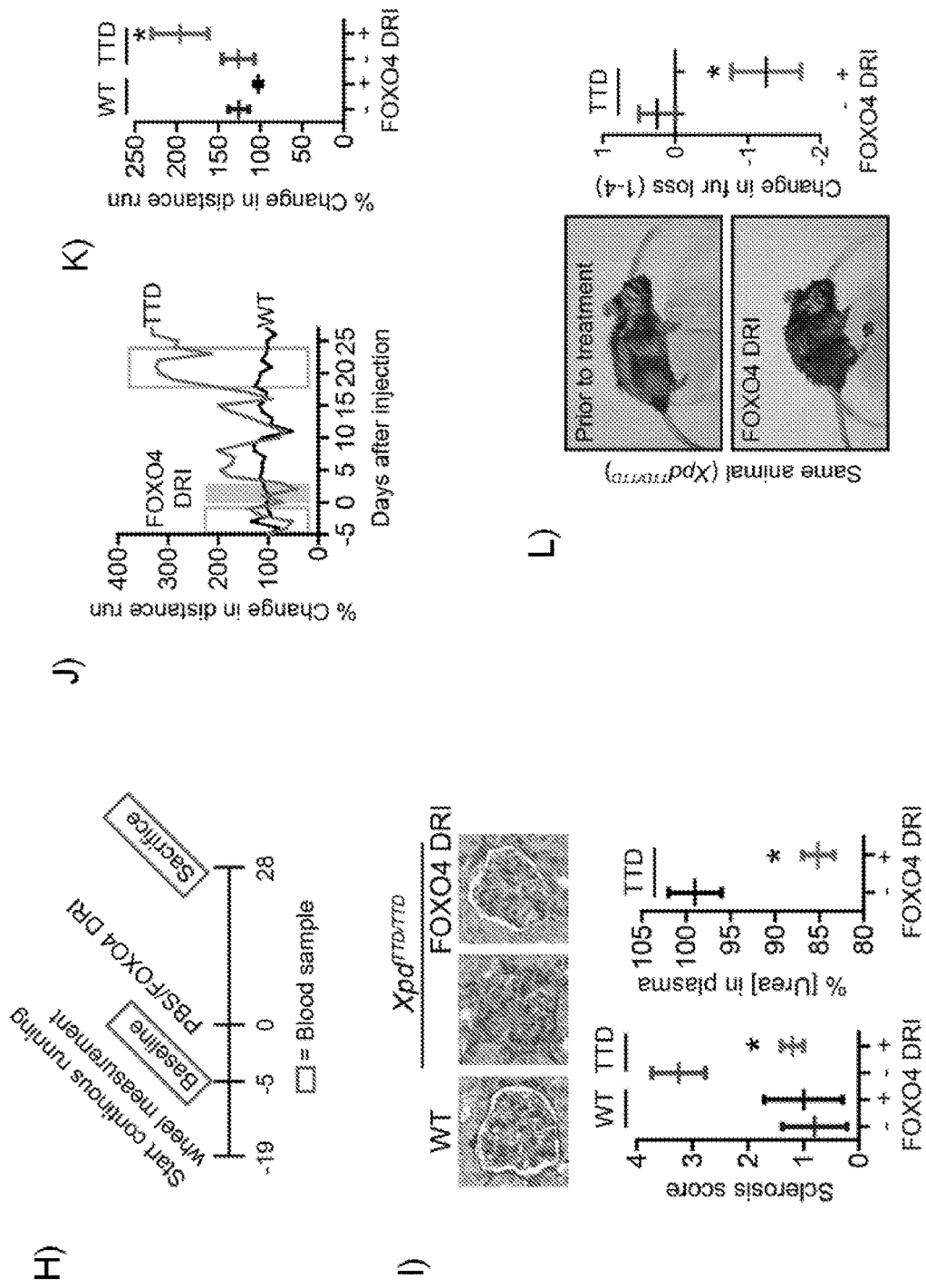
Figure 3:
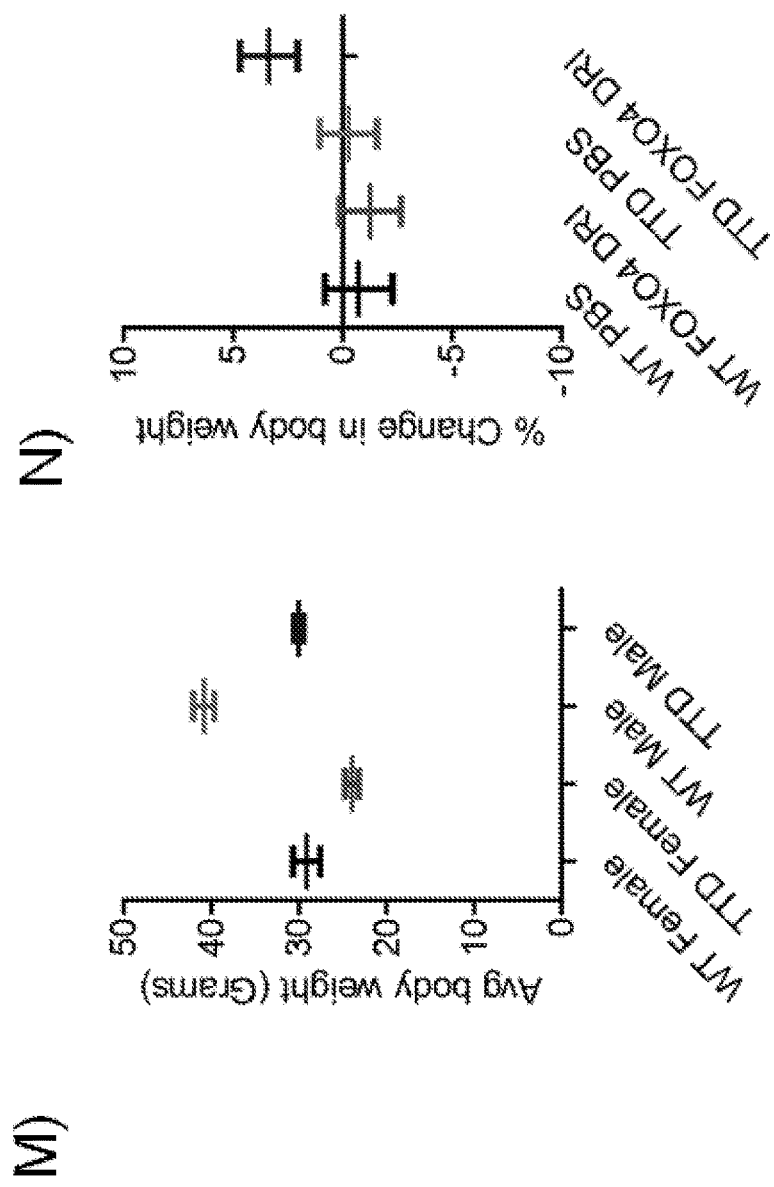
Figure 3:
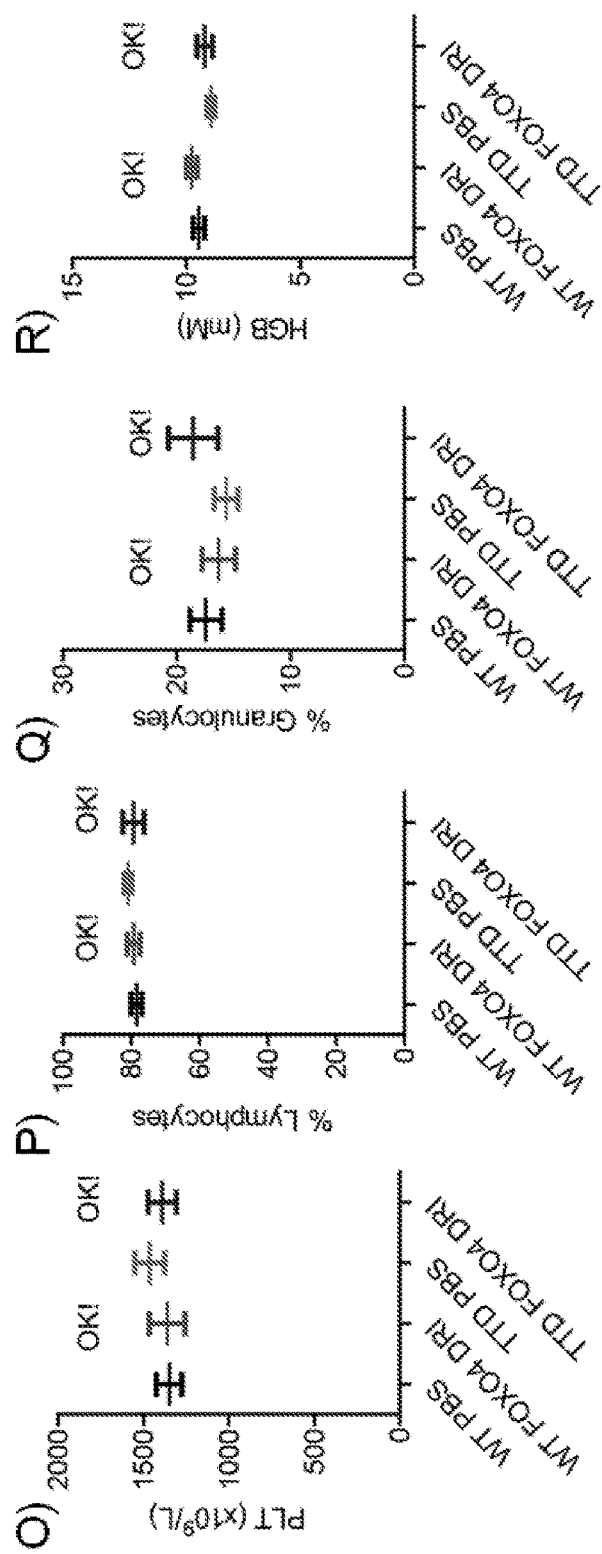

It was unexpectedly found that a peptide according to the invention can induce apoptosis in senescent cells in vitro, while leaving non-senescent cells intact. The inventors even validated their findings in a mouse model which develops cellular senescence at an accelerated rate and exhibits a fast aging phenotype ($Xpd^{TTD/TTD}$ mouse model, mouse model is described inter alfa in WO 2013/152038, e.g. in paragraphs [0135], [0161] and [0244]). In this mouse model, it was shown that age-associated phenotypes such as reduced fitness, hair loss and spine curvature can be countered by administering a peptide according to the invention (FIG. 3). At present, there are no compounds available which, when administered in the form of a therapeutic composition wherein that compound is the only or sole therapeutically active compound, are able to achieve such a therapeutic effect, namely the induction of apoptosis in senescent cells and countering age-associated phenotypes or diseases. Without being bound by theory, it is the believed that a peptide according to the invention exhibits its function by favoring apoptosis instead of cellular senescence by inhibiting the senescence-favoring interaction between FOXO4 and p53 tumor suppressor protein.

Figure 4:
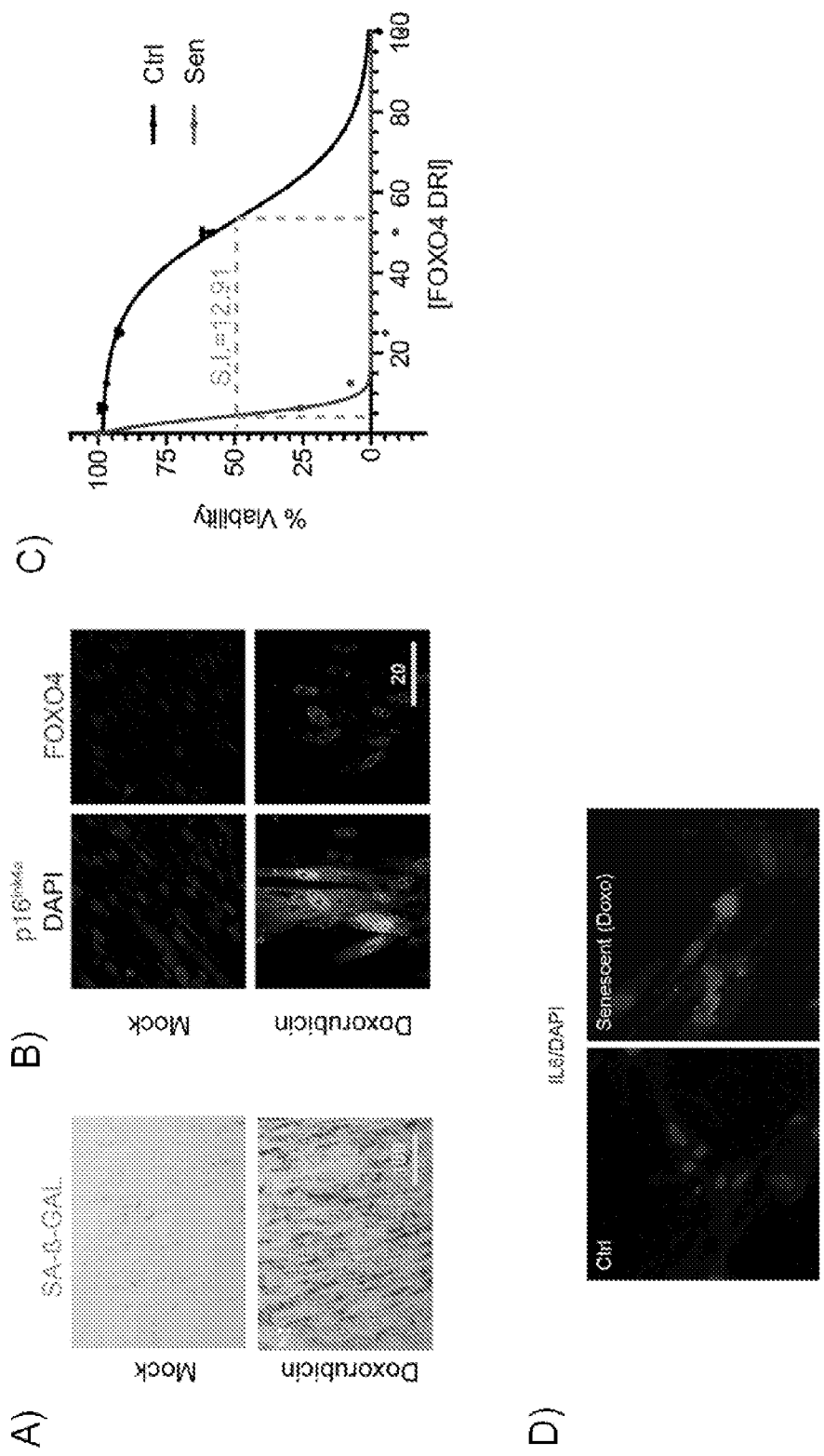
FIG. 4 shows in panel A) that Doxorubicin induces SA-β-GAL expression in IMR90 cells in vitro. IMR90 cells were exposed twice to 0.5 μM Doxorubicin with one day in between. SA-β-GAL activity was determined 7 days later. Panel B) shows that Doxorubicin induces expression of p$16^{ink4a}$ and FOXO4 in IMR90 in vitro. Panel C) shows that FOXO4 DRI selectively reduces viability of Doxorubicininduced senescent cells in vitro. Panel D) shows that Doxorubicin induces IL-6, indicative of elevated SASP. This figure complements FIG. 4A+B by showing that next to the senescence markers SA-β-Gal and p$16^{ink4a}$ also the SASP marker IL-6 is elevated by Doxorubicin. Panel E) shows that doxorubicin induces senescence in vivo. Mice were i.p. injected with 10 mg/kg Doxorubicin and analyzed for RLUC on the indicated time-points. Changes in RLUC intensity for 5 animals are plotted for the indicated timepoints after injection. Panel F) shows a treatment plan for the mice in FIG. 4G. Following one dose of Doxorubicin (10 mg/kg, i.p.) the mice were treated with FOXO4 DRI (n=6; 4×10 mg/kg i.v.) or PBS (n=4; 4× Mock) and processed for RLUC imaging after 14 d. Panel G) shows that FOXO4 DRI lowers Doxorubicin-induced p$16^{ink4a}$-driven RLUC expression indicative of senescence in vivo. Mice treated as indicated in FIG. 4F were analyzed for Bioluminescence. FOXO4 DRItreated animals showed markedly less Doxorubicin-induced p$16^{ink4a}$-positive senescence compared to PBS-treated animals. This shows that, similar to data in FIG. 2 for spontaneous senescence, FOXO4 DRI potently counteracts induced senescence by chemotherapy. H) To improve the window for measuring healthspan changes, the treatment regime from FIG. 4F) was extended with one additional dose of Doxorubicin and milder FOXO4 DRI treatment. Following two doses of Doxorubicin (both 10 mg/kg i.p.) the mice (n=3 each group) were subsequentially treated with PBS or FOXO4 DRI (3×5 mg/kg, 1 d in between) and 14 d later analyzed for changes in healthspan. Panel I) shows that FOXO4 DRI reduces the number of FOXO4 foci after Doxorubicin-treatment in vivo. Post-mortem analysis of liver sections from mice (n=2 each group) treated as in FIG. 4H and stained for FOXO4. The number of FOXO4 foci was objectively quantified using ImageJ. The histogram shows the number of Hepatocytes containing≥FOXO4 foci in 3 sections/liver in duplicate. This shows FOXO4 DRI counters the number of Doxorubicin-induced FOXO4 foci in hepatocytes in vivo. Panel J) shows that FOXO4 DRI reduces IL-6 expression after Doxorubicin-treatment in vivo. Liver sections from the experiment in FIG. 4I were stained for IL-6. This shows FOXO4 DRI counters SASP expression, as marked by IL-6, after Doxorubicin the liver in vivo. Panel K) shows that FOXO4 DRI represses Doxorubicin-induced loss in total body weight. Mice treated as depicted in FIG. 4H (n=9 for PBS, n=11 for FOXO4 DRI) were analyzed for total body weight before and after Doxorubicin-exposure followed by treatment with PBS or FOXO4 DRI. The ratio was plotted. This shows Doxorubicin causes a drop in body weight, an effect neutralized by FOXO4 DRI. Panel L) shows that FOXO4 DRI counteracts Doxorubicin-induced toxicity of the liver (ASAT) and pancreas (Amylase) as determined by blood [plasma]. Experiment as in FIG. 4H. n=3 animals per group. Similar to patients Doxorubicin caused organ toxicity (Miranda et al, 2003, Blood), an effect neutralized by FOXO4 DRI. This shows FOXO4 DRI provides a potent solution to organ toxicity in liver and pancreas upon chemotherapy (Doxorubicin) exposure in vivo.
Figure 4:
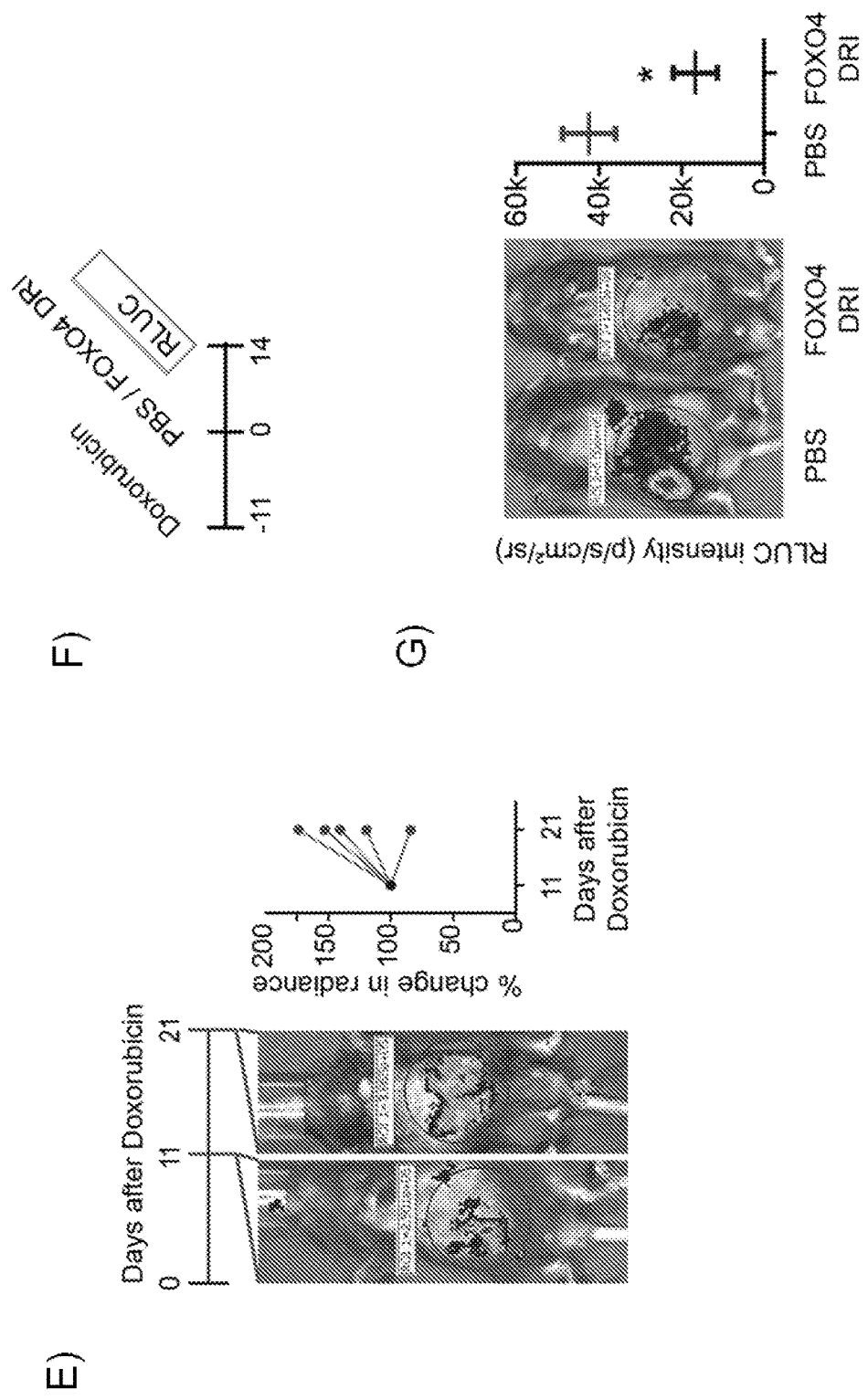
Figure 4:
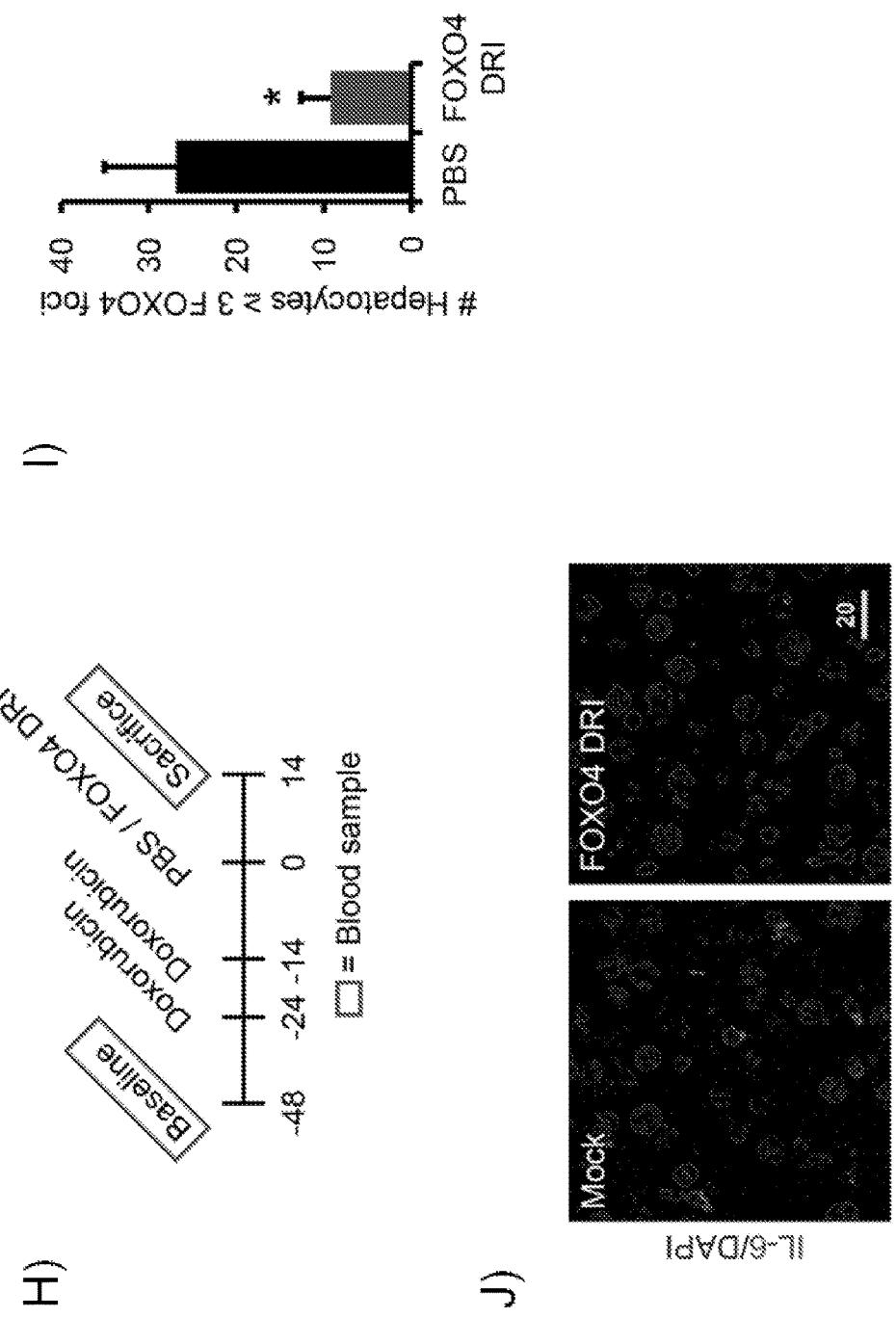
Figure 4:
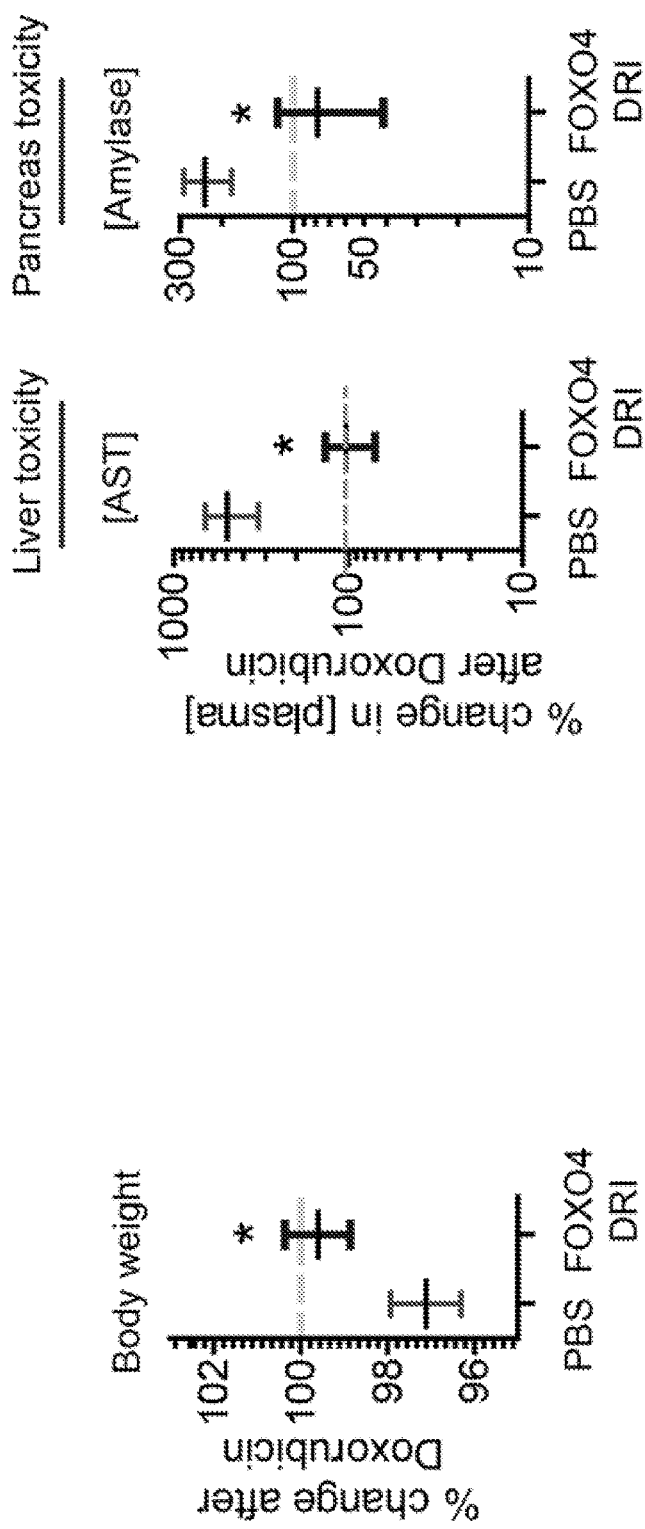

The invention further relates to a pharmaceutical composition comprising a peptide according to the invention. A pharmaceutical composition of the invention may comprise a chemotherapeutic agent such as Doxorubicin. It is advantageous to combine a peptide according to the invention and a chemotherapeutic agent in a pharmaceutical composition, i.e. in a single dosage form. It is established that chemotherapeutic agents induce cellular senescence and peptides according to the invention are capable to selectively clear, kill or reduce the viability of senescent cells. In such a way, off-target effects of chemotherapeutic agents are prevented or counteracted (see FIG. 4). It was further unexpectedly found that a peptide according to the invention can sensitize a resistant cancer to a chemotherapeutic agent. A pharmaceutical composition according to the invention is formulated in a therapeutically effective amount. Preferably, a pharmaceutical composition or peptide according to the invention is in a pharmaceutically acceptable form adapted for administration via a specific route of administration. A pharmaceutical composition or peptide according to the invention is most preferably parenterally administered. Alternatively, the invention relates to a combination preparation comprising a peptide according to the invention and a chemotherapeutic agent for simultaneous or sequential administration.

The invention further provides a nucleic acid comprising a DNA sequence that encodes a peptide of the invention. The person skilled in the art will understand how to generate a DNA sequence that encodes an amino acid sequence of a peptide of the present invention and how to manufacture and isolate a nucleic acid molecule with said DNA sequence using generally known recombinant DNA techniques.

The present invention also provides an expression vector, preferably a viral expression vector comprising a nucleic acid molecule of the invention. It is envisaged herein that the viral expression vector is suitable for use in gene therapy.

It is emphasized that a peptide according to the invention or a pharmaceutical composition according to the invention are for use as a medicament. More preferably, a peptide according to the invention or a pharmaceutical composition according to the invention are for use in the treatment of a disease or condition wherein the removal of senescent cells is beneficial. Alternatively, a peptide according to the invention or a pharmaceutical composition according to the invention are for use in clearing, removing or killing senescent cells. It is envisioned herein that any disease associated with senescent cells having the "senescence associated secretory phenotype (SASP)" in humans, and preferably those having the wildtype p53 tumorsuppressor gene, are sensitive or responsive to treatments as defined herein. The skilled person is well aware of the diseases of which it is known that high levels of SASP factors such as IL1a or IL6 are expressed. It is these diseases that are in particular sensitive or responsive to treatments as defined herein, more in particular having the "SASP" in combination with WT p53.

Alternatively, the invention provides the use of a peptide, pharmaceutical composition or nucleic acid according to the invention for the manufacture of a medicament, preferably a medicament for treating a disease or condition wherein the removal of senescent cells is beneficial.

Preferably, said disease or condition is selected from the group formed by atherosclerosis, chronic inflammatory diseases such as arthritis or athrosis, cancer, osteoarthritis, glomerulosclerosis, diabetes including diabetes type II, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease cataracts, anemia, hypertension, fibrosis, age-related macular degeneration, COPD, asthma, renal insufficiency, reducing or preventing graft failure after organ or tissue transplantation, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness.

Preferably, graft failure after organ or tissue transplantation is reduced or prevented by administering a peptide, composition or nucleic acid of the invention to a donor subject before transplantation of said organ or tissue; or it is reduced or prevented by subjecting a harvested organ or tissue as such to said peptide, composition or nucleic acid of the invention; or it is reduced or prevented by administering a peptide, composition or nucleic acid of the invention to the recipient subject after transplantation of said organ or tissue.

Preferably, a peptide or pharmaceutical composition according to the invention are for use in clearing, removing or killing senescent cells in a human subject suffering from, or expected to suffer from, atherosclerosis, chronic inflammatory diseases such as arthritis or athrosis, cancer, osteoarthritis, diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease cataracts, anemia, hypertension, fibrosis, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness.

Figure 2:
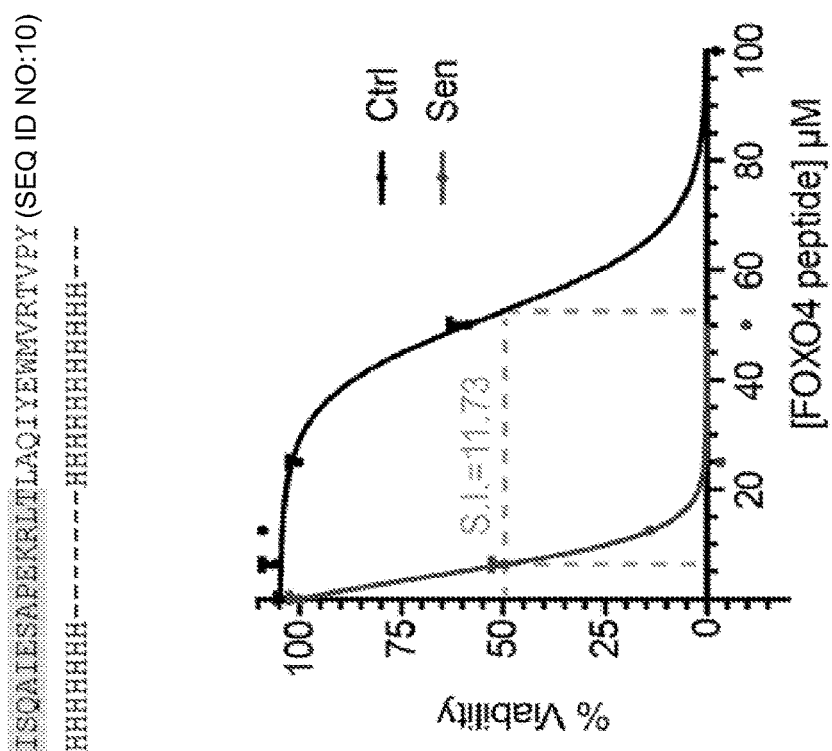
FIG. 2 shows in panels A and B the sequence and 3D structure of FOXO4 (SEQ ID NO:10) used for the design of FOXO4 DRI which has the sequence: of SEQ ID NO:8 (MW: 5358.2), in which all amino acid residues are in the D-isoform, i.e., the FOXO4 DRI peptide is the D-Retro-Inverso isoform of (SEQ ID NO:2), in which all amino acid are in the L-isoform. The amino acids highlighted in A) are shown as small halos in the displayed X-Ray structure of the DNA-binding domain of FOXO4 (3L2C protein databank). The amino acids PRKGGS (SEQ ID NO:9) in A) are not represented in the 3D structure, but are part of the FOXO4 DRI sequence. The large spheres in B) indicate the underlined amino acids from A) that change most upon p53-interaction as identified by NMR. Panel C shows that FOXO4 DRI selectively reduces senescent cell viability. Senescent and control IMR90 were incubated with increasing doses of FOXO4 DRI and cell viability was determined 6 days later using the AQueousOne Solution Cell Proliferation Assay (Promega) according to the manufacturer's protocol. The selectivity index (S.I.) for the EC50 values was determined after non-regression analysis (GraphPad Prism) of the curves. Panel D) shows FOXO4 DRI selectively reduces senescent cell density in time starting at 36 hours after administration. Real-time cell density was measured using an xCELLigence detection system (ACEA Biosciences). Prior to the start of the measurement 50 μL DMEM 10% FCS was added to each well of an E-plate view 16 (Roche) to determine background signal. Non-senescent (2000 cells per well) and senescent (5000 cells/well) IMR90 fibroblasts were then plated in 150 μl medium. 16 hours later the E-plate was placed in the xCELLigence reader and the cell density was recorded every 30 minutes. The cells were treated with 25 uM FOXO4 peptide 8 hours after starting the measurements. Measurements continued for the indicated time-points. Panel E) shows that FOXO4 DRI, but not a peptide of identical amino acid sequence in L-isoform, nor an unrelated FOXM1 DRI peptide (Kruiswijk et al, Oncogene, 2015), selectively eliminates senescent cells in a dose-dependent manner (6.25, 12.5 and 25 μM, respectively). Experiment as in FIG. 2C, but with the indicated peptides. Panel F) shows that FOXO4 DRI (25 μM) selectively induces Caspase-3/7 activation in time in senescent, but not control, IMR90 cells. Cells were plated in 4-well Poly-L-Lysine coated glass bottom 35 mm dishes (D141410; Matsumi, Japan) and incubated with NucView488 Caspase-3 (4440; Essen Bioscience). FOXO4 DRI or PBS was added and the cells were transferred to a Heat and CO2-controlled incubator attached to a LSM510 confocal microscope (Zeiss). 8h after addition the real-time imaging was initiated and every 30 min a grid of 3×3 pictures was imaged. The imaging continued for another 6 days and the images were concatenated using Zen imaging software. Panel G) shows that FOXO4 DRI (25 μM) reduces senescent cell viability through cell-intrinsic apoptosis. Senescent IMR90 cells were incubated with the pan-caspase inhibitors QVD-OPH or ZVAD-FMK (20 μM) and exposed to FOXO4 DRI. After 6 days cell viability was determined as in FIG. 2C). Both QVD-OPH and ZVAD-FMK potently blocked the effect of FOXO4 DRI to reduce senescent cell viability, indicating FOXO4 DRI causes cell death of senescent IMR90 through Caspase-3/7 mediated apoptosis. Panel H) shows that FOXO4 DRI selectively reduces viability of senescent, but not control, normal human cell types: IMR90, BJ and Wi-38. Experiment as in FIG. 2C (12.5 μM FOXO4 DRI). This indicates the effect of FOXO4 DRI on targeting senescent cells holds true for additional cell types. I) Intermittent treatment with low doses of FOXO4 DRI proved better selectivity for killing senescent cells than a single higher dose. Experiment as in FIG. 2C, but according to the indicated treatment plan. Instead of one single dose, three doses were given (one day in between) of ⅓ that concentration each time. The selectivity at the EC75 was higher when 3×⅓ was administered than 1×1. This forms the basis for the in vivo experiments, in which the mice will receive 3× a low dose with one day in between. Panel J) shows that FOXO4 DRI selectively kills cells expressing high levels of SASP proteins. Left: Experiment as in FIG. 2C, but on cells pretreated once daily for two days with IL-1α Receptor Antagonist (RA), which blocks IL-1α/β signaling, recombinant IL-6 and recombinant IL-1α/β. While IL-1RA reduced the effectiveness of FOXO4 DRI (12.5 μM) for killing senescent cells, recombinant IL-1α/β enhanced the effect. Right: Similar experiment as in the left panel, except viability measured one day earlier. The broad range SASP inhibitors Cortisol and Rapamycin and an antibody against IL-1α reduce the effectiveness of FOXO4 DRI in lowering senescent cell viability, while the general inflammation enhancer Lipopolysaccharide (LPS) improves it. Together these two panels demonstrate FOXO4 DRI specifically targets those senescent cells which express high SASP as is the case in many senescence-related diseases in vivo, including TypeII diabetes and obesity. Panel K) shows that FOXO4 DRI causes a decrease in active 15-phosphorylated p53 foci caused by its relocalization to the cytosol. Senescent IMR90 cells, which show elevated foci of active, S15-phosphorylated p53, were plated on coverslips and either mock treated or incubated with 25 µM FOXO4 DRI in the presence of the pan-caspase inhibitor QVD-OPH to prevent dying cells from dethatching from the coverslips. After 3 days the media was replaced with media containing fresh QVD-OPH, but no additional FOXO4 DRI. At day 5 after FOXO4 DRI exposure the cells were fixed and stained for Ser-15-phosphorylated p53 and DAPI to indicate cell nuclei. A significant reduction of Ser15-p53 foci in the nucleus was apparent, which was caused by translocation to the Cytosol by FOXO4 DRI. Panel L) shows that FOXO4 DRI reduces expression of the senescence-associated p53 target p21Cip1. In senescent cells p53 signaling causes upregulation of the cell-cycle arrest and pro-survival protein p21Cip1. Treatment of Senescent cells as in panel K) resulted in a strong reduction of p21Cip1. This indicates that by lowering active pSer15-p53 levels in the nucleus FOXO4 DRI causes a decrease in its activity towards transcription of downstream targets as p21Cip1. Panel M) shows that FOXO4 DRI causes a strong upregulation of a p53 modification associated with apoptosis, pSer46. Experiment as in FIG. 2K. While pSer46 levels are mildly present in senescent cells, FOXO4 DRI causes a strong upregulation of this post translational modification of p53. Thus, FOXO4 DRI not only lowers expression of pro-survival factors as p21Cip1, but also causes an elevation in pro-apoptotic signaling by p53. Panel N) shows that FOXO4 DRI (25 µM) reduces senescent cell viability in a p53-dependent manner. Experiment as in FIG. 2c, but with control and senescent IMR90 stable transduced with shRNAs against p53 or a control shRNA (shGFP). Loss of p53 decreased the potency of FOXO4 DRI for reducing senescent cell viability. Together these data show that FOXO4 DRI selectively kills senescent cells through p53-mediated apoptosis.
Figure 2:
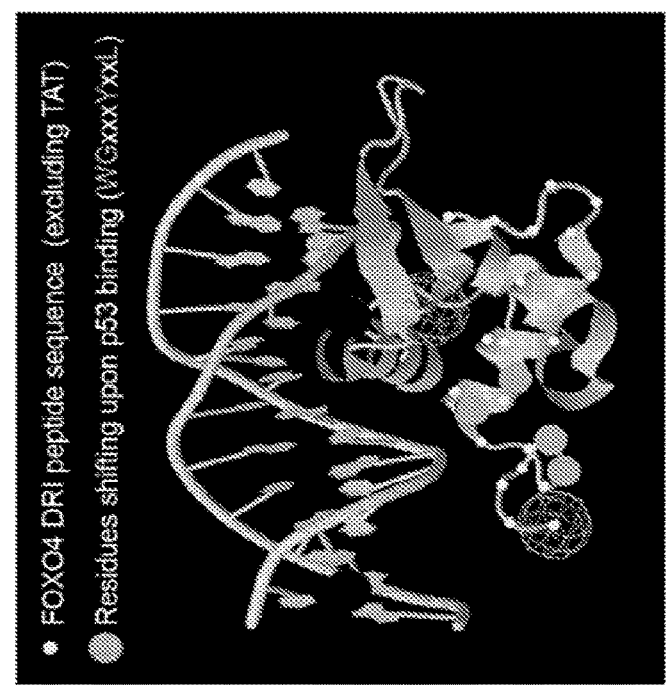
Figure 2:
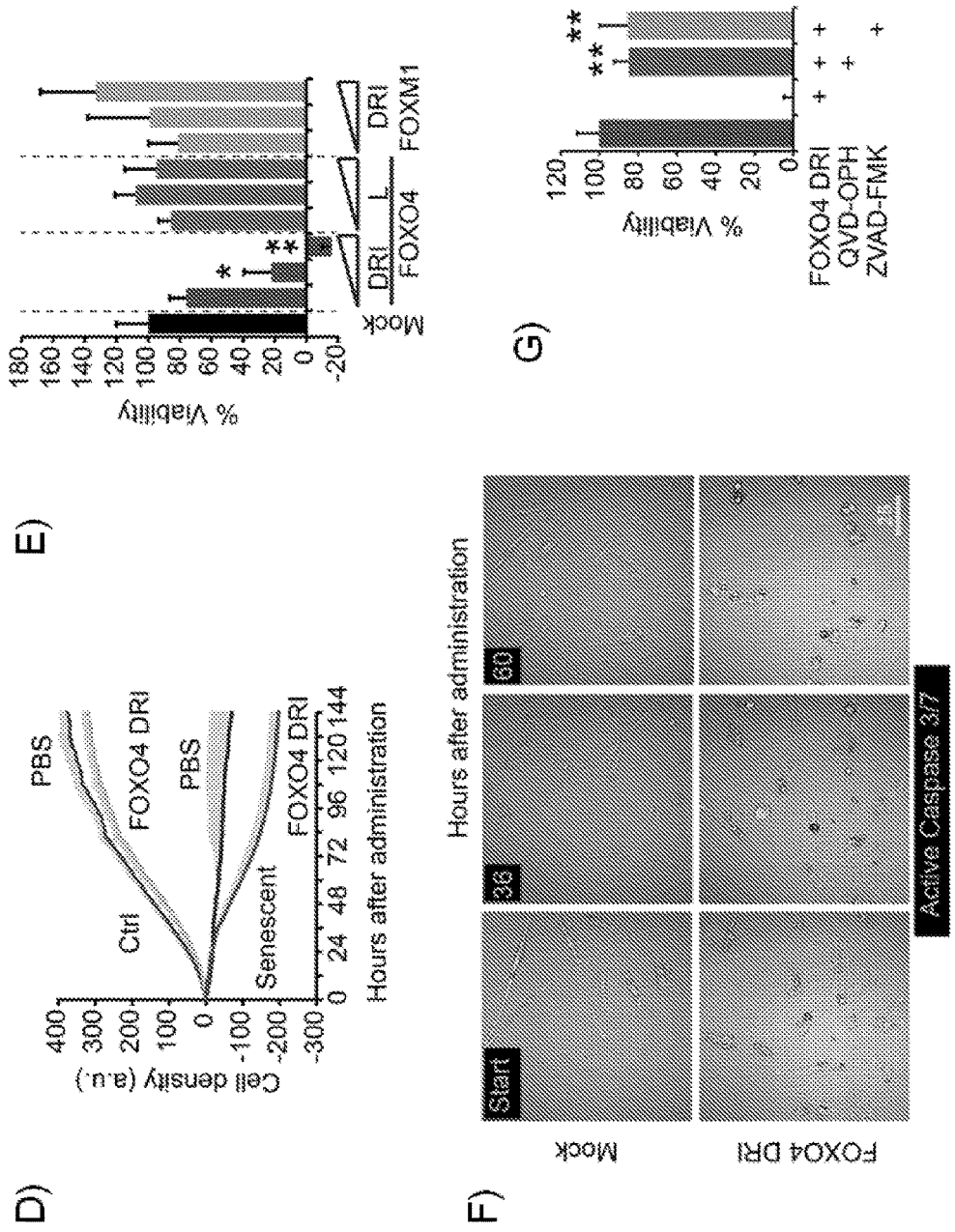
Figure 2:
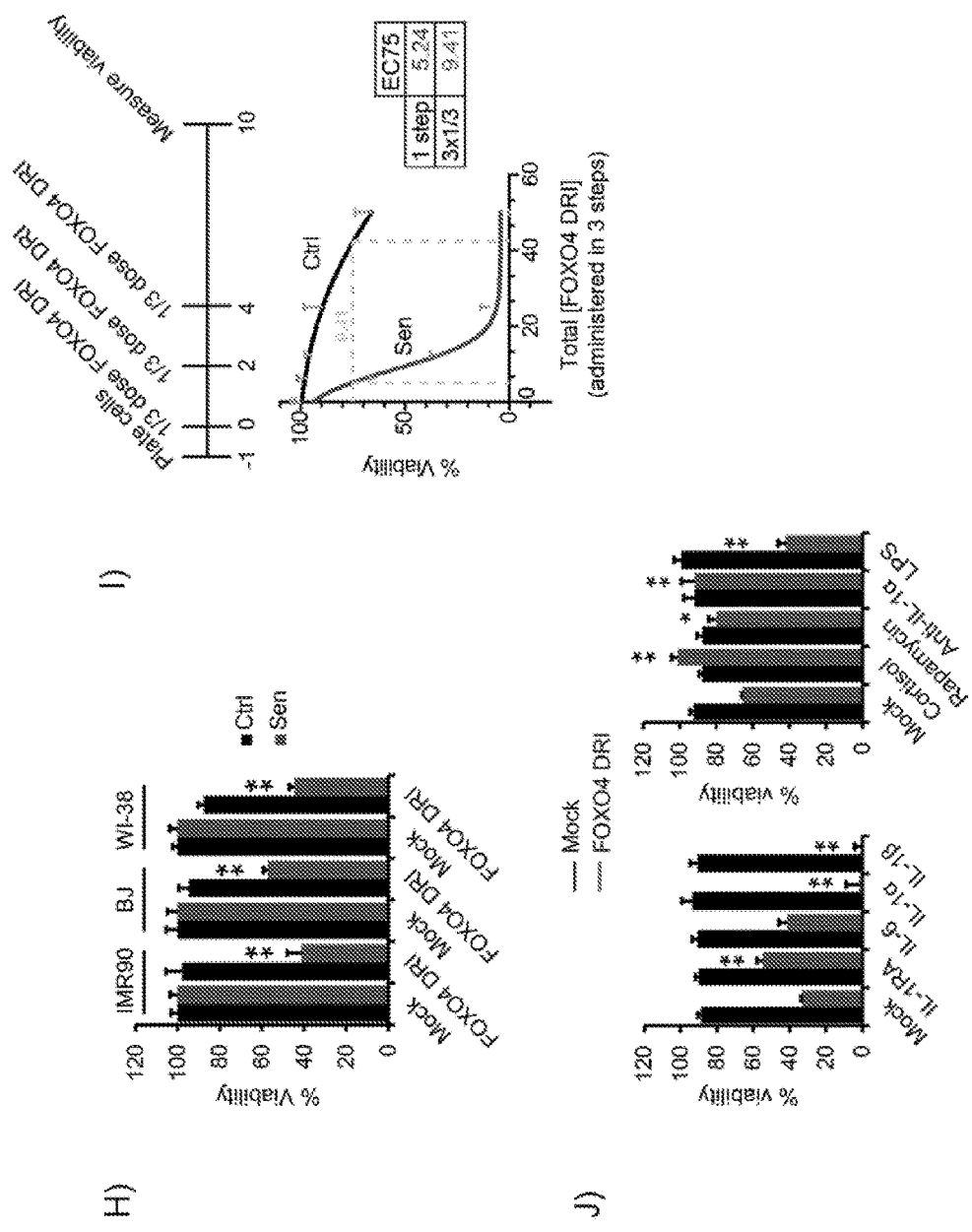
Figure 2:
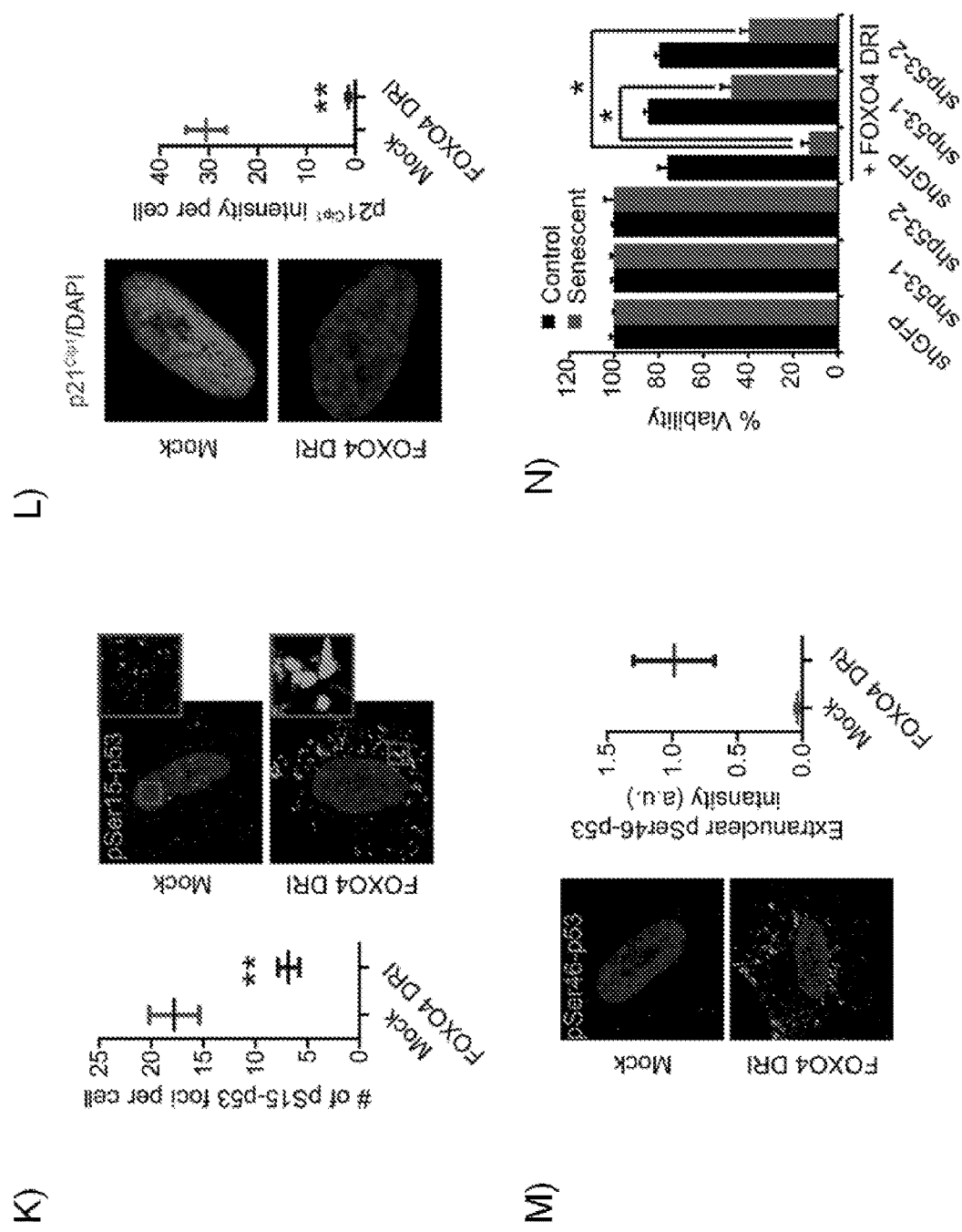

Preferably, a peptide or pharmaceutical composition according to the invention are for use in countering $p21^{cip1}$ expression in a human subject suffering from, or expected to suffer from, atherosclerosis, chronic inflammatory diseases such as arthritis or athrosis, cancer, osteoarthritis, diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease cataracts, anemia, hypertension, fibrosis, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness. Preferably, the $p21^{cip1}$ expression is countered in senescent cells. It is shown in FIG. 2 that a peptide according to the invention counters the expression of $p21^{cip1}$. The human gene $p21^{cip1}$ is also known as cyclin-dependent kinase inhibitor 1A (CDKN1A), or P21, CIP1, SDI1, WAF1, CAP20, CDKN1 or MDA-6 and is indicated with NCBI gene ID no. 1026.

Preferably, a peptide or pharmaceutical composition according to the invention are for use in removing, killing or clearing cells that express $p16^{INK4a}$ in a subject suffering from, or expected to suffer from, atherosclerosis, chronic inflammatory diseases such as arthritis or athrosis, cancer, osteoarthritis, diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease cataracts, anemia, hypertension, fibrosis, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness. It is shown in the Figures that a peptide according to the invention removes, kills or clears cells that express $p16^{INK4a}$. The human $p16^{INK4a}$ gene is also referred to as cyclin-dependent kinase inhibitor 2A and is indicated with NCBI gene ID no. 1029.

Preferably, a peptide or pharmaceutical composition according to the invention are for use in countering, or reducing the number of, nuclear serine-15-phosphorylated p53 foci in a subject suffering, or expected to suffer, from atherosclerosis, chronic inflammatory diseases such as arthritis or athrosis, cancer, osteoarthritis, diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease cataracts, anemia, hypertension, fibrosis, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness.

A peptide or pharmaceutical composition according to the invention is preferably administered consecutively in a single dosage form. More preferably, it is administered daily (once in 12 h or 24 h), for one or more days, preferable consecutive days, such as at least 2, 3, 4, 5, 6, 7, 8, 9, 10, 11, 12, 13 or 14 consecutive days, more preferably 3 consecutive days. Alternatively, said peptide or pharmaceutical composition is administered once weekly. Such a dosage regimen is also applicable to other compounds mentioned in this application, such as an inhibitor for use or a pharmaceutical composition—comprising an inhibitor—according to the invention.

In a preferred embodiment of a peptide or pharmaceutical composition—comprising a peptide according to the invention—for use according to the invention; the disease or condition wherein the removal of senescent cells is beneficial is cancer; and the peptide for use or pharmaceutical composition for use is for administration, preferably as adjuvant, to a mammalian, preferably human, subject before, during and/or after subjecting said subject to radiation therapy and/or before, during or after administering to said subject a chemotherapeutic agent. Preferably, administration of the peptide or pharmaceutical composition—comprising a peptide according to the invention—for use is adapted for clearing, killing or reducing the viability of cells that have become senescent as a result of treatment by radiation therapy or with a chemotherapeutic agent. It was unexpectedly found that a peptide or pharmaceutical composition—comprising a peptide according to the invention—could reduce the off-target effects of current chemotherapeutic agents leading to improved organ function by reducing organ toxicity. Alternatively, it was found that a peptide of the invention has the potential to kill, remove or clear a cancer. Thus, a peptide according to the invention is in one embodiment suitable for use in the treatment of a cancer, preferably a melanoma, breast cancer, prostate cancer or glioblastoma.

Figure 6:
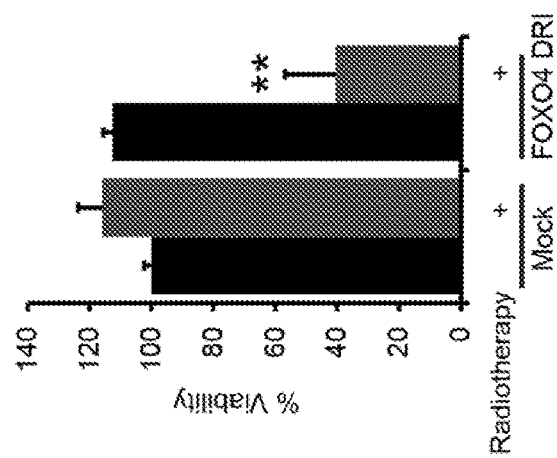
FIG. 6 shows in Panels A+B) that FOXO4 DRI is not only potent against melanoma, but also against breast cancer and Glioblastoma. A) T47D breast cancer cells were incubated with FOXO4 DRI, resulting in a strong loss in viability. B) Radiation-resistant GL261 glioblastoma cells can be resensitized to therapy upon addition of FOXO4 DRI. GL261 cells were irradiated (8Gy), incubated with FOXO4 DRI of exposed to combined treatment. Panel C) shows that FOXO4 DRI potently and selectively induces apoptosis in FAC-surviving MCF7 cells. MCF7cells were treated with FAC. After one week the FAC survivors and the parental MCF7 cells were exposed to a new dose of FAC or the FOXO4 DRI peptide. Apoptosis was determined by Cytochrome C release after 5 days. Note that the FAC pretreated cells were more resistant to FAC than the parental line, but sensitive to FOXO4 DRI. FAC stands for the clinically used breast cancer cocktail comprising 5'FluoroUracil, Doxorubicin (Adriamycin) and Cyclofosfamide. It is generally noted in this context that it is found that FOXO4 expression is (i) increased in invasive breast carcinoma as compared to normal breast tissue and (ii) is increased in metastasized breast cancer as compared to primary site breast cancer. In addition, in the same context recurrence of breast cancer within five years is linked to an increase in FOXO4 expression.
Figure 6:
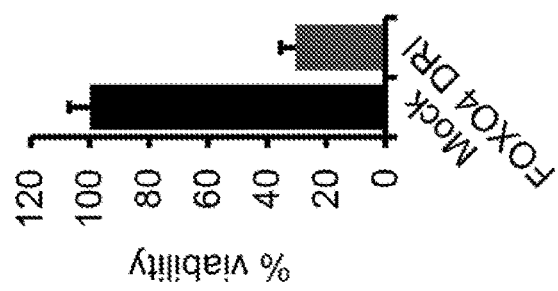
Figure 6:
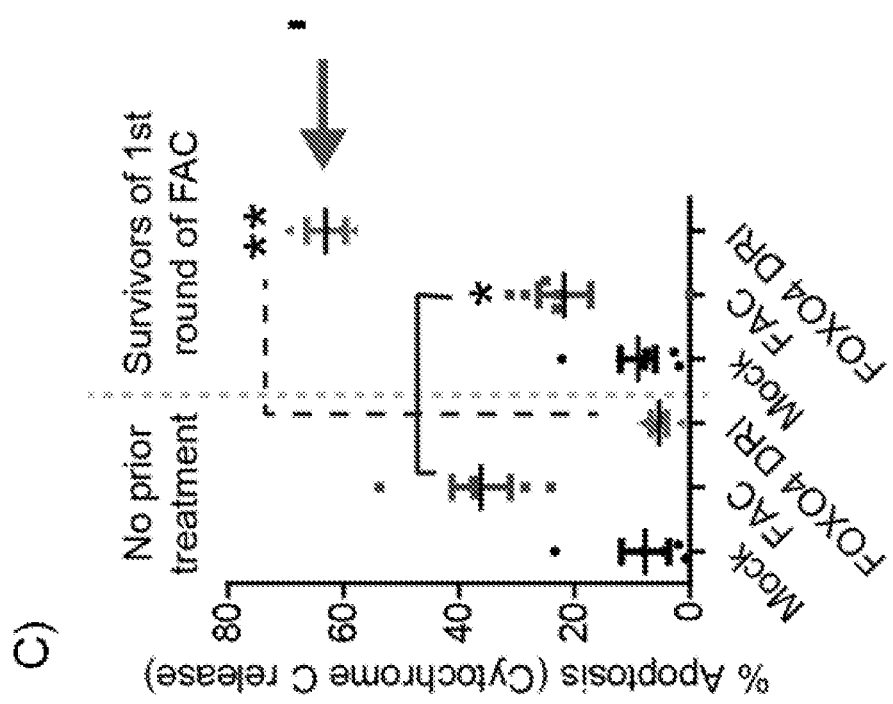
Figure 7:
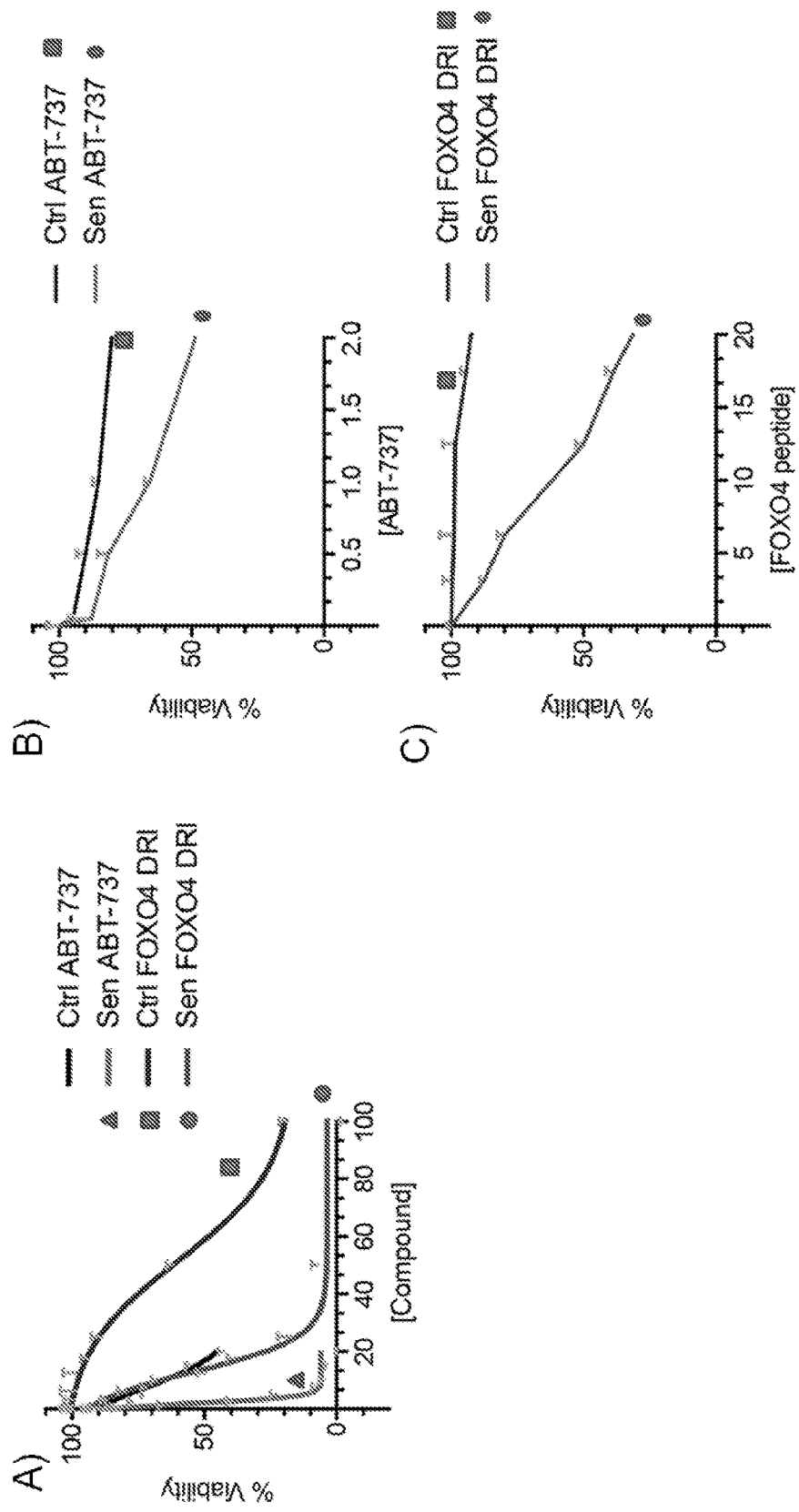
FIG. 7 shows that FOXO4 DRI is safer to non-senescent cells than ABT-737 (an alleged senescent cell clearing compound) and shows higher potential for clearing senescent cells. A) Control IMR90 and IMR90 induced to senesce through 10Gy IR were plated in triplicate for each condition in a 96-well plate. The next day the cells were incubated with the indicated doses of ABT-737 or FOXO4 DRI. After 6 days viability was determined through AqeousOne celltiter assay (Promega) according to the manufacturer's instructions. B) Magnification of the viability of control and senescent IMR90 of A) at lower doses where it shows an effect towards clearing senescent cells. Note that also on control cells ABT-737 shows an effect on viability arguing for toxicity. C) Same as B), but for FOXO4 DRI. Note that FOXO4 DRI shows no toxicity on control cells at doses where it is effective against their senescent counterparts.
Figure 8:
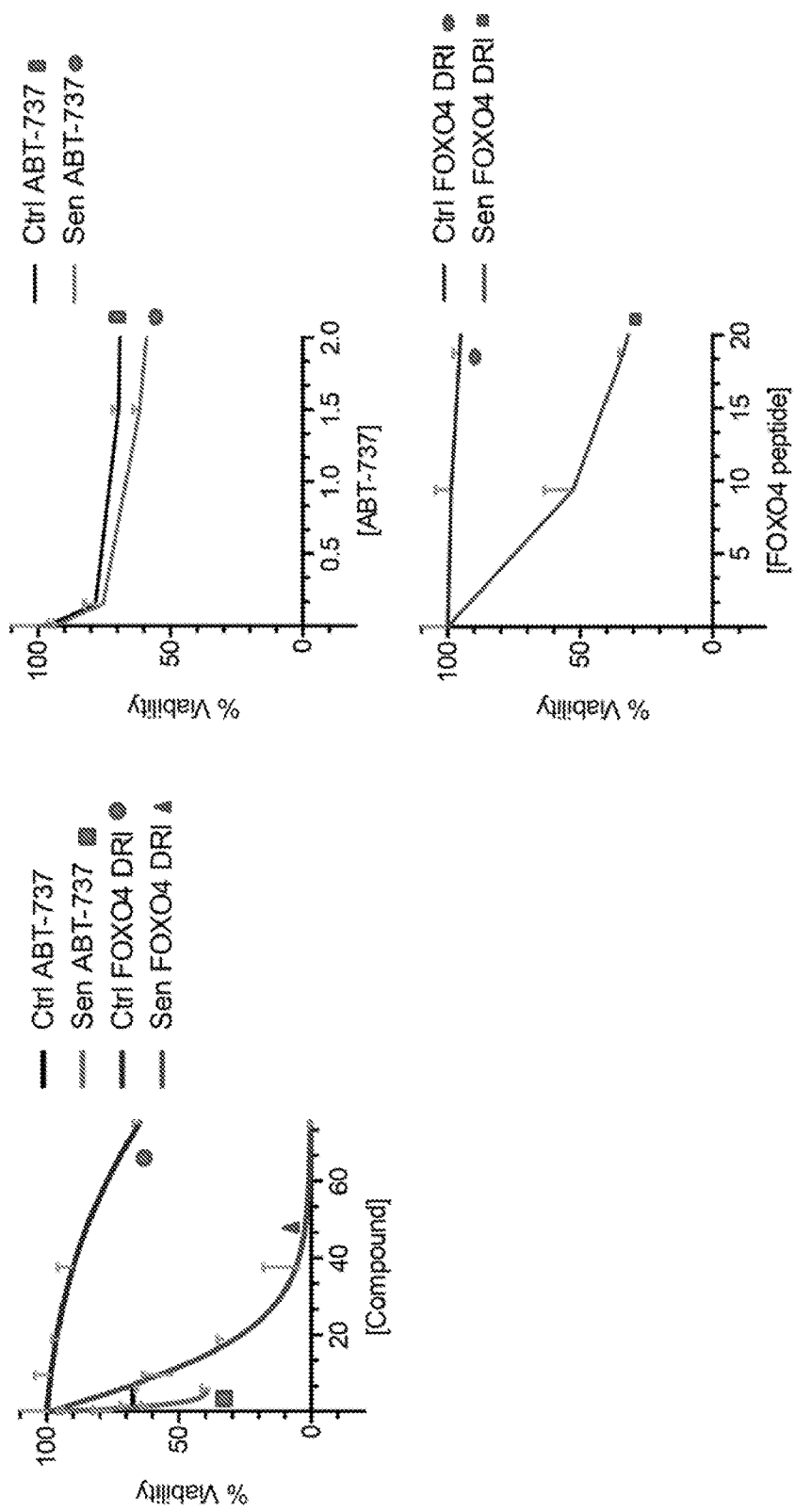
FIG. 8 is the same as FIG. 7), except the compounds were added 3× at ⅓, with 3 days in between. (See also FIG. 10 below for schedule, except there Doxorubicin was used). Also here ABT-737 proved to be toxic to non-senescent cells and only showed limited effectiveness on killing senescent cells, whereas FOXO4 DRI proved to be safe to non-senescent cells and efficient in clearing senescent cells.
Figure 9:
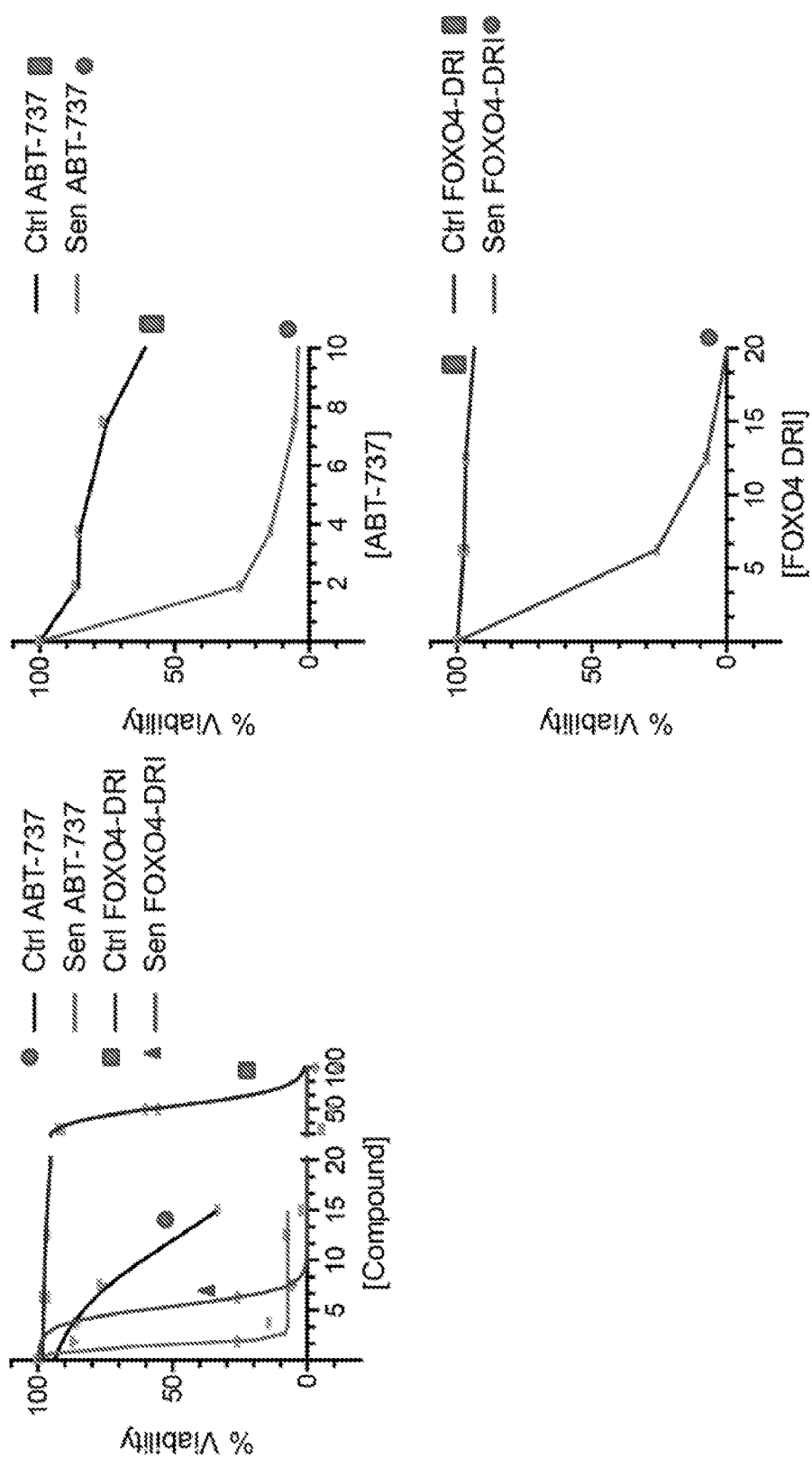
FIG. 9 is the same as FIGS. 7+8, but using IMR90 cells that were induced to senesce through chemotherapy (2×0.5 uM Doxorubicin) instead of IR. The same conclusions apply to FIGS. 7+8.
Figure 10:
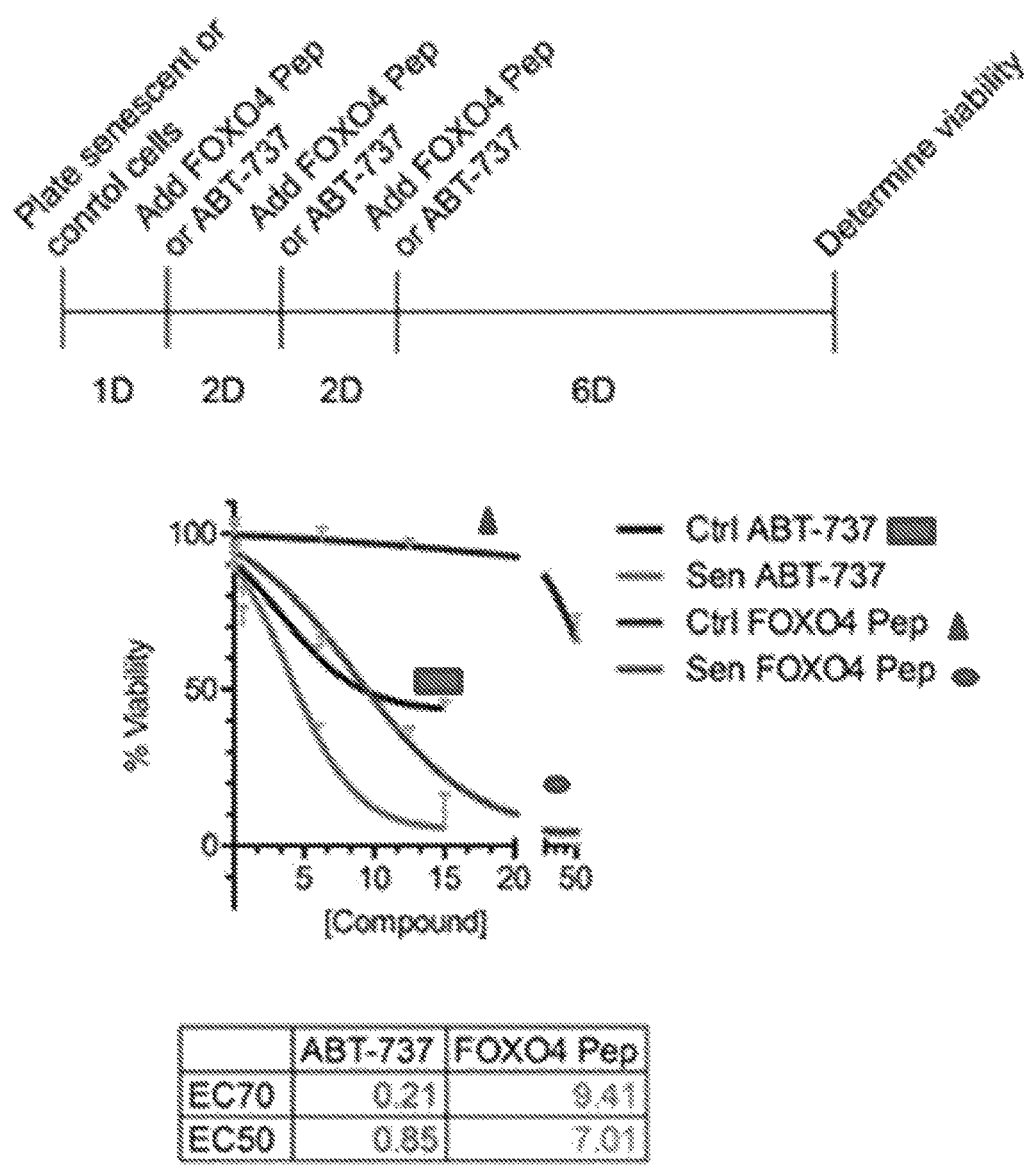
FIG. 10 shows the result of a similar experiment as in FIG. 9, except the cells were treated with 3×⅓ of the indicated doses with 2 d apart. Also for this experiment it is clear that FOXO4 DRI is safe to non-senescent IMR90, whereas ABT-737 lowers their viability already at lower doses. Moreover, FOXO4 DRI shows a high selectivity at EC70 and EC50 for clearing senescent, but not non-senescent cells.
Figure 11:
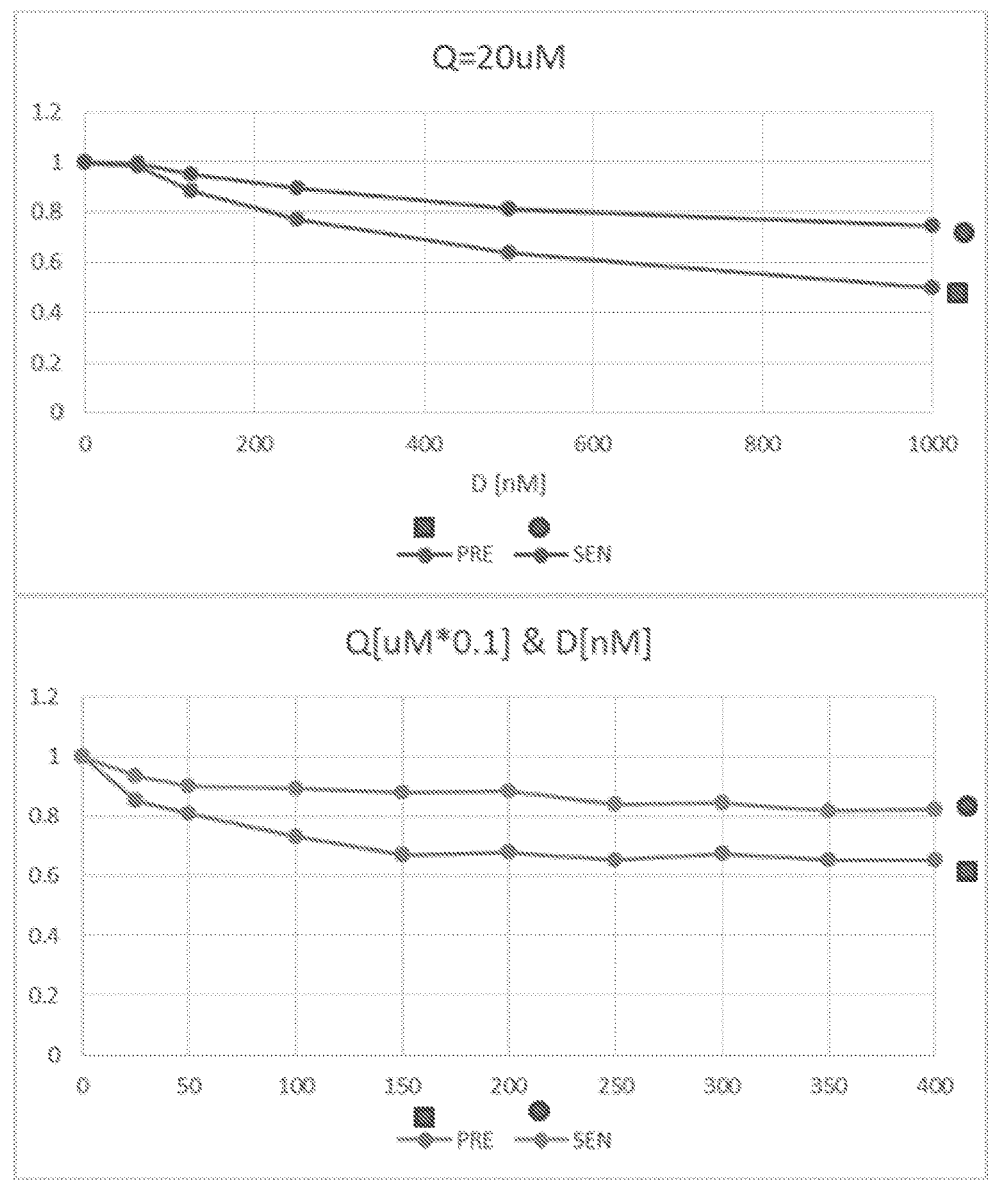
FIG. 11 shows that the reported compounds Quesrcetin and Dasatinib are inefficent towards clearing senescent IMR90. Experiments as in FIG. 7, except the cells were incubated with Quesrcetin alone (Top) for the indicated concentrations, or a combination of 0.1 uM Quesrcetin in addition to the indicated doses of Dasatinib (Bottom). There was no apparent difference in viability of these compounds for killing senescent vs. non-senescent cells.

In the context of the previous paragraph, even more preferred is the situation wherein the cancer is a resistant cancer. Unexpectedly, it was found that a peptide of the invention or pharmaceutical composition—comprising a peptide according to the invention—, could sensitize resistant cancer cells towards a chemotherapeutic agent or radiation therapy that the cancer was previously resistant to (see FIGS. 5 and 6). Preferably, the resistant cancer is metastatic melanoma, breast cancer or glioblastoma, preferably metastatic melanoma or glioblastoma, and the chemotherapeutic agent is a RAF, MEK or ERK inhibitor such as RAF265, trametinib, dabrafenib, selumetinib, vemurafenib and/or trametinib, more preferably vemurafenib and/or trametinib, or agents as disclosed elsewhere herein, alone or in combination; or radation therapy. It was unexpectedly found that a peptide according to the invention can kill, remove or clear a cancer, preferably a resistant cancer, i.e. as a single entity (without the presence of a chemotherapeutic agent). A particular preferred embodiment is thus wherein a peptide according to the invention is for use in the treatment of a cancer, preferably a resistant cancer.

Preferably, a peptide or pharmaceutical composition according to the invention are for use in treating a subject suffering from, or expected to suffer from, kyphosis, scoliosis, sarcopenia, cachexia, sclerosis or renal insufficiency. Alternatively, the peptide or pharmaceutical composition according to the invention are for use in ameliorating or treating at least one symptom of trichothiodystrophy in a subject suffering from, or expected to suffer from trichothiodystrophy. Preferably, the at least one symptom is selected from the group formed by or consisting of kyphosis, hair loss, fitness decline, scoliosis, sarcopenia, cachexia, sclerosis and renal insufficiency.

Further, a peptide or pharmaceutical composition according to the invention are preferably for use in countering or treating chemotherapy-induced weight loss in a subject. Preferably, the weight loss is induced by administration of doxorubicin.

Alternatively, the invention provides a peptide according to the invention for use in sensitizing a resistant cancer in a mammalian, preferably human, subject towards at least one chemotherapeutic agent, preferably at least one chemotherapeutic agent said resistant cancer was or is resistant to. Preferably, said resistant cancer is metastatic melanoma, breast cancer or glioblastoma and said at least one chemotherapeutic agent is a RAF, MEK or ERK inhibitor such as RAF265, trametinib, dabrafenib, selumetinib, vemurafenib and/or trametinib, more preferably vemurafenib and/or trametinib.

Further in the alternative, the invention provides for a peptide according to the invention for use in the treatment of a resistant cancer in a mammalian, preferably human, subject, wherein the peptide is for co-administration with a chemotherapeutic agent, preferably a chemotherapeutic agent said resistant cancer is resistant to.

The invention further relates to a kit comprising a first container containing a peptide according to the invention and a second container containing a chemotherapeutic agent. The kit may suitably contain instructions regarding the administration in a mammalian, preferably human, subject. The human subject is preferably suffering, or suspected to suffer, from cancer, for example a resistant cancer.

A kit according to the invention—comprising a first container containing a peptide according to the invention— is preferably for use in the treatment of cancer in a mammalian, preferably human, subject. Although a peptide of the invention and a chemotherapeutic agent can be formulated in a single dosage form, e.g. a pharmaceutical composition, it is preferably formulated in a multiple dosage form, wherein a peptide of the invention is in one container and a chemotherapeutic agent is in another container. In a kit for use according to the invention, a peptide of the invention and a chemotherapeutic agent are preferably co-administered. Preferably, said peptide is for administration after or following administration of said chemotherapeutic agent. Preferably, a peptide of the invention is administered as adjuvant in such a way that in can clear, kill or reduce the viability of cells that have become senescent as a result of treatment with a chemotherapeutic agent. It was unexpectedly found that a peptide according to the invention can reduce the off-target effects of current chemotherapeutic agents. A kit according to the invention preferably comprises instructions on dosage regimens obtaining an optimal combined effect of a peptide according to the invention and a chemotherapeutic agent.

In another aspect, the invention provides a method of treating a subject suffering, or suspected to suffer, from a disease or condition wherein the removal of senescent cells is beneficial, comprising a) administering a peptide or a pharmaceutical composition according to the invention to a subject suffering, or suspected to suffer, from a disease or condition wherein the removal of senescent cells is beneficial. In a preferred method of the invention, said disease or condition is cancer; further comprises the step of b) administering a chemotherapeutic agent to said subject and/or subjecting said subject to radiation therapy. In another preferred method of the invention, the peptide or the pharmaceutical composition of the invention is administered, preferably as adjuvant, before, during or after administering a chemotherapeutic agent to said subject and/or before, during or after subjecting said subject to radiation therapy. In a more preferred embodiment of any of the methods of the invention described above, wherein said disease or condition is cancer, the cancer is a resistant cancer. In an even more preferred embodiment of any of the methods of the invention described above, wherein said disease or condition is cancer, the cancer is a resistant cancer. In still an even more preferred embodiment of the method described hereinabove, wherein said disease or condition is cancer, the cancer is melanoma, preferably metastatic melanoma, and the chemotherapeutic agent is a RAF, MEK or ERK inhibitor such as RAF265, trametinib, dabrafenib, selumetinib, vemurafenib and/or trametinib, more preferably vemurafenib and/or trametinib.

In another aspect, the invention provides a method of sensitizing a resistant cancer in a mammalian, preferably human, subject to a chemotherapeutic agent to which said cancer is resistant, comprising a) administering a peptide or a pharmaceutical composition of the invention to said subject. In a preferred embodiment of a method of sensitizing a cancer, said resistant cancer is metastatic melanoma, breast cancer or glioblastoma, preferably metastatic melanoma, and the chemotherapeutic agent is a RAF, MEK or ERK inhibitor such as RAF265, trametinib, dabrafenib, selumetinib, vemurafenib and/or trametinib, more preferably vemurafenib and/or trametinib.

In another aspect, the invention provides a method of treating a resistant cancer in a mammalian, preferably human, subject, comprising a) administering a peptide or a pharmaceutical composition according to the invention to a mammalian, preferably human, subject suffering, or suspected to suffer, from a resistant cancer; and b) administering a chemotherapeutic agent, preferably a chemotherapeutic agent said resistant cancer was previously resistant to, to said subject. Said peptide or pharmaceutical composition according to the invention is preferably co-administered with said chemotherapeutic agent. In a preferred embodiment of a method of treating a resistant cancer, the resistant cancer is metastatic melanoma, breast cancer or glioblastoma, preferably metastatic melanoma, and the chemotherapeutic agent is a RAF, MEK or ERK inhibitor such as RAF265, trametinib, dabrafenib, selumetinib, vemurafenib and/or trametinib, more preferably vemurafenib and/or trametinib.

In another aspect, the invention provides a peptide or composition according to the invention for use in countering chemotherapy-induced toxicity, preferably cytotoxicity, in a subject. Preferably, the toxicity is liver toxicity, preferably as determined by assessing ASAT blood plasma levels, or pancreas toxicity, preferably as determined by assessing amylase blood plasma levels. The skilled person is well aware of methods and means for assess liver and pancreas toxicity.

Inhibitors of ASK1

The invention further relates to an inhibitor of ASK1 for use in the treatment of a disease or condition wherein the removal of senescent cells is beneficial. Preferably, an inhibitor of ASK1 inhibits MAP kinase activity of ASK1 in senescent cells. It was unexpectedly found that, when selectively inhibiting the MAP kinase function of ASK1 in senescent cells, apoptosis was induced. An ASK1 inhibitor may thus suitable be used in selectively clearing, killing or reducing the viability of senescent cells (see FIG. 12). Particularly preferred is the ASK1 inhibitor NQDI. Without being bound by theory, it is suggested that ASK1 MAP kinase signaling is important in maintaining cellular senescence and preventing the induction of apoptosis. Alternatively, the invention relates to an inhibitor of ASK1 for use in clearing, removing or killing senescent cells.

Preferably, the disease or condition wherein the removal of senescent cells is beneficial, is selected from the group formed by atherosclerosis, chronic inflammatory diseases such as arthritis or athrosis, cancer, osteoarthritis, diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, sarcopenia, acute myocardial infarction, emphysema, insulin sensitivity, boutonneuse fever, neurodegenerative diseases such as alzheimer's disease or parkinson's disease, Huntington's disease, cataracts, anemia, hypertension, fibrosis, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness. An inhibitor of ASK1 for use according to the invention is preferably administered consecutively in a single dosage form. More preferably, it is administered daily (once in 12 h or 24 h) for one or more days, preferable consecutive days, such as at least three consecutive days. It was found that administration of sequential rounds of NQDI enhances its effectivity towards senescent cell clearance. Alternatively, said inhibitor of ASK1 may be administered in a single dosage form once weekly.

An inhibitor of ASK1 for use according to the invention is formulated in a pharmaceutically acceptable form and in a therapeutically effective amount. Preferably, the inhibitor is in a pharmaceutically acceptable form adapted for administration via a specific route of administration. An inhibitor of ASK1 for use according to the invention is most preferably parenterally administered.

In a preferred embodiment of an inhibitor of ASK1 for use according to the invention; the disease or condition wherein the removal of senescent cells is beneficial is cancer; and the inhibitor of ASK1 is administered or for administration, preferably as adjuvant, to a mammalian, preferably human, subject before, during and/or after subjecting said subject to radiation therapy and/or before, during or after administering to said subject a chemotherapeutic agent. Preferably, administration of the inhibitor of ASK1 for use according to the invention is adapted for clearing, killing or reducing the viability of cells that have become senescent as a result of treatment by radiation therapy or with a chemotherapeutic agent. It was unexpectedly found that an ASK1 inhibitor according to the invention can reduce the off-target effects of current chemotherapeutic agents.

In the context of the previous paragraph, even more preferred is the situation wherein the cancer is a resistant cancer having resistance to a chemotherapeutic agent. More preferably, said resistant cancer is metastatic melanoma, breast cancer or glioblastoma, preferably metastatic melanoma, and said chemotherapeutic agent is a RAF, MEK or ERK inhibitor such as RAF265, trametinib, dabrafenib, selumetinib, vemurafenib and/or trametinib, more preferably vemurafenib and/or trametinib. Alternatively, the invention provides an inhibitor of ASK1, a pharmaceutical composition comprising an inhibitor of ASK1, or a kit for use in medicine—the kit comprising a first container containing an inhibitor of ASK1—, all according to the invention, for use in sensitizing a resistant cancer in a mammalian, preferably human, subject towards at least one chemotherapeutic agent, preferably at least one chemotherapeutic agent said resistant cancer is resistant to. Preferably, said resistant cancer is metastatic melanoma, breast cancer or glioblastoma and said at least one chemotherapeutic agent is a RAF, MEK or ERK inhibitor such as RAF265, trametinib, dabrafenib, selumetinib, vemurafenib and/or trametinib, more preferably vemurafenib and/or trametinib.

Further in the alternative, the invention provides an inhibitor of ASK1, a pharmaceutical composition comprising an inhibitor of ASK1, or a kit for use in medicine—the kit comprising a first container containing an inhibitor of ASK1—, all according to the invention, for use in the treatment of a resistant cancer in a mammalian, preferably human, subject, wherein said inhibitor of ASK1, pharmaceutical composition comprising an inhibitor of ASK1, or kit for use in medicine—the kit comprising a first container containing an inhibitor of ASK1—, is for co-administration with a chemotherapeutic agent, preferably a chemotherapeutic agent said resistant cancer is resistant to.

The invention further relates to a pharmaceutical composition comprising an inhibitor of ASK1, preferably NQDI, and a chemotherapeutic agent. A pharmaceutical composition according to the invention is formulated in a therapeutically effective amount. Preferably, a pharmaceutical composition according to the invention is in a pharmaceutically acceptable form adapted for administration via a specific route of administration. A pharmaceutical composition according to the invention is most preferably parenterally administered. It is advantageous to combine an inhibitor of ASK1 and a chemotherapeutic agent in a single dosage form, since the inhibitor of ASK1 alleviates the off-target effects of a chemotherapeutic agent. A pharmaceutical composition according to the invention is preferably for use in the treatment of a cancer, preferably a resistant cancer. A pharmaceutical composition according to the invention is preferably administered consecutively in a single dosage form. More preferably, it is administered daily, once in 24 h, for one or more days, preferable consecutive days, such as at least 2, 3, 4, 5, 6, 7, 8, 9, 10, 11, 12, 13 or 14 consecutive days, preferably at least three consecutive days. It was found that administration of sequential rounds of NQDI enhances its effectivity towards senescent cell clearance. Alternatively, said inhibitor of ASK1 may be administered in a single dosage form once weekly. Alternatively, the invention relates to a combination preparation comprising an ASK1 inhibitor and a chemotherapeutic agent for simultaneous or sequential administration.

The invention also relates to a kit for use in medicine, the kit comprising a first container containing an inhibitor of ASK1, preferably NQDI, and a second container containing a chemotherapeutic agent. The kit may suitably contain instructions regarding the administration in a mammalian, preferably human, subject. The human subject is preferably suffering, or suspected to suffer, from cancer.

In a preferred embodiment, said kit is for use in the treatment of cancer, preferably a resistant cancer. An inhibitor of ASK1 and a chemotherapeutic agent are preferably formulated in a multiple dosage form, wherein an inhibitor of ASK1 is in one container and a chemotherapeutic agent is in another container. In a kit for use according to the invention, an inhibitor of ASK1 and a chemotherapeutic agent are preferably co-administered. Preferably, an inhibitor of ASK1 according to the invention is administered as adjuvant in such a way that in can clear, kill or reduce the viability of cells that have become senescent as a result of treatment with a chemotherapeutic agent. A kit according to the invention preferably comprises instructions on dosage regimens obtaining an optimal combined effect of an inhibitor of ASK1 and a chemotherapeutic agent.

In another aspect, the invention relates to a method of treating a subject suffering, or suspected to suffer, from a disease or condition wherein the removal of senescent cells is beneficial, comprising a) administering an inhibitor of ASK1, preferable NQDI, to a subject suffering, or suspected to suffer, from a disease or condition wherein the removal of senescent cells is beneficial. In a preferred method of the invention, said disease or condition is cancer, and further comprises the step of b) administering a chemotherapeutic agent to said subject and/or subjecting said subject to radiation therapy. In another preferred method of the invention, the inhibitor of ASK1 is administered, preferably as adjuvant, before, during or after administering a chemotherapeutic agent to said subject and/or before, during or after subjecting said subject to radiation therapy. In a more preferred embodiment of a method of the invention as described above, wherein said disease or condition is cancer, the cancer is a resistant cancer having resistance to said chemotherapeutic agent. In an even more preferred embodiment of a method of the invention as described hereinabove, wherein said disease or condition is a resistant cancer, the resistant cancer is metastatic melanoma, breast cancer or glioblastoma, preferably metastatic melanoma, and the chemotherapeutic agent is a RAF, MEK or ERK inhibitor such as RAF265, trametinib, dabrafenib, selumetinib, vemurafenib and/or trametinib, more preferably vemurafenib and/or trametinib.

In another aspect, the invention provides a method of sensitizing a resistant cancer in a mammalian, preferably human, subject to a chemotherapeutic agent to which said cancer was or is resistant, comprising a) administering an inhibitor of ASK1 to said subject. In a preferred embodiment of a method of sensitizing a cancer, the resistant cancer is metastatic melanoma, breast cancer or glioblastoma, preferably metastatic melanoma, and the chemotherapeutic agent is a RAF, MEK or ERK inhibitor such as RAF265, trametinib, dabrafenib, selumetinib, vemurafenib and/or trametinib, more preferably vemurafenib and/or trametinib.

In another aspect, the invention provides a method of treating a resistant cancer in a mammalian, preferably human, subject, comprising a) administering an inhibitor of ASK1 to a mammalian, preferably human, subject suffering, or suspected to suffer, from a resistant cancer; and b) administering a chemotherapeutic agent, preferably a chemotherapeutic agent said resistant cancer is resistant to, to said subject. Said inhibitor of ASK1 is preferably co-administered with said chemotherapeutic agent. In a preferred embodiment of a method of treating a resistant cancer, the resistant cancer is metastatic melanoma, breast cancer or glioblastoma, preferably metastatic melanoma, and the chemotherapeutic agent is a RAF, MEK or ERK inhibitor such as RAF265, trametinib, dabrafenib, selumetinib, vemurafenib and/or trametinib, more preferably vemurafenib and/or trametinib.

Inhibitors of SYK

The invention further relates to an inhibitor of SYK for use in the treatment of a disease or condition wherein the removal of senescent cells is beneficial; and wherein said disease or condition is not asthma, immune thrombocytopenia, hemolytic anemia, myeloid leukemia and/or lymphoma, preferably wherein said disease or condition is not asthma, immune thrombocytopenia, anemia, leukemia and/or lymphoma, more preferably wherein said disease or condition is not a lung disease, a bleeding disorder, leukemia and/or lymphoma. Alternatively, the invention further relates to an inhibitor of SYK for use in removing, clearing or killing senescent cells. Preferably, an inhibitor of SYK inhibits tyrosine kinase activity of SYK in senescent cells. It was unexpectedly found that, when selectively inhibiting the tyrosine kinase function of SYK in senescent cells, apoptosis was induced. A SYK inhibitor may thus suitable be used in selectively clearing, killing or reducing the viability of senescent cells (see FIG. 13). Particularly preferred is the SYK inhibitor R406. Without being bound by theory, it is suggested that SYK tyrosine kinase signaling is important in maintaining cellular senescence and preventing the induction of apoptosis.

Alternatively, the invention relates to an inhibitor of SYK for use in the treatment of atherosclerosis, chronic inflammatory diseases such as arthritisor athrosis, diabetes, diabetic ulcers, kyphosis, scoleosis, hepatic insufficiency, cirrhosis, Hutchinson-Gilford progeria syndrome (HGPS), laminopaties, osteoporosis, osteoarthritis, dementia, (cardio) vascular diseases, obesity, metabolic syndrome, acute myocardial infarction, emphysema, insulin sensitivity, boutonneuse fever, neurodegenerative diseases such as alzheimer's disease or parkinson's disease, Huntington's disease, cataracts, sarcopenia, hypertension, fibrosis, age-related macular degeneration, COPD, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty, reduced fitness and/or cancer selected from the group formed by adrenocortical carcinoma, anal cancer, appendix cancer, astrocytomas, basal cell carcinoma, bile duct cancer, bladder cancer, bone cancer, brain stem glioma, brain tumor, breast cancer, bronchial tumors, carcinoid tumor, cardiac (heart) tumors, central nervous system tumor, cervical cancer, chordoma, colon cancer, colorectal cancer, craniopharyngioma, ductal carcinoma, embryonal tumors, endometrial cancer, ependymoma, esophageal cancer, esthesioneuroblastoma, ewing sarcoma, extracranial germ cell tumor, extragonadal germ cell tumor, extrahepatic bile duct cancer, eye cancer, fallopian tube cancer, gallbladder cancer, gastric (stomach) cancer, gastrointestinal carcinoid tumor, germ cell tumor, head and neck cancer, hepatocellular (liver) cancer, hypopharyngeal cancer, kidney cancer, lung cancer, lip and oral cavity cancer, male breast cancer, metastatic squamous neck cancer, mouth cancer, nasal cavity and paranasal sinus cancer, ovarian cancer, pancreatic cancer, parathyroid cancer, penile cancer, prostate cancer, rectal cancer, salivary gland cancer, skin cancer, small intestine cancer, stomach (gastric) cancer, thyroid cancer, urethral cancer, vaginal cancer, and/or vulvar cancer. In the above listing of diseases, lymphomas and leukemias are explicitly excluded.

An inhibitor of SYK for use according to the invention is formulated in a pharmaceutically acceptable form and in a therapeutically effective amount. Preferably, the inhibitor is in a pharmaceutically acceptable form adapted for administration via a specific route of administration. An inhibitor of SYK for use according to the invention is most preferably parenterally administered. An inhibitor of SYK is preferably administered daily, once in 12 h or 24 h, for one or more days, preferable consecutive days, such as at least 2, 3, 4, 5, 6, 7, 8, 9, 10, 11, 12, 13 or 14 consecutive days, preferably at least three consecutive days. Alternatively, said inhibitor of SYK may be administered in a single dosage form once weekly.

In a preferred embodiment of an inhibitor of SYK for use according to the invention; the disease or condition wherein the removal of senescent cells is beneficial is cancer; and the inhibitor of SYK is administered or for administration, preferably as adjuvant, to a mammalian, preferably human, subject before, during and/or after subjecting said subject to radiation therapy and/or before, during or after administering to said subject a chemotherapeutic agent; and wherein the cancer is not a lymphoma or myloid leukemia, preferably leukemia; or wherein the cancer is selected from the group formed by adrenocortical carcinoma, anal cancer, appendix cancer, astrocytomas, basal cell carcinoma, bile duct cancer, bladder cancer, bone cancer, brain stem glioma, brain tumor, breast cancer, bronchial tumors, carcinoid tumor, cardiac (heart) tumors, central nervous system tumor, cervical cancer, chordoma, colon cancer, colorectal cancer, craniopharyngioma, ductal carcinoma, embryonal tumors, endometrial cancer, ependymoma, esophageal cancer, esthesioneuroblastoma, ewing sarcoma, extracranial germ cell tumor, extragonadal germ cell tumor, extrahepatic bile duct cancer, eye cancer, fallopian tube cancer, gallbladder cancer, gastric (stomach) cancer, gastrointestinal carcinoid tumor, germ cell tumor, head and neck cancer, hepatocellular (liver) cancer, hypopharyngeal cancer, kidney cancer, lung cancer, lip and oral cavity cancer, male breast cancer, metastatic squamous neck cancer, mouth cancer, nasal cavity and paranasal sinus cancer, ovarian cancer, pancreatic cancer, parathyroid cancer, penile cancer, prostate cancer, rectal cancer, salivary gland cancer, skin cancer, small intestine cancer, stomach (gastric) cancer, thyroid cancer, urethral cancer, vaginal cancer, and/or vulvar cancer. In the aforementioned selection of cancers, lymphomas and leukemias are intended not to be present.

In the context of the previous paragraph, even more preferred is the situation wherein the cancer is a resistant cancer having resistance to a chemotherapeutic agent. More preferably, the resistant cancer is metastatic melanoma, breast cancer or glioblastoma, preferably metastatic melanoma, and the chemotherapeutic agent is a RAF, MEK or ERK inhibitor such as RAF265, trametinib, dabrafenib, selumetinib, vemurafenib and/or trametinib, more preferably vemurafenib and/or trametinib.

Preferably, administration of the inhibitor of SYK for use according to the invention is adapted for clearing, killing or reducing the viability of cells that have become senescent as a result of treatment by radiation therapy or with a chemotherapeutic agent. It was unexpectedly found that a SYK inhibitor according to the invention can reduce the off-target effects of current chemotherapeutic agents.

Alternatively, the invention provides an inhibitor of SYK, a pharmaceutical composition comprising an inhibitor of SYK, or a kit for use in medicine—the kit comprising a first container containing an inhibitor of SYK—, all according to the invention, for use in sensitizing a resistant cancer in a mammalian, preferably human, subject towards at least one chemotherapeutic agent, preferably at least one chemotherapeutic agent said resistant cancer was or is resistant to. Preferably, said resistant cancer is metastatic melanoma, breast cancer or glioblastoma and said at least one chemotherapeutic agent is a RAF, MEK or ERK inhibitor such as RAF265, trametinib, dabrafenib, selumetinib, vemurafenib and/or trametinib, more preferably vemurafenib and/or trametinib.

Further in the alternative, the invention provides an inhibitor of SYK, a pharmaceutical composition comprising an inhibitor of SYK, or a kit for use in medicine—the kit comprising a first container containing an inhibitor of SYK—, all according to the invention, for use in the treatment of a resistant cancer in a mammalian, preferably human, subject, wherein said inhibitor of SYK, pharmaceutical composition comprising an inhibitor of SYK, or kit for use in medicine—the kit comprising a first container containing an inhibitor of SYK—, is for co-administration with a chemotherapeutic agent, preferably a chemotherapeutic agent said resistant cancer is or was resistant to.

The invention further relates to a pharmaceutical composition comprising an inhibitor of SYK, preferably R406, and a chemotherapeutic agent. A pharmaceutical composition according to the invention is formulated in a therapeutically effective amount. Preferably, a pharmaceutical composition according to the invention is in a pharmaceutically acceptable form adapted for administration via a specific route of administration. A pharmaceutical composition according to the invention is most preferably parenterally administered. It is advantageous to combine an inhibitor of SYK and a chemotherapeutic agent in a single dosage form, since the inhibitor of SYK alleviates the off-target effects of a chemotherapeutic agent. A pharmaceutical composition according to the invention is preferably for use in the treatment of cancer. A pharmaceutical composition according to the invention is preferably administered consecutively in a single dosage form. Preferably, it is administered daily, once in 12 h or 24 h, for one or more days, preferable consecutive days, such as at least 2, 3, 4, 5, 6, 7, 8, 9, 10, 11, 12, 13 or 14 consecutive days, preferably at least four consecutive days. Alternatively, said inhibitor of SYK may be administered in a single dosage form once weekly.

Alternatively, the invention relates to a combination preparation comprising an inhibitor of SYK and a chemotherapeutic agent for simultaneous or sequential administration.

The invention also relates to a kit for use in medicine, the kit comprising a first container containing an inhibitor of SYK, preferably R406, and a second container containing a chemotherapeutic agent. The kit may suitably contain instructions regarding the administration in a mammalian, preferably human, subject. The human subject is preferably suffering, or suspected to suffer, from cancer. Preferably, the kit is not for use in the treatment of myeloid leukemia and/or lymphoma.

A kit according to the invention is preferably for use in the treatment of cancer, more preferably for use in the treatment of a cancer that is not a lymphoma or leukemia. An inhibitor of SYK and a chemotherapeutic agent are preferably formulated in a multiple dosage form, wherein an inhibitor of SYK is in one container and a chemotherapeutic agent is in another container. In a kit for use according to the invention, an inhibitor of SYK and a chemotherapeutic agent are preferably co-administered. Preferably, an inhibitor of SYK according to the invention is administered as adjuvant in such a way that in can clear, kill or reduce the viability of cells that have become senescent as a result of treatment with a chemotherapeutic agent. A kit according to the invention preferably comprises instructions on dosage regimens obtaining an optimal combined effect of an inhibitor of SYK and a chemotherapeutic agent.

In another aspect, the invention provides a method of treating a subject suffering, or suspected to suffer, from a disease or condition wherein the removal of senescent cells is beneficial, comprising a) administering an inhibitor of SYK, preferable R406, to a subject suffering, or suspected to suffer, from a disease or condition wherein the removal of senescent cells is beneficial; and wherein said disease or condition is not asthma, immune thrombocytopenia, hemolytic anemia, myeloid leukemia and/or lymphoma, preferably wherein said disease or condition is not asthma, immune thrombocytopenia, anemia, leukemia and/or lymphoma, more preferably wherein said disease or condition is not a lung disease, a bleeding disorder, leukemia and/or lymphoma. Alternatively, the invention provides a method of treating a subject suffering, or suspected to suffer, from a disease or condition wherein the removal of senescent cells is beneficial, comprising a) administering an inhibitor of SYK, preferable R406, to a subject suffering, or suspected to suffer, from atherosclerosis, chronic inflammatory diseases such as arthritis or athrosis, diabetes, diabetic ulcers, kyphosis, scoleosis, hepatic insufficiency, cirrhosis, Hutchinson-Gilford progeria syndrome (HGPS), laminopaties, osteoarthritis, osteoporosis, dementia, (cardio)vascular diseases, obesity, metabolic syndrome, acute myocardial infarction, emphysema, insulin sensitivity, boutonneuse fever, neurodegenerative diseases such as alzheimer's disease or parkinson's disease, Huntington's disease, cataracts, sarcopenia, hypertension, fibrosis, age-related macular degeneration, COPD, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty, reduced fitness and/or cancer selected from the group formed by adrenocortical carcinoma, anal cancer, appendix cancer, astrocytomas, basal cell carcinoma, bile duct cancer, bladder cancer, bone cancer, brain stem glioma, brain tumor, breast cancer, bronchial tumors, carcinoid tumor, cardiac (heart) tumors, central nervous system tumor, cervical cancer, chordoma, colon cancer, colorectal cancer, craniopharyngioma, ductal carcinoma, embryonal tumors, endometrial cancer, ependymoma, esophageal cancer, esthesioneuroblastoma, ewing sarcoma, extracranial germ cell tumor, extragonadal germ cell tumor, extrahepatic bile duct cancer, eye cancer, fallopian tube cancer, gallbladder cancer, gastric (stomach) cancer, gastrointestinal carcinoid tumor, germ cell tumor, head and neck cancer, hepatocellular (liver) cancer, hypopharyngeal cancer, kidney cancer, lung cancer, lip and oral cavity cancer, male breast cancer, metastatic squamous neck cancer, mouth cancer, nasal cavity and paranasal sinus cancer, ovarian cancer, pancreatic cancer, parathyroid cancer, penile cancer, prostate cancer, rectal cancer, salivary gland cancer skin cancer, small intestine cancer, stomach (gastric) cancer, thyroid cancer urethral cancer, vaginal cancer, and/or vulvar cancer. In a preferred embodiment of a method of the invention as mentioned above, said disease or condition is cancer, and said method further comprising the step of b) administering a chemotherapeutic agent to said subject and/or subjecting said subject to radiation therapy. In another preferred embodiment of a method of the invention as mentioned above, wherein the disease or condition is cancer, the inhibitor of SYK is administered or for administration, preferably as adjuvant, before, during and/or after administering a chemotherapeutic agent to said subject and/or before, during or after subjecting said subject to radiation therapy. In still another preferred embodiment of a method of the invention, wherein the disease or condition is cancer, the cancer is a resistant cancer having resistance to said chemotherapeutic agent. In an even more preferred embodiment of a method of the invention as mentioned hereinbefore, wherein the disease or condition is cancer, said resistant cancer is metastatic melanoma, breast cancer or glioblastoma and said at least one chemotherapeutic agent is a RAF, MEK or ERK inhibitor such as RAF265, trametinib, dabrafenib, selumetinib, vemurafenib and/or trametinib, more preferably vemurafenib and/or trametinib.

In another aspect, the invention provides a method of sensitizing a resistant cancer in a mammalian, preferably human, subject to a chemotherapeutic agent to which said cancer was or is resistant, comprising administering an inhibitor of SYK, preferably R406, to said subject. In a preferred embodiment of a method of sensitizing a resistant cancer, resistant cancer is metastatic melanoma, breast cancer or glioblastoma and said at least one chemotherapeutic agent is a RAF, MEK or ERK inhibitor such as RAF265, trametinib, dabrafenib, selumetinib, vemurafenib and/or trametinib, more preferably vemurafenib and/or trametinib.

In another aspect, the invention provides a method of treating a resistant cancer in a mammalian, preferably human, subject, comprising a) administering an inhibitor of SYK to a mammalian, preferably human, subject suffering, or suspected to suffer, from a resistant cancer; and b) administering a chemotherapeutic agent, preferably a chemotherapeutic agent said resistant cancer was or is resistant to, to said subject. Said inhibitor of SYK is preferably co-administered with said chemotherapeutic agent. In a preferred embodiment of a method of treating a resistant cancer, the resistant cancer is metastatic melanoma, breast cancer or glioblastoma, preferably metastatic melanoma, and the chemotherapeutic agent is a RAF, MEK or ERK inhibitor such as RAF265, trametinib, dabrafenib, selumetinib, vemurafenib and/or trametinib, more preferably vemurafenib and/or trametinib.

EXAMPLES

Example 1

FOXO4 DRI Peptide Selectively Clears Senescent Cells

Non-senescent (="normal", proliferating) IMR90 cells (ATCC #CCL-186, a diploid primary human fibroblast adherent cell line derived from fetal lung tissue) were irradiated with 10Gy Gamma-IR (IR=irradiation). After 7 days these cells are senescent and can be used for experiments comparing them to their non-irradiated (=non-senescent) counterparts. Senescent and non-senescent IMR90 fibroblasts were plated for longitudinal cell density measurement using the xCELLigence system (ACEA Biosciences, Inc., San Diego, Calif.). Once baseline measurements were established the cells were mock treated (PBS) or exposed to the FOXO4 DRI peptide (50 μM) and cell density after this treatment was followed in time as indicated. Note that after 36 h the FOXO4 DRI peptide selectively and gradually reduced cell density of senescent cells. The FOXO4 DRI peptide was ordered from PepScan Presto BV, Lelystad, the Netherlands. The FOXO4 DRI peptide, of which the amino acid sequence is in a D-Retro-Inverso Isoform, selectively reduces cell viability of senescent, but not non-senescent IMR90 fibroblast cells in time (.

Example 2

FOXO4 DRI Peptide is Effective in the Treatment of Diseases

Trichothiodystrophy is a human progeria syndrome leading to hair loss, neurological defects, bone abnormalities and fitness decline. Our department generated a mouse model based on a mutation in the Xpd gene, the $Xpd^{TTD/TTD}$ mouse model, which largely encompasses these features. We observed this mouse model to develop senescence at an accelerated pace, in conjunction with the fast aging phenotype. The $Xpd^{TTD/TTD}$ mouse is publicly available and is inter alia described in the literature (De Boer et al., Molecular Cell, 1(7), p. 981-990 (1998), De Boer et al., Cancer Res. 59(14):3489-94 (1999) and De Boer et al., Science, 296 (5571):1276-9 (2002)). This mouse model was used to assay the apoptosis inducing-activity of the FOXO4 DRI peptide having the amino acid sequence of SEQ ID NO:8, wherein all amino acids are D amino acids.

Wildtype (c57bl/6) or $Xpd^{TTD/TTD}$ mice were treated on days 3, 4, 5 and 6 with the FOXO4 DRI peptide by intravenous injection of a 10 mg/kg dose. Days 1 and 2 were baseline (control, no treatment) measurements. Ct scans were used to establish the curvature of the spine of the mice as a measure of Kyphosis. Muscle mass was measured by Ct scan followed by 3D volume rendering.

The fast aging mice showed a transient and reproducible increase in running behavior close to wildtype levels. Also the unhealthy weight loss of these mice was compensated by the FOXO4 DRI peptide. Note that after FOXO4 DRI peptide treatment the distance between the lowest and highest vertebrae increased indicating reduced kyphosis. In conclusion, normalization of weight loss, hair loss, kyphosis, muscle mass increase and fitness improvement in vivo of the $Xpd^{TTD/TTD}$ mouse model for aging occurred after treatment with the FOXO4 DRI peptide.

Example 3

ASK1-Inhibitor NQDI Clears Senescent Cells 5000 senescent (obtained as described above) and 2000 non-senescent IMR90 fibroblasts were plated in 96-well plates incubated with concentrations of NQDI between 0-20 μM and after 6 days cell viability was determined by AqueousOne CellTiter (MTT) assay according to the manufacturer's instructions.

Figure 12:
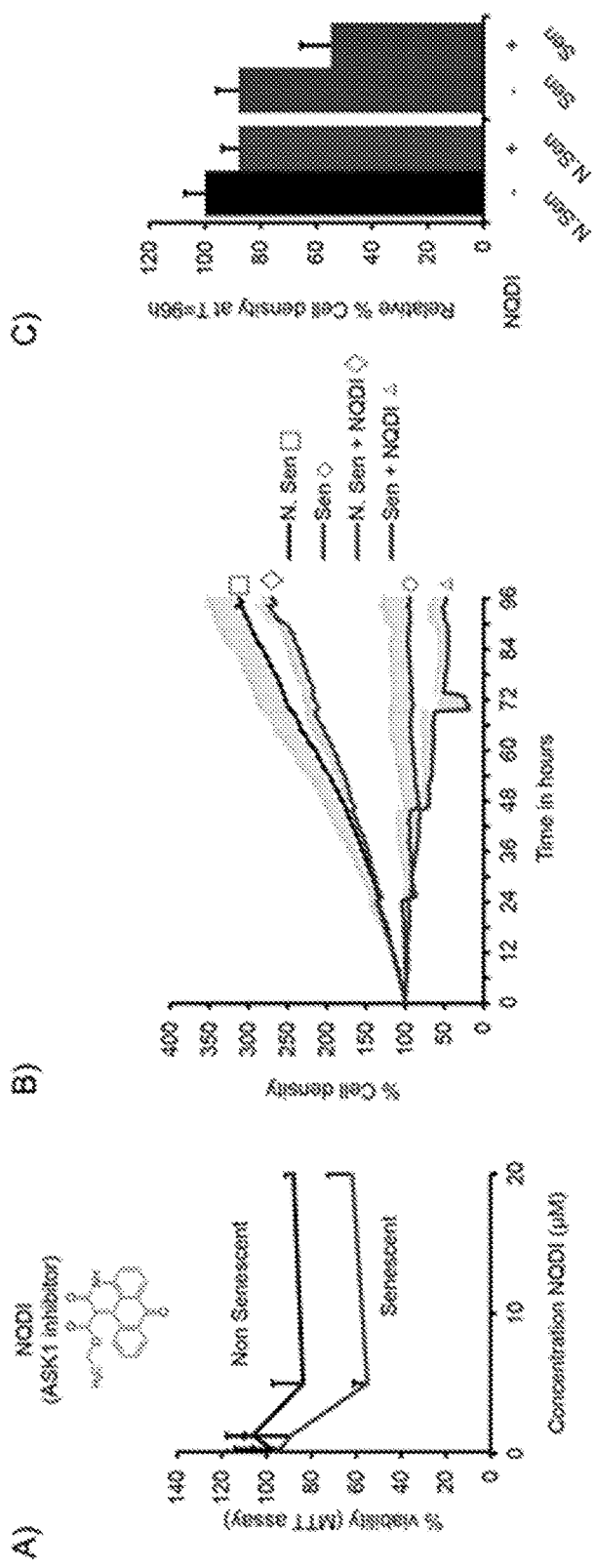
FIG. 12 shows that an ASK1 inhibitor selectively induces apoptosis in senescent cells. A) Shown is the % viability of NQDI-treated over Mock treated senescent and non-senescent IMR90 cells. The ASK1 inhibitor NQDI clearly reduces cell viability in senescent, but not non-senescent IMR90 fibroblasts. Senescent and non-senescent IMR90 fibroblasts were incubated with the indicated concentrations of NQDI and after 6 days cell viability was determined by using the CellTiter 96® AQueous One Solution Cell Proliferation Assay. B) Sequential rounds of NQDI enhance its effectivity towards senescent cell clearance. Senescent and non-senescent IMR90 fibroblasts were plated for longitudinal cell density measurement using the xCELLigence system (ACEA Biosciences, Inc., San Diego, Calif.). Once baseline measurements were established the cells were incubated on three consecutive days with 2 μM NQDI (24, 48 and 72 h, respectively). Cell density after time of plating was followed as indicated. The plot shows cell density data normalized to the density of that condition at the beginning of the experiment. C) The histogram shows a quantification of the change in cell density at the end of the measurement (96 h) over baseline.

Senescent and non-senescent IMR90 fibroblasts were plated for longitudinal cell density measurement using the xCELLigence system as described in Example 1 and incubated on three consecutive days with 2 μM NQDI (24, 48 and 72 h, respectively). Cell density after time of plating was followed. It was found that the ASK1 inhibitor NQDI reduces cell viability in senescent, but not non-senescent IMR90 fibroblasts. Sequential rounds of NQDI enhance its effectivity towards senescent cell clearance (FIG. 12). NQDI is apparently rather safe even at high doses as as non-senescent cells are not affected by 20 uM NQDI.

vExample 4

Figure 13:
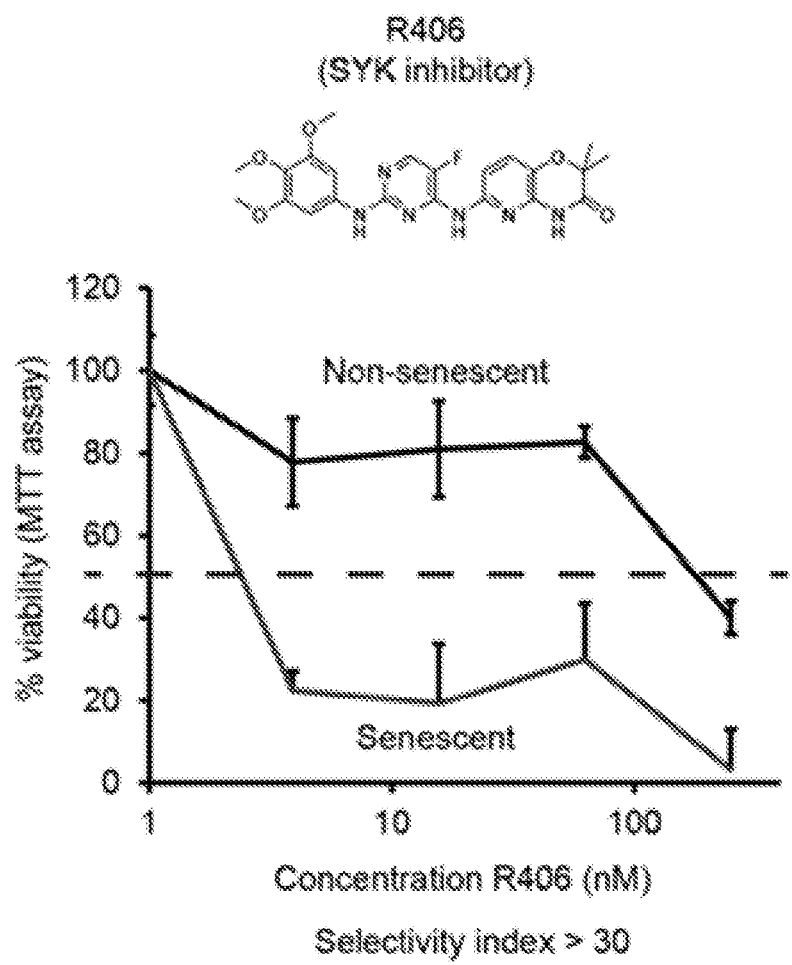
FIG. 13 shows that a SYK inhibitor selectively induces apoptosis in senescent cells in vitro. The graph shows % viability over Mock treated senescent and non-senescent IMR90 cells. The SYK inhibitor R406 selectively reduces senescent cell viability. Experiment performed in the same way as described for FIG. 12.

SYK-Inhibitor R406 Clears Senescent Cells 5000 senescent (obtained as described above) and 2000 non-senescent IMR90 fibroblasts were plated in 96-well plates incubated with concentrations of R406, ranging from 16, 32, 64 to 128 nM and after 6 days cell viability was determined by AqueousOne CellTiter (MTT) assay according to the manufacturer's instructions. It was found that the SYK inhibitor R406 selectively reduces senescent cell viability (FIG. 13).

Example 5

Chemotherapy (Doxorubicin) Induces Senescence In Vitro which is Counteracted by the FOXO4 DRI Peptide Normal human IMR90 fibroblasts were exposed to 10 Gy Ionizing Radiation or treated 3× (bidaily) with 0.5 µM Doxorubicin. Seven days later they were processed for SA-β-Gal staining to visualize senescent cells. Cells exposed to 1×10 Gy Ionizing Radiation or treated 3× (bidaily) with 0.5 µM Doxorubicin were processed for immunofluorescence to detect FOXO4 (Red) and p16$^{ink4a}$ (Green). DAPI was used as a counterstain to visualize nuclei. Cells are treated as described before and exposed to a mock treatment or the FOXO4 DRI peptide. After 6 days the cell viability was determined using an AqueousOne Celltiter (MTT) assay according to the manufacturer's instructions. The histograms show % viability for the indicated conditions (.

The FOXO4 DRI peptide selectively targets viability of cells induced to senesce by radiotherapy (IR) or chemotherapy (Doxorubicin).

Example 6

Chemotherapy (Doxorubicin) Induces Senescence In Vivo which is Counteracted by the FOXO4 DRI Peptide and R406

Our senescence-detection model makes use of a construct in which the promoter of p16$^{ink4a}$ drives a so-called trimodality reporter (3MR) referred to as p16::3MR. The 3MR reporter comprises a chimeric protein consisting of Renilla Luciferase (RLUC), Red Fluorescent Protein (RFP) and Thymidine Kinase (TK) from Herpes Simplex Virus. RLUC and RFP allow visualization of senescent cells in real-time through bioluminescence and fluorescence, respectively. Thymidine kinase allows apoptosis in an induced fashion through the compound Ganciclovir (GCV). On day 0, p16::3MR mice (Demaria et al., Developmental Cell, 31:6 p. 722-733 (2014)) including the Supplemental Experimental procedures) were i.p. injected with 10 mg/kg Doxorubicin and RLUC activity as measure of senescence was determined on the indicated timepoints.

On Day 11, 12, 13 and 14 they were once daily i.v. injected with PBS (Mock), 10 mg/kg FOXO4 DRI peptide (TASC treatment) or R406 (TASC treatment). Bioluminescence imaging to detect RLUC activity as measure for senescence was performed as indicated on day 11 (prior to TASC treatment) and on day 21 (10 days after TASC treatment).

It was found that Doxorubicin induces p16$^{ink4a}$-mediated senescence in vivo. The FOXO4 DRI peptide and R406 repress Doxorubicin-induced senescence in vivo, shown by reduced bioluminescence and reduced SA-beta-GAL deposits in kidneys.

Unexpectedly, upon sacrificing p16::3MR mice treated with doxorubicin, reduced values of ASAT and amylase, indicators of respectively liver toxicity and pancreas toxicity, were observed in plasma of mice treated with FOXO4 DRI peptide, whereas PBS treated mice showed increases toxicity levels as a result of Doxorubicin treatment.

It was even established that the FOXO 4 DRI peptide can kill cancer cells to some extent as a single entity, i.e. without chemotherapy.

Example 7

The FOXO4 DRI Peptide Sensitizes Metastatic Melanoma to Vemurafenib/Trametinib The sensitivity of the three human metastatic melanoma cell lines, Malme-3M, A375 and LOX-IMVI to increasing doses of Vemurafenib and Trametinib was established. LOX-IMVI cells express high levels of FOXO4 under basal conditions. The experiment was performed as described in Example 1, namely by AqueousOne MTT assay according to the manufacturer's instructions.

LOX-IMVI cells were plated for (i) cell viability assay as in example 1 by AqueousOne MTT assay, (ii) apoptosis by Cytochrome C release, (iii) longitudinal cell density assay, and incubated with the FOXO4 DRI peptide, Vemurafenib/Trametinib, or their combination, respectively. With regard to the apoptosis by Cytochrome C release experiment, 20.000 LOX-IMVI cells were plated on glass coverslips in 24-well plate wells. The next day these were incubated with PBS (Mock) or 50 uM of the FOXO4 in combination with PBS, 2 uM Vemurafenib or 10 nM Trametinib in the presence of 20 nM of the caspase-inhibitor QVD-OPH to prevent caspase-mediated death. The cells were refreshed after two days with new media containing 20 nM QVD-OPH and three days later the cells were fixed and processed for immunofluorescence-detection of Cytochrome C. Dying cells, which were prevented to detach from the coverslips due to the caspase inhibitor show release of Cytochrome C from mitochondria to the cytosol or even complete absence of Cytochrome C, while viable cells show mitochondrial staining only. The % of cells with Cytochrome C release was scored.

The longitudinal cell density assay, is an xCELLigence experiment as mentioned above for the senescence and non-senescent cells. Only in this case 5000 LOX-IMVI cells were used and 10 uM of A Rock inhibitor (Y-27632) was used to prevent anoikis, thus ensuring better attachment of the cells to the electrode.

The level of FOXO4 is induced by Vemurafenib as determined by QPCR (mRNA), Western Blot (protein) and immunofluorescence (protein expression and localization). The FOXO4 DRI peptide strongly enhances the ability of Vemurafenib and Trametinib to kill therapy-resistant LOX-IMVI melanoma cells.

In order to establish the individual effect of the FOXO4 DRI peptide on cancer, cells were plated for an MTT assay as described above. The cells were incubated with the FOXO4 DRI peptide or Mock and left for 6 days after which viability was scored. In several cell lines tested the peptide is clearly able to kill cancer cells.

Example 8

Treatment of Atherosclerosis Patients with the FOXO4 DRI Peptide

Two patient groups (each n=10) suffering from atherosclerosis are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, atherosclerosis disease parameters are measured in both patient groups, wherein a is the outcome for treated patients, b is the outcome for non-treated control patients, wherein when a is different from b, it is demonstrated that the FOXO4 DRI peptide is effective in the treatment of atherosclerosis. Atherosclerosis disease parameters are inter alia measured by blood tests including measurements of cholesterol, glucose, electrocardiogram, angiography, computerised tomography scan and/or ophthalmoscopy.

Example 9

Treatment of Arthritis Patients with the FOXO4 DRI Peptide

Two patient groups (each n=10) suffering from arthritis are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, arthritis disease parameters are measured in both patient groups, wherein a is the outcome for treated patients, b is the outcome for non-treated control patients, wherein when a is different from b, it is demonstrated that the FOXO4 DRI peptide is effective in the treatment of arthritis. Arthritis disease parameters that are to be measured are inter alia joint symptoms including swelling, pain, stiffness and decreased range of motion.

Example 10

Treatment of Metastatic Melanoma Patients with the FOXO4 DRI Peptide

Two patient groups (each n=10) suffering from metastatic melanoma and resistant to a RAF, MEK or ERK inhibitor are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, metastatic melanoma disease parameters are measured in both patient groups, wherein a is the outcome for treated patients, b is the outcome for non-treated control patients, wherein when a is different from b, it is demonstrated that the FOXO4 DRI peptide is effective in the treatment of metastatic melanoma. Metastatic melanoma disease parameters that are to be measured are inter alia reduction in tumor size and/or metastazation.

Example 11

Treatment of Resistant Breast Cancer Patients with the FOXO4 DRI Peptide

Two patient groups (each n=10) suffering from resistant breast cancer and resistant to FAC are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, resistant breast cancer disease parameters are measured in both patient groups, wherein a is the outcome for treated patients, b is the outcome for non-treated control patients, wherein when a is different from b, it is demonstrated that the FOXO4 DRI peptide is effective in the treatment of resistant breast cancer. Resistant breast cancer disease parameters that are to be measured are inter alia reduction in tumor size and/or metastazation.

Example 12

Treatment of Radiotherapy Resistant Glioblastoma Patients with the FOXO4 DRI Peptide Two patient groups (each n=10) suffering from resistant glioblastoma and resistant to radiotherapy are formed. The first patient group receives the FOXO 4 DRI peptide by intravenous administration using a single-dose injection of the FOXO 4 DRI peptide at a therapeutically effective dose (i.e. a pharmaceutically effective amount) and subjected to radiotherapy, while the second patient group is subjected to radiotherapy but does not receive the FOXO 4 DRI peptide (i.e. is non-treated or receives a placebo. One month after treatment, resistant glioblastoma disease parameters are measured in both patient groups, wherein a is the outcome for treated patients, b is the outcome for non-treated control patients, wherein when a is different from b, it is demonstrated that the FOXO4 DRI peptide is effective in the treatment of resistant glioblastoma. Resistant glioblastoma disease parameters that are to be measured are inter alia reduction in tumor size and/or metastazation.

Example 13

Treatment of Osteoarthritis Patients with the FOXO4 DRI Peptide

Two patient groups (each n=10) suffering from osteoarthritis are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, osteoarthritis disease parameters are measured in both patient groups, wherein a is the outcome for treated patients, b is the outcome for non-treated control patients, wherein when a is different from b, it is demonstrated that the FOXO4 DRI peptide is effective in the treatment of osteoarthritis. Osteoarthritis disease parameters that are to be measured are inter alia joint pain, redness, stiffness and/or swelling and joint motion range, X-RAY and/or MRI for bone spurs, blood tests and joint fluid analyses to rule out other causes.

Example 14

Treatment of Glomerulosclerosis Patients with the FOXO4 DRI Peptide

Two patient groups (each n=10) suffering from glomerulosclerosis are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, glomerulosclerosis disease parameters are measured in both patient groups, wherein a is the outcome for treated patients, b is the outcome for non-treated control patients, wherein when a is different from b, it is demonstrated that the FOXO4 DRI peptide is effective in the treatment of glomerulosclerosis. Glomerulosclerosis disease parameters that are to be measured are inter alia swellings in limbs, weight gains, changes in urine due to proteinuria, distortion or compression of the small capillaries in the glomerulus that filter blood in a biopsy and plasma [Urea] or [protein], blood pressure, glomerular filtration rate, and/or kidney ultrasound.

Example 15

Treatment of Diabetes Type II Patients with the FOXO4 DRI Peptide

Two patient groups (each n=10) suffering from diabetes type II are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, diabetes type II disease parameters are measured in both patient groups, wherein a is the outcome for treated patients, b is the outcome for non-treated control patients, wherein when a is different from b, it is demonstrated that the FOXO4 DRI peptide is effective in the treatment of diabetes type II.

Diabetes type II disease parameters that are to be measured are inter alia basal blood glucose levels, average blood glucose levels over a period of time (2-3 months; A1C test), fasting plasma glucose, oral glucose tolerance test, plasma glucose test N.B. For type 1, this is: hyperglycemia, glucose and ketones in urine, oral glucose tolerance test, A1C test, Example 16

Treatment of Kyphosis Patients with the FOXO4 DRI Peptide

Two patient groups (each n=10) suffering from kyphosis are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, kyphosis disease parameters are measured in both patient groups, wherein a is the outcome for treated patients, b is the outcome for non-treated control patients, wherein when a is different from b, it is demonstrated that the FOXO4 DRI peptide is effective in the treatment of kyphosis. Kyphosis disease parameters that are to be measured are inter alia measurement of spine curvature by X-RAY, CT and/or MRI.

Example 17

Treatment of Scoliosis Patients with the FOXO4 DRI Peptide

Two patient groups (each n=10) suffering from scoliosis are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, scoliosis disease parameters are measured in both patient groups, wherein a is the outcome for treated patients, b is the outcome for non-treated control patients, wherein when a is different from b, it is demonstrated that the FOXO4 DRI peptide is effective in the treatment of scoliosis. Scoliosis disease parameters that are to be measured are inter alia physical examination of spine, ribs, hips and shoulders and/or X-RAY, CT and/or MRI to determine bone curvature.

Example 18

Treatment of Hepatic Insufficiency Patients with the FOXO4 DRI Peptide

Two patient groups (each n=10) suffering from hepatic insufficiency are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, hepatic insufficiency disease parameters are measured in both patient groups, wherein a is the outcome for treated patients, b is the outcome for non-treated control patients, wherein when a is different from b, it is demonstrated that the FOXO4 DRI peptide is effective in the treatment of hepatic insufficiency. Hepatic insufficiency disease parameters that are to be measured are inter alia blood AST and ALT values.

Example 19

Treatment of Cirrhosis Patients with the FOXO4 DRI Peptide

Two patient groups (each n=10) suffering from cirrhosis are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, cirrhosis disease parameters are measured in both patient groups, wherein a is the outcome for treated patients, b is the outcome for non-treated control patients, wherein when a is different from b, it is demonstrated that the FOXO4 DRI peptide is effective in the treatment of cirrhosis. Cirrhosis disease parameters that are to be measured are inter alia measurements of blood-clotting factors and international normalized ratio for blood clotting, liver stiffness by magnetic resonance elastography, lver imaging by CT and/or MRI, physical examination, blood testing for bilirubin and creatinine, and/or liver biopsy analysis for liver damage.

Example 20

Treatment of Hutchinson-Gilford Progeria Syndrome (HGPS) Patients with the FOXO4 DRI Peptide Two patient groups (each n=10) suffering from HGPS are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, HGPS disease parameters are measured in both patient groups, wherein a is the outcome for treated patients, b is the outcome for non-treated control patients, wherein when a is different from b, it is demonstrated that the FOXO4 DRI peptide is effective in the treatment of HGPS. HGPS disease parameters that are to be measured are inter alia features of accelerated aging, hair loss (alopecia), aged-looking skin, joint abnormalities, and a loss of fat under the skin.

Example 21

Treatment of (Cardio)Vascular Disease Patients with the FOXO4 DRI Peptide

Two patient groups (each n=10) suffering from (cardio)vascular disease are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, (cardio)vascular disease parameters are measured in both patient groups, wherein a is the outcome for treated patients, b is the outcome for non-treated control patients, wherein when a is different from b, it is demonstrated that the FOXO4 DRI peptide is effective in the treatment of (cardio)vascular disease. (cardio)vascular disease parameters that are to be measured are inter alia cardiac ejection fraction, blood vessel stiffness and blood pressure.

Example 22

Treatment of Obesity Patients with the FOXO4 DRI Peptide

Two patient groups (each n=10) suffering from obesity are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, obesity parameters are measured in both patient groups, wherein a is the outcome for treated patients, b is the outcome for non-treated control patients, wherein when a is different from b, it is demonstrated that the FOXO4 DRI peptide is effective in the treatment of obesity. Obesity parameters that are to be measured are inter alia body weight, Body-Mass-Index (BMI), waist circumference, waist-to-hip ratio, skinfold thicknesses, and bioelectrical impedance, magnetic resonance imaging anr/or dual energy X-ray absorptiometry Example 23

Treatment of Lung Emphysema Patients with the FOXO4 DRI Peptide

Two patient groups (each n=10) suffering from lung emphysema are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, lung emphysema disease parameters are measured in both patient groups, wherein a is the outcome for treated patients, b is the outcome for non-treated control patients, wherein when a is different from b, it is demonstrated that the FOXO4 DRI peptide is effective in the treatment of lung emphysema. Lung emphysema disease parameters that are to be measured are inter alia breathlessness, chest size, decreased breath sounds through the stethoscope, fingertip shape, style of breathing, hypoxemia, hypercaria, cyanosis, malnutrition. Lung volume, lung ejection capacity, dead volume in the lungs, airflow changes after bronchodilator medication, chest X-RAY and CT scan of the chest and red blood cell counts.

Example 24

Treatment of Boutonneuse Fever Patients with the FOXO4 DRI Peptide

Two patient groups (each n=10) suffering from boutonneuse fever are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, boutonneuse fever disease parameters are measured in both patient groups, wherein a is the outcome for treated patients, b is the outcome for non-treated control patients, wherein when a is different from b, it is demonstrated that the FOXO4 DRI peptide is effective in the treatment of boutonneuse fever. Boutonneuse fever disease parameters that are to be measured are inter alia Weil-Felix test (agglutination of Proteus OX strains), ELISA, or immunofluorescence assays in a biopsy of the lesion.

Example 25

Treatment of Alzheimer's Disease Patients with the FOXO4 DRI Peptide

Two patient groups (each n=10) suffering from Alzheimer's disease are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, Alzheimer's disease parameters are measured in both patient groups, wherein a is the outcome for treated patients, b is the outcome for non-treated control patients, wherein when a is different from b, it is demonstrated that the FOXO4 DRI peptide is effective in the treatment of Alzheimer's disease. Alzheimer's disease parameters that are to be measured are inter alia changes in ability to carry out daily activities, and changes in behavior and personality, tests of memory, problem solving, attention, counting, and language, blood and urine tests, brain scans, such as computed tomography (CT), magnetic resonance imaging (MRI), or positron emission tomography (PET) and/or biomarker analysis.

Example 26

Treatment of Parkinson's Disease Patients with the FOXO4 DRI Peptide

Two patient groups (each n=10) suffering from Parkinson's disease are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, Parkinson's disease parameters are measured in both patient groups, wherein a is the outcome for treated patients, b is the outcome for non-treated control patients, wherein when a is different from b, it is demonstrated that the FOXO4 DRI peptide is effective in the treatment of Parkinson's disease. Parkinson's disease parameters that are to be measured are inter alia analysis for tremors, limb or neck stiffness, general fitness and balance and/or locomotor function.

Example 27

Treatment of COPD Patients with the FOXO4 DRI Peptide

Two patient groups (each n=10) suffering from COPD are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, COPD disease parameters are measured in both patient groups, wherein a is the outcome for treated patients, b is the outcome for non-treated control patients, wherein when a is different from b, it is demonstrated that the FOXO4 DRI peptide is effective in the treatment of COPD. COPD disease parameters that are to be measured are inter alia spirometry and lung functional tests as described for lung emphysema, including breathlessness, chest size, decreased breath sounds through the stethoscope, fingertip shape, style of breathing, hypoxemia, hypercaria, cyanosis, malnutrition. Lung volume, lung ejection capacity, dead volume in the lungs, airflow changes after bronchodilator medication, chest X-RAY and CT scan of the chest and red blood cell counts.

Example 28

Treatment of Renal Insufficiency Patients with the FOXO4 DRI Peptide

Two patient groups (each n=10) suffering from renal insufficiency are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, renal insufficiency disease parameters are measured in both patient groups, wherein a is the outcome for treated patients, b is the outcome for non-treated control patients, wherein when a is different from b, it is demonstrated that the FOXO4 DRI peptide is effective in the treatment of renal insufficiency. Renal insufficiency disease parameters that are to be measured are inter alia blood pressure, heart/lung sound analysis nervous system exam, urinalaysis for protein content, analysis for creatinine clearance and level of Blood Urea Nitrogen, CT, MRI and/or ultrasound of abdomen and kidneys, kidney biopsy for damage analysis.

Example 29

Treatment of Patients with Depression with the FOXO4 DRI Peptide

Two patient groups (each n=10) suffering from depression are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, depression parameters are measured in both patient groups, wherein a is the outcome for treated patients, b is the outcome for non-treated control patients, wherein when a is different from b, it is demonstrated that the FOXO4 DRI peptide is effective in the treatment of depression. depression parameters that are to be measured are inter alia physical examination, sadness or depressed mood most of the day, major changes in weight, insomnia or excessive sleep, fatigue or loss of energy most of the day, feelings of hopelessness or worthlessness or excessive guilt, problems with concentration or decision making, recurring thoughts of death or suicide.

Example 30

Treatment of Metabolic Syndrome Patients with the FOXO4 DRI Peptide

Two patient groups (each n=10) suffering from metabolic syndrome are formed. The first patient group receives the FOXO 4 DRI peptide by intravenous administration using a single-dose injection of the FOXO 4 DRI peptide at a therapeutically effective dose (i.e. a pharmaceutically effective amount), while the second patient group is non-treated or receives a placebo. One month after treatment, metabolic syndrome parameters are measured in both patient groups, wherein a is the outcome for treated patients, b is the outcome for non-treated control patients, wherein when a is different from b, it is demonstrated that the FOXO4 DRI peptide is effective in the treatment of metabolic syndrome. Metabolic syndrome disease parameters that are to be measured are inter alia measurements for obesity (see above, e.g. waist circumfence), blood levels of triglicerides, HDL cholesterol, blood pressure, fasting glucose.

The invention claimed is:

1. A peptide comprising the amino acid sequence of SEQ ID NO:6, wherein all of the amino acids in said peptide are D-amino acid residues.

2. The peptide according to claim 1, further comprising a cell-penetrating peptide sequence.

3. The peptide according to claim 2, wherein said cell-penetrating peptide is fused to the C-terminal part of said peptide.

4. A pharmaceutical composition comprising a peptide according to claim 1, optionally further comprising a chemotherapeutic agent.

5. A method of inducing apoptosis in a senescent cell, the method comprising providing the peptide of claim 1 to said senescent cell.

6. The peptide according to claim 2, wherein said cell-penetrating peptide sequence has the amino acid sequence of SEQ ID NO:1.

7. The peptide according to claim 2, wherein all of the amino acids in said cell-penetrating peptide sequence are D-amino acid residues.

8. The peptide of claim 1, wherein said peptide exhibits apoptosis-inducing activity in senescent cells.

* * * * *

SEQUENCE LISTING

```
<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: cell-penetrating peptide sequence

<400> SEQUENCE: 1
```

```
Pro Pro Arg Arg Arg Gln Arg Arg Lys Lys Arg Gly
1               5                   10
```

<210> SEQ ID NO 2
<211> LENGTH: 46
<212> TYPE: PRT
<213> ORGANISM: Artificial Sequence
<220> FEATURE:
<223> OTHER INFORMATION: FOXO4 DRI negative control

<400> SEQUENCE: 2

```
Gly Arg Lys Lys Arg Arg Gln Arg Arg Pro Pro Arg Lys Gly
1               5                   10                  15

Gly Ser Arg Arg Asn Ala Trp Gly Asn Gln Ser Tyr Ala Glu Leu Ile
            20                  25                  30

Ser Gln Ala Ile Glu Ser Ala Pro Glu Lys Arg Leu Thr Leu
        35                  40                  45
```

<210> SEQ ID NO 3
<211> LENGTH: 505
<212> TYPE: PRT
<213> ORGANISM: Homo sapiens

<400> SEQUENCE: 3

```
Met Asp Pro Gly Asn Glu Asn Ser Ala Thr Glu Ala Ala Ile Ile
1               5                   10                  15

Asp Leu Asp Pro Asp Phe Glu Pro Gln Ser Arg Pro Arg Ser Cys Thr
                20                  25                  30

Trp Pro Leu Pro Arg Pro Glu Ile Ala Asn Gln Pro Ser Glu Pro Pro
            35                  40                  45

Glu Val Glu Pro Asp Leu Gly Glu Lys Val His Thr Glu Gly Arg Ser
        50                  55                  60

Glu Pro Ile Leu Leu Pro Ser Arg Leu Pro Glu Pro Ala Gly Pro
65                  70                  75                  80

Gln Pro Gly Ile Leu Gly Ala Val Thr Gly Pro Arg Lys Gly Gly Ser
                85                  90                  95

Arg Arg Asn Ala Trp Gly Asn Gln Ser Tyr Ala Glu Leu Ile Ser Gln
            100                 105                 110

Ala Ile Glu Ser Ala Pro Glu Lys Arg Leu Thr Leu Ala Gln Ile Tyr
        115                 120                 125

Glu Trp Met Val Arg Thr Val Pro Tyr Phe Lys Asp Lys Gly Asp Ser
    130                 135                 140

Asn Ser Ser Ala Gly Trp Lys Asn Ser Ile Arg His Asn Leu Ser Leu
145                 150                 155                 160

His Ser Lys Phe Ile Lys Val His Asn Glu Ala Thr Gly Lys Ser Ser
                165                 170                 175

Trp Trp Met Leu Asn Pro Glu Gly Gly Lys Ser Gly Lys Ala Pro Arg
            180                 185                 190

Arg Arg Ala Ala Ser Met Asp Ser Ser Lys Leu Leu Arg Gly Arg
        195                 200                 205

Ser Lys Ala Pro Lys Lys Lys Pro Ser Val Leu Pro Ala Pro Pro Glu
    210                 215                 220

Gly Ala Thr Pro Thr Ser Pro Val Gly His Phe Ala Lys Trp Ser Gly
225                 230                 235                 240

Ser Pro Cys Ser Arg Asn Arg Glu Glu Ala Asp Met Trp Thr Thr Phe
                245                 250                 255

Arg Pro Arg Ser Ser Ser Asn Ala Ser Ser Val Ser Thr Arg Leu Ser
```

-continued

```
                260                 265                 270
Pro Leu Arg Pro Glu Ser Glu Val Leu Ala Glu Ile Pro Ala Ser
            275                 280                 285
Val Ser Ser Tyr Ala Gly Gly Val Pro Thr Leu Asn Glu Gly Leu
        290                 295                 300
Glu Leu Leu Asp Gly Leu Asn Leu Thr Ser His Ser Leu Leu Ser
305                 310                 315                 320
Arg Ser Gly Leu Ser Gly Phe Ser Leu Gln His Pro Gly Val Thr Gly
                325                 330                 335
Pro Leu His Thr Tyr Ser Ser Ser Leu Phe Ser Pro Ala Glu Gly Pro
            340                 345                 350
Leu Ser Ala Gly Glu Gly Cys Phe Ser Ser Gln Ala Leu Glu Ala
        355                 360                 365
Leu Leu Thr Ser Asp Thr Pro Pro Pro Ala Asp Val Leu Met Thr
        370                 375                 380
Gln Val Asp Pro Ile Leu Ser Gln Ala Pro Thr Leu Leu Leu Gly
385                 390                 395                 400
Gly Leu Pro Ser Ser Lys Leu Ala Thr Gly Val Gly Leu Cys Pro
                405                 410                 415
Lys Pro Leu Glu Ala Pro Gly Pro Ser Ser Leu Val Pro Thr Leu Ser
            420                 425                 430
Met Ile Ala Pro Pro Val Met Ala Ser Ala Pro Ile Pro Lys Ala
        435                 440                 445
Leu Gly Thr Pro Val Leu Thr Pro Thr Glu Ala Ala Ser Gln Asp
        450                 455                 460
Arg Met Pro Gln Asp Leu Asp Leu Asp Met Tyr Met Glu Asn Leu Glu
465                 470                 475                 480
Cys Asp Met Asp Asn Ile Ile Ser Asp Leu Met Asp Glu Gly Glu Gly
                485                 490                 495
Leu Asp Phe Asn Phe Glu Pro Asp Pro
            500                 505

<210> SEQ ID NO 4
<211> LENGTH: 450
<212> TYPE: PRT
<213> ORGANISM: Homo sapiens

<400> SEQUENCE: 4

Met Asp Pro Gly Asn Glu Asn Ser Ala Thr Glu Ala Ala Ile Ile
1               5                   10                  15
Asp Leu Asp Pro Asp Phe Glu Pro Gln Ser Arg Pro Arg Ser Cys Thr
                20                  25                  30
Trp Pro Leu Pro Arg Pro Glu Ile Ala Asn Gln Pro Ser Glu Pro Pro
            35                  40                  45
Glu Val Glu Pro Asp Leu Gly Glu Lys Ala Ile Glu Ser Ala Pro Glu
        50                  55                  60
Lys Arg Leu Thr Leu Ala Gln Ile Tyr Glu Trp Met Val Arg Thr Val
65                  70                  75                  80
Pro Tyr Phe Lys Asp Lys Gly Asp Ser Asn Ser Ser Ala Gly Trp Lys
                85                  90                  95
Asn Ser Ile Arg His Asn Leu Ser Leu His Ser Lys Phe Ile Lys Val
                100                 105                 110
His Asn Glu Ala Thr Gly Lys Ser Ser Trp Trp Met Leu Asn Pro Glu
            115                 120                 125
```

```
Gly Gly Lys Ser Gly Lys Ala Pro Arg Arg Ala Ser Met Asp
    130                 135                 140
Ser Ser Ser Lys Leu Leu Arg Gly Arg Ser Lys Ala Pro Lys Lys
145                 150                 155                 160
Pro Ser Val Leu Pro Ala Pro Glu Gly Ala Thr Pro Thr Ser Pro
                165                 170                 175
Val Gly His Phe Ala Lys Trp Ser Gly Ser Pro Cys Ser Arg Asn Arg
                180                 185                 190
Glu Glu Ala Asp Met Trp Thr Thr Phe Arg Pro Arg Ser Ser Ser Asn
                195                 200                 205
Ala Ser Ser Val Ser Thr Arg Leu Ser Pro Leu Arg Pro Glu Ser Glu
    210                 215                 220
Val Leu Ala Glu Glu Ile Pro Ala Ser Val Ser Ser Tyr Ala Gly Gly
225                 230                 235                 240
Val Pro Pro Thr Leu Asn Glu Gly Leu Glu Leu Leu Asp Gly Leu Asn
                245                 250                 255
Leu Thr Ser Ser His Ser Leu Leu Ser Arg Ser Gly Leu Ser Gly Phe
                260                 265                 270
Ser Leu Gln His Pro Gly Val Thr Gly Pro Leu His Thr Tyr Ser Ser
    275                 280                 285
Ser Leu Phe Ser Pro Ala Glu Gly Pro Leu Ser Ala Gly Glu Gly Cys
    290                 295                 300
Phe Ser Ser Ser Gln Ala Leu Glu Ala Leu Leu Thr Ser Asp Thr Pro
305                 310                 315                 320
Pro Pro Pro Ala Asp Val Leu Met Thr Gln Val Asp Pro Ile Leu Ser
                325                 330                 335
Gln Ala Pro Thr Leu Leu Leu Gly Gly Leu Pro Ser Ser Ser Lys
                340                 345                 350
Leu Ala Thr Gly Val Gly Leu Cys Pro Lys Pro Leu Glu Ala Pro Gly
    355                 360                 365
Pro Ser Ser Leu Val Pro Thr Leu Ser Met Ile Ala Pro Pro Val
370                 375                 380
Met Ala Ser Ala Pro Ile Pro Lys Ala Leu Gly Thr Pro Val Leu Thr
385                 390                 395                 400
Pro Pro Thr Glu Ala Ala Ser Gln Asp Arg Met Pro Gln Asp Leu Asp
                405                 410                 415
Leu Asp Met Tyr Met Glu Asn Leu Glu Cys Asp Met Asp Asn Ile Ile
                420                 425                 430
Ser Asp Leu Met Asp Glu Gly Glu Gly Leu Asp Phe Asn Phe Glu Pro
    435                 440                 445
Asp Pro
    450

<210> SEQ ID NO 5
<211> LENGTH: 3365
<212> TYPE: DNA
<213> ORGANISM: Homo sapiens

<400> SEQUENCE: 5
aaaaggggga gggaactgcg gctaaggaga cgttcggtga tgggagcgca atatatgagg      60
ggatacagtg cctcaggttt aaaagagcag gaagctgagt gagaggttgc agaaaaagtg     120
tcttcgctcg gcagaggtta caggtggcat ctcagaaaga gctttgaggc tacaggctgt     180
agtcgggaag gggatcggag aactgtgtga agggacagct tagggactag cgtcctggga     240
```

```
ctaggggaa gttcgcgact ttctgaagac tggcaggaat gtgcctcctg gccctcgatg      300
cttcccccct gagggaggc atcgtgaggg actgtggcag gcttcactga acgctgagcc      360
ggggaggtcc aactccacgt atggatccgg ggaatgagaa ttcagccaca gaggctgccg      420
cgatcataga cctagatccc gacttcgaac cccagagccg tccccgctcc tgcacctggc      480
cccttccccg accagagatc gctaaccagc cgtccgagcc gcccgaggtg gagccagatc      540
tgggggaaaa ggtacacacg gaggggcgct cagagccgat cctgttgccc tctcggctcc      600
cagagccggc cggggcccc cagcccggaa tcctgggggc tgtaacaggt cctcggaagg      660
gaggctcccg ccggaatgcc tggggaaatc agtcatatgc agaactcatc agccaggcca      720
ttgaaagcgc cccggagaag cgactgacac ttgcccagat ctacgagtgg atggtccgta      780
ctgtacccta cttcaaggac aagggtgaca gcaacagctc agcaggatgg aagaactcga      840
tccgccacaa cctgtccctg cacagcaagt tcatcaaggt tcacaacgag gccaccggca      900
aaagctcttg gtggatgctg aaccctgagg gaggcaagag cggcaaagcc cccgccgcc      960 gggccgcctc catggatagc agcagcaagc tgctccgggg ccgcagtaaa gcccccaaga     1020
agaaaccatc tgtgctgcca gctccacccg aaggtgccac tccaacgagc cctgtcggcc     1080
actttgccaa gtggtcaggc agcccttgct ctcgaaaccg tgaagaagcc gatatgtgga     1140
ccaccttccg tccacgaagc agttcaaatg ccagcagtgt cagcacccgg ctgtccccct     1200
tgaggccaga gtctgaggtg ctggcggagg aaataccagc ttcagtcagc agttatgcag     1260
ggggtgtccc tcccaccctc aatgaaggtc tagagctgtt agatgggctc aatctcacct     1320
cttcccattc cctgctatct cggagtggtc tctctggctt ctcttttgcag catcctgggg     1380 ttaccggccc cttacacacc tacagcagct ccttttcag cccagcagag gggcccctgt      1440
cagcaggaga agggtgcttc tccagctccc aggctctgga ggccctgctc acctctgata     1500
cgccaccacc cctgctgac gtcctcatga cccaggtaga tcccattctg tcccaggctc      1560
cgactcttct gttgctgggg gggcttcctt cctccagtaa gctggccacg ggcgtcggcc     1620
tgtgtcccaa gcccctagag gctccaggcc ccagcagtct ggttcccacc ctttctatga     1680
tagcaccacc tccagtcatg gcaagtgccc ccatccccaa ggctctgggg actcctgtgc     1740 tcacacccc tactgaagct gcaagccaag acagaatgcc tcaggatcta gatcttgata      1800
tgtatatgga gaacctggag tgtgacatgg ataacatcat cagtgacctc atggatgagg     1860
gcgagggact ggacttcaac tttgagccag atccctgagt catgcctgga agctttgtcc     1920
cctgcttcag atgtggagcc aggcgtgttc atatctactc tttacccttg agccctcccc     1980
aggaatttgg gaccctgctt tagagctagg gtggggtctg gtcacacaca ggtgttgaag     2040
aaattataaa gataaagctg ccccatctgg ggacgtatg ggggagggaga tgggagggga     2100 aaggggagag ggttttttctc actgtgccaa ttagggggta aggcccctc tcaggagcca      2160 tcatcggctt tccccattcc tacccactta ggctttgtag caagatgagc aatgctgttg     2220
gaaatgtgaa gtcaccagtg gccttacccc tgcctttggg agcaggattt ttttgtagag     2280
agtcttatct gagctgagcc aggctagctg gagcctggga tttctatgca gtggcccctt     2340
aggccagtga tgtgcggtgg gtgggctgtt taggggatct ggaagggcca aggtctgagc     2400
actggagtgg ctcgccaggc caaatcaccc ttagaaggct gcagataaca gaaaggcttt     2460
ttataaactt ttaaagaaat ataaacacaa atatagagat tttttaacca tggcagggtg     2520
ctagtggtgg gcagaatgct tttttttctt tctgaaggct ttgtgatagt gacatgatac     2580
aaacactaca gacaataaat attaggagac acagggaagt ggggagaggt ggggagtaat     2640
```

-continued

```
agtaaacaca gggaagagct cccctacgga ccaggtatag agaaaggtct atgcagaaat    2700
aggttagagt ttccctaaca aaaaagctaa cccaggtccc ctcattcctt caacttgtgc    2760
ctgggagtgt gtggtgttag ggtgcagcca cactcttcta tgacccagca tgggttagtg    2820
ctatggtggg agagtacatt gaaggcctgg aattagcttg gggccaggga agggactggg    2880
aggggagaga agagaaggag ggaaggattt aggatggtaa agttaggtac agagacctcc    2940
ctgttcaagg cccctgacag ctgtccctgc ccttcttccc cttccctgac tgcagggggtt   3000 atgtggaagt gtgtgtggca gcaggcagcg gggagggggag gaacagggaa ggggggagctg  3060 gggagcttgg ctgagggtct gggaaatgag cagggatggg gggggatgtg gatcaggttt   3120
actagcacct gccagggagg ccatctgggg ctccttctcc accccagccc ccaaagcagc   3180
ccttccccca gtgcccttg catcgtcccc tcccccaccc ctgctgtggg ttcccatcat    3240
ttcctgtgtc agcgcctggc ctacccagat tgtatcatgt gctagattgg agtggggaag   3300
tgtgtcaaat caataaatga ataaattcaa taaatgccta taaccagcaa aaaaaaaaa    3360 aaaaa                                                                3365
```

<210> SEQ ID NO 6
<211> LENGTH: 34
<212> TYPE: PRT
<213> ORGANISM: Artificial Sequence
<220> FEATURE:
<223> OTHER INFORMATION: FOXO4 DRI

<400> SEQUENCE: 6

Leu Thr Leu Arg Lys Glu Pro Ala Ser Glu Ile Ala Gln Ser Ile Leu
1               5                   10                  15

Glu Ala Tyr Ser Gln Asn Gly Trp Ala Asn Arg Arg Ser Gly Gly Lys
            20                  25                  30

Arg Pro

<210> SEQ ID NO 7
<211> LENGTH: 16
<212> TYPE: PRT
<213> ORGANISM: Artificial Sequence
<220> FEATURE:
<223> OTHER INFORMATION: FOXO4 DRI

<400> SEQUENCE: 7

Ser Glu Ile Ala Gln Ser Ile Leu Glu Ala Tyr Ser Gln Asn Gly
1               5                   10                  15

Trp

<210> SEQ ID NO 8
<211> LENGTH: 46
<212> TYPE: PRT
<213> ORGANISM: Artificial Sequence
<220> FEATURE:
<223> OTHER INFORMATION: FOXO4 DRI

<400> SEQUENCE: 8

Leu Thr Leu Arg Lys Glu Pro Ala Ser Glu Ile Ala Gln Ser Ile Leu
1               5                   10                  15

Glu Ala Tyr Ser Gln Asn Gly Trp Ala Asn Arg Arg Ser Gly Gly Lys
            20                  25                  30

Arg Pro Pro Pro Arg Arg Arg Gln Arg Arg Lys Lys Arg Gly
        35                  40                  45

```
<210> SEQ ID NO 9
<211> LENGTH: 6
<212> TYPE: PRT
<213> ORGANISM: Artificial Sequence
<220> FEATURE:
<223> OTHER INFORMATION: FOXO4 domain

<400> SEQUENCE: 9

Pro Arg Lys Gly Gly Ser
1               5

<210> SEQ ID NO 10
<211> LENGTH: 60
<212> TYPE: PRT
<213> ORGANISM: Homo sapiens
<220> FEATURE:
<223> OTHER INFORMATION: FOXO4 domain

<400> SEQUENCE: 10

Gly Ser His Met Leu Glu Asp Pro Gly Ala Val Thr Gly Pro Arg Lys
1               5                   10                  15

Gly Gly Ser Arg Arg Asn Ala Trp Gly Asn Gln Ser Tyr Ala Glu Leu
                20                  25                  30

Ile Ser Gln Ala Ile Glu Ser Ala Pro Glu Lys Arg Leu Thr Leu Ala
                35                  40                  45

Gln Ile Tyr Glu Trp Met Val Arg Thr Val Pro Tyr
        50                  55                  60
```